(12) United States Patent
Hess et al.

(10) Patent No.: US 9,095,388 B2
(45) Date of Patent: Aug. 4, 2015

(54) BONE PLATE ASSEMBLY WITH PLATES THAT RATCHET TOGETHER

(71) Applicant: Spinal Simplicity LLC, Lenexa, KS (US)

(72) Inventors: Harold Hess, Leawood, KS (US); Melissa Frock, Larwill, IN (US); Todd Moseley, Olathe, KS (US); Adam Rogers, Norfolk, VA (US); Jonathan Hess, Kansas City, MO (US); Paul Sand, Redwood City, CA (US)

(73) Assignee: Spinal Simplicity LLC, Lenexa, KS (US)

( * ) Notice: Subject to any disclaimer, the term of this patent is extended or adjusted under 35 U.S.C. 154(b) by 0 days.

(21) Appl. No.: 14/537,303

(22) Filed: Nov. 10, 2014

(65) Prior Publication Data

US 2015/0073416 A1    Mar. 12, 2015

Related U.S. Application Data

(60) Continuation of application No. 14/052,880, filed on Oct. 14, 2013, now Pat. No. 8,882,812, which is a division of application No. 13/586,083, filed on Aug. 15, 2012, now Pat. No. 8,574,270, which is a continuation-in-part of application No. 12/724,420, filed on Mar. 15, 2010, now Pat. No. 8,262,711.

(60) Provisional application No. 61/160,154, filed on Mar. 13, 2009.

(51) Int. Cl.
| | | |
|---|---|---|
| A61B 17/66 | (2006.01) | |
| A61B 17/80 | (2006.01) | |
| A61B 17/70 | (2006.01) | |
| A61B 17/86 | (2006.01) | |
| A61B 17/88 | (2006.01) | |

(52) U.S. Cl.
CPC ......... *A61B 17/8009* (2013.01); *A61B 17/7059* (2013.01); *A61B 17/8004* (2013.01); *A61B 17/809* (2013.01); *A61B 17/8042* (2013.01); *A61B 17/8047* (2013.01); *A61B 17/8605* (2013.01); *A61B 17/8875* (2013.01)

(58) Field of Classification Search
CPC combination set(s) only.
See application file for complete search history.

(56) References Cited

U.S. PATENT DOCUMENTS

| | | |
|---|---|---|
| 4,269,180 A | 5/1981 | Dall et al. |
| 4,998,936 A | 3/1991 | Mehdian et al. |
| 5,180,381 A | 1/1993 | Aust et al. |
| 5,201,735 A | 4/1993 | Chapman et al. |
| 5,209,756 A | 5/1993 | Seedhom et al. |
| 5,330,477 A | 7/1994 | Crook |
| 5,364,399 A | 11/1994 | Lowery et al. |
| 5,531,554 A | 7/1996 | Jeanson et al. |
| 5,558,674 A | 9/1996 | Heggeness et al. |
| 5,578,034 A | 11/1996 | Estes |
| 5,603,713 A | 2/1997 | Aust et al. |
| 5,735,853 A | 4/1998 | Olerud |
| 5,836,948 A | 11/1998 | Zucherman et al. |
| 5,876,402 A | 3/1999 | Errico et al. |

(Continued)

*Primary Examiner* — Sameh Boles
(74) *Attorney, Agent, or Firm* — Locke Lord LLP; Scott D. Wofsy; Arpita G. Buesing

(57) ABSTRACT

A bone plate assembly is disclosed which includes at least one plate segment having at least one aperture extending therethrough for receiving a head portion of a bone screw, and a structure supported by the plate segment and intersecting the aperture for retaining the head portion of the bone screw with respect to the plate segment.

8 Claims, 58 Drawing Sheets

(56) References Cited

U.S. PATENT DOCUMENTS

| | | |
|---|---|---|
| 5,941,881 A | 8/1999 | Barnes |
| 6,017,345 A | 1/2000 | Richelsoph |
| 6,066,141 A | 5/2000 | Dall et al. |
| 6,093,201 A | 7/2000 | Cooper et al. |
| 6,152,927 A | 11/2000 | Farris et al. |
| 6,193,721 B1 | 2/2001 | Michelson |
| 6,224,602 B1 | 5/2001 | Hayes |
| 6,258,089 B1 | 7/2001 | Campbell et al. |
| 6,261,291 B1 | 7/2001 | Talaber et al. |
| 6,293,949 B1 | 9/2001 | Justis et al. |
| D449,692 S | 10/2001 | Michelson |
| 6,331,179 B1 | 12/2001 | Freid et al. |
| 6,336,930 B1 | 1/2002 | Stalcup et al. |
| 6,402,756 B1 | 6/2002 | Ralph et al. |
| 6,413,259 B1 | 7/2002 | Lyons et al. |
| 6,599,290 B2 | 7/2003 | Bailey et al. |
| 6,626,907 B2 | 9/2003 | Campbell et al. |
| 6,626,944 B1 | 9/2003 | Taylor |
| 6,669,700 B1 | 12/2003 | Farris et al. |
| 6,730,127 B2 | 5/2004 | Michelson |
| 6,945,973 B2 | 9/2005 | Bray |
| 6,949,123 B2 | 9/2005 | Reiley |
| 7,033,377 B2 | 4/2006 | Miller, III |
| 7,229,444 B2 | 6/2007 | Boyd |
| 7,255,698 B2 | 8/2007 | Michelson |
| 7,276,070 B2 | 10/2007 | Muckter |
| 8,262,711 B2 | 9/2012 | Hess |

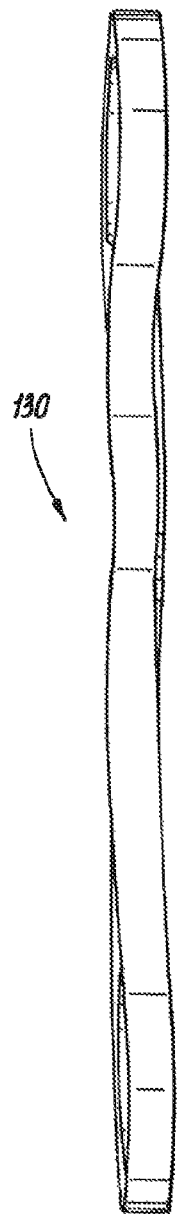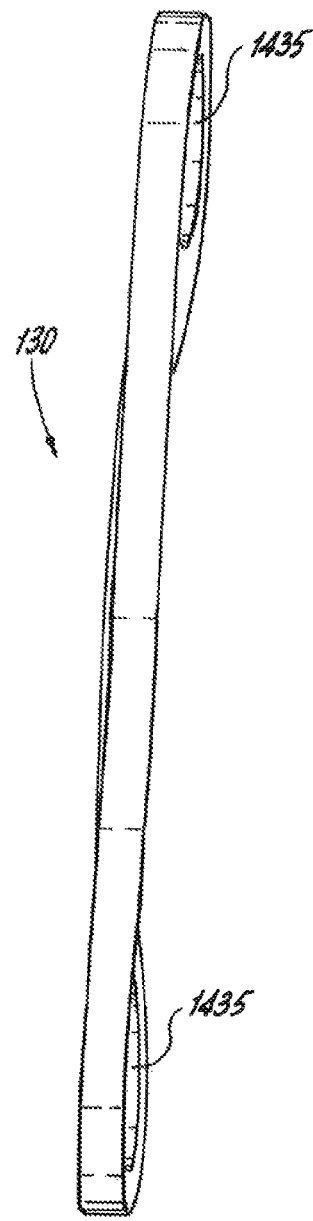
Fig. 15E
Fig. 15F

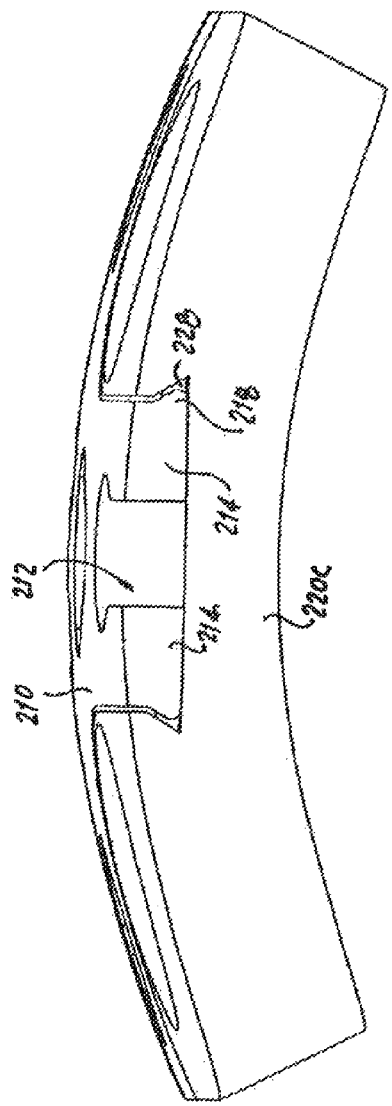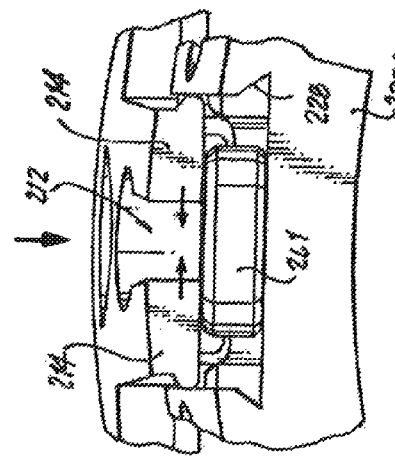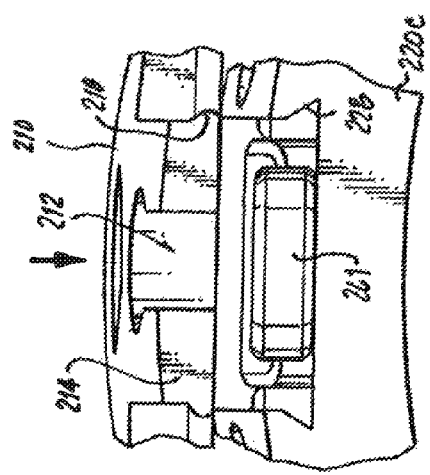

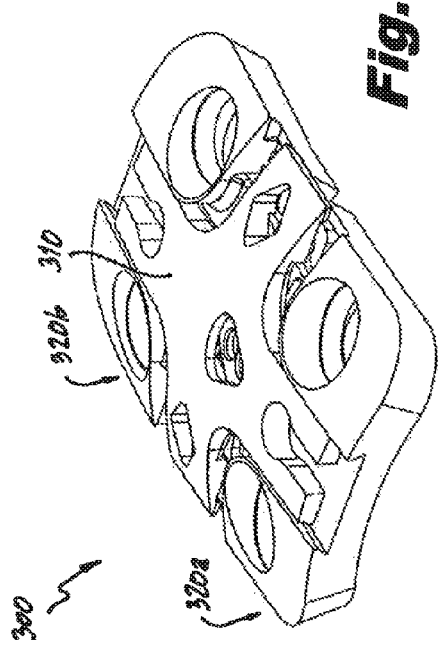
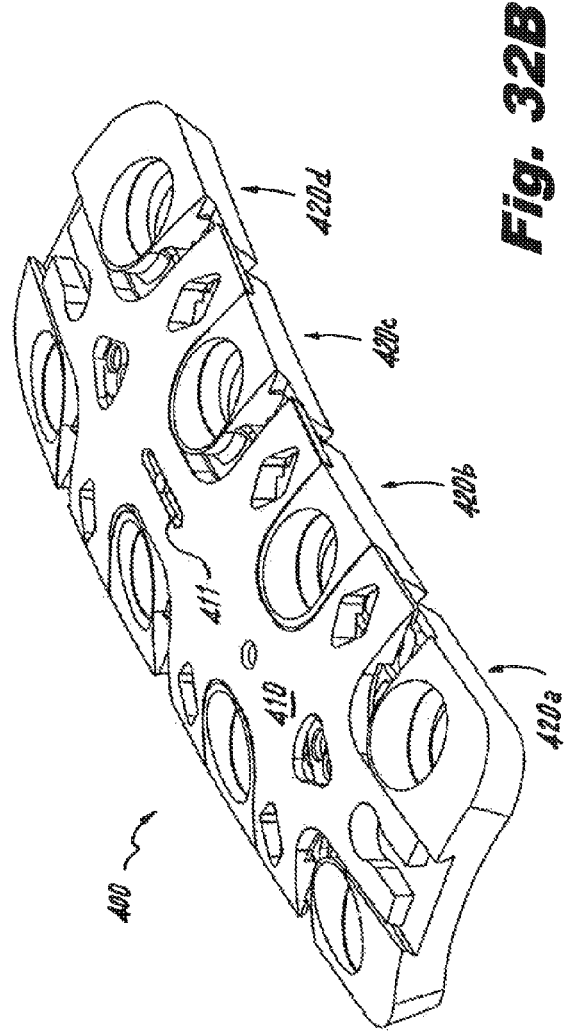

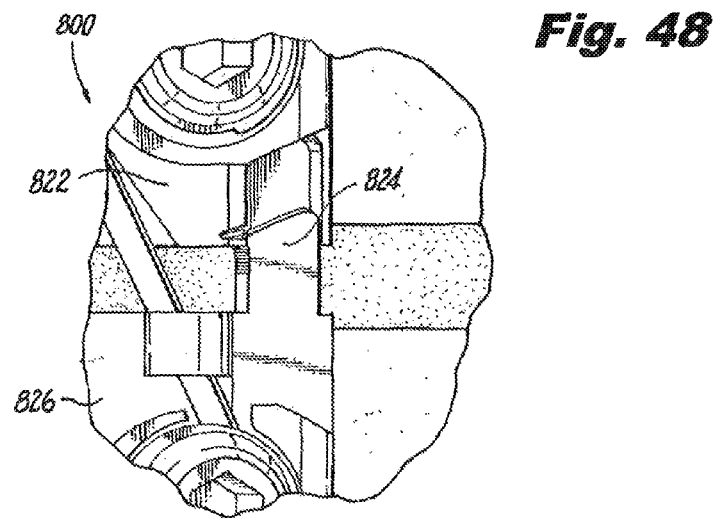
Fig. 48
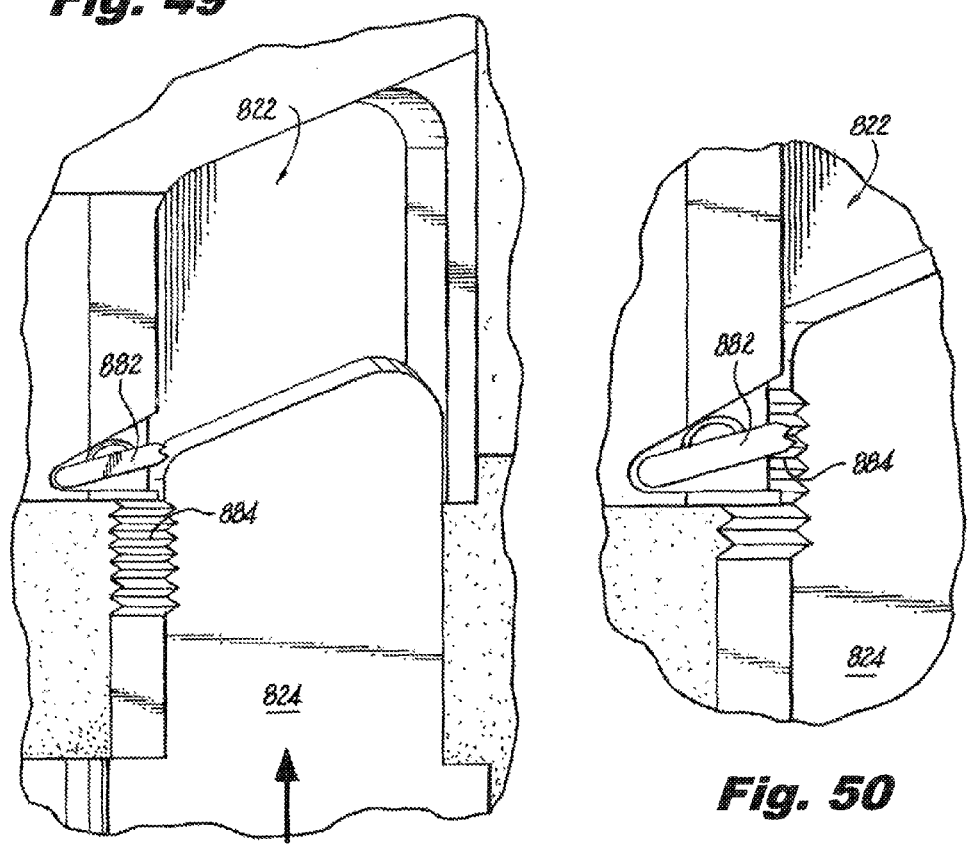
Fig. 49
Fig. 50

Fig. 54
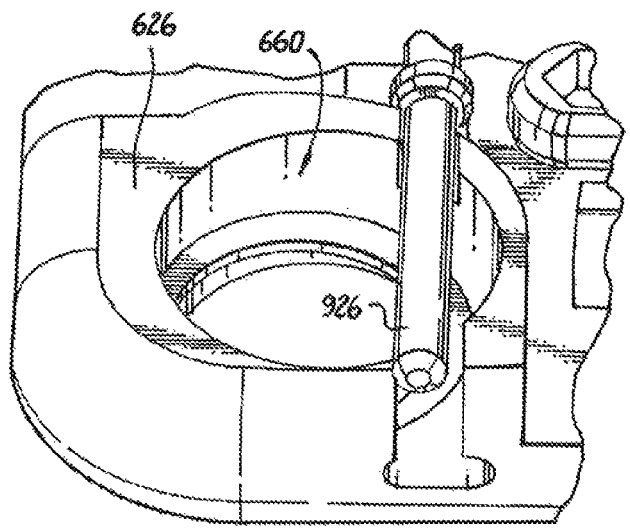
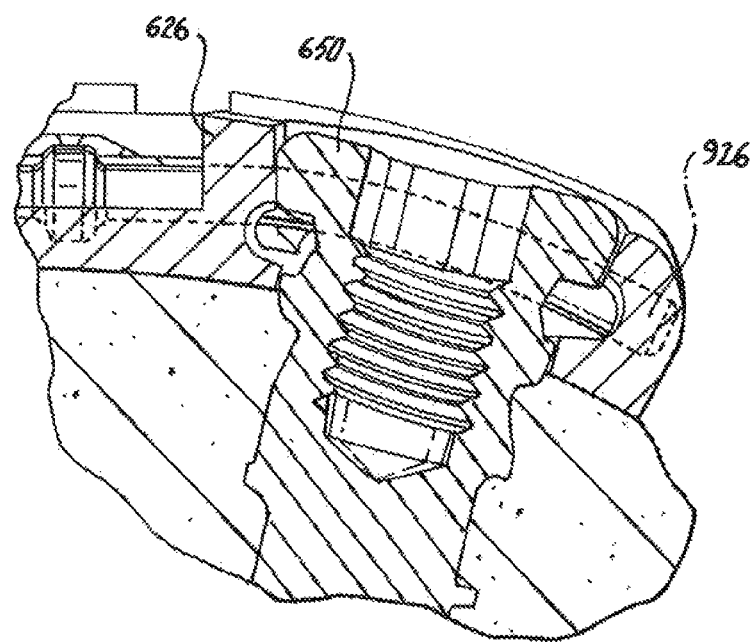
Fig. 55

Force

BONE PLATE ASSEMBLY WITH PLATES THAT RATCHET TOGETHER

CROSS-REFERENCE TO RELATED APPLICATIONS

This application is a continuation-in-part of U.S. patent application Ser. No. 12/724,420, filed Mar. 15, 2010, which claims the benefit of priority to U.S. Provisional Patent Application Ser. No. 61/160,154, filed Mar. 13, 2009, which application is incorporated herein by reference in its entirety.

BACKGROUND OF THE INVENTION

1. Field of the Invention

The present invention relates to implantable orthopedic appliances, and more particularly, to a dynamic bone plate assembly and to structure associated with the bone plate assembly for retaining bone screws associated therewith.

2. Description of the Related Art

A variety of implantable orthopedic devices are known in the art for assisting recovery following trauma or injury. Of such devices, many are directed to relatively rigid devices that force substantial load transfer from the anatomical structure, for example, from the vertebral column. Applicant recognizes that such load transfer inhibits desirable loading of the anatomical structure. In the case of bony tissue, insufficient loading will inhibit, reduce or prevent ossification of the structure, the concept of which is described by and known as "Wolff's Law."

Accordingly, Applicant recognizes that it is desirable to provide orthopedic appliances that provide for controlled load sharing, while providing support necessary to prevent damage to a bone graft and/or other anatomical structure, to allow for healing. Applicant also recognizes that it is desirable to provide orthopedic appliances that are versatile and can provide adaptability to a variety of situations. Applicant further recognizes that it is desirable to provide at least one locking feature to inhibit unintentional backing out of fasteners, such as bone screws. The present invention provides solutions for the foregoing.

SUMMARY OF THE INVENTION

In accordance with one aspect of the invention, a vertebral column construct for stabilizing a segment of a vertebral column is provided, having a first plate segment, a second plate segment connected to the first plate segment, and a spring connected between adjacent plate segments. An engagement member connected between the first and second plate segments can also be provided. Alternatively, the separate engagement member can be omitted if sufficient stability is otherwise provided, such as by the spring or another element.

The spring can be adapted and configured to provide a predetermined preload between the first and second plate segments. Accordingly, the spring can be shaped, dimensioned and formed from a material appropriate to achieve the predetermined preload, in combination with other components of the construct. Such a preload can advantageously enhance fusion across a bone graft Alternatively, the spring can be adapted and configured to resist, by a predetermined degree, loading between the first and second plate segments.

A cam can be provided on one of the first and second plate segments, and be moveable between engagement with cam surface in connection with the other of the first and second plate segments, and disengagement therefrom, wherein engagement between the cam and the cam surface prevents dynamic loading of the spinal segment, between the first and second plates.

The cam can be configured such that the position of the cam determines whether the preload exerted by the spring is transferred through the construct or transferred to the segment of the vertebral column to which the construct is attached. The cam can be adapted and configured to adjust preload applied between segments, by adjusting tension in the spring. The spring can be an arcuately bent rod or bar. The spring can be made from a shape memory alloy. The spring can be engaged with grooves in one of the plate segments, the grooves being configured such that outward application of force by the spring is resolved as a net axial contractive force between the first and second plate segments.

A common upper plate can be provided, and connected to the first and second plate segments. The upper plate and at least one of the first and second plate segments can be adapted and configured for a substantially linearly translatable connection therebetween. The upper plate and slideably connected bottom plate segment can be connected by a mechanical interlock. The mechanical interlock can include a dovetail or a pin and slot configuration.

A third plate segment can be provided and connected to at least one of the first and second plate segments by a spring, and optionally an engagement member. Fourth, fifth, sixth and subsequent plate segments can also be provided.

In accordance with the invention, at least two plate segments can be provided, and the construct can be adapted and configured such that a connection spanned between first and second plate segments is selectable between static and dynamic configurations. In accordance with the invention, at least three plate segments can be provided, spanning two connections, respectively, and the construct can be adapted and configured such that each of the two connections spanned is selectable between static and dynamic configurations.

In accordance with another aspect of the invention, a vertebral column plate system construct for stabilizing a segment of a vertebral column is provided having a first plate segment, a second plate segment connected to the first plate segment, a spring element connected between adjacent plate segments, adapted and configured for providing a predetermined preload between adjacent plate segments, to enhance spinal fusion, an upper plate connected to the first and second plate segments, and a cam provided on one of the first and second plate segments, moveable between engagement with cam surface in connection with the other of the first and second plate segments, and disengagement therefrom, wherein engagement between the cam and the cam surface prevents dynamic loading of the spinal segment, between the first and second plates. Further, an engagement member connected between adjacent plate segments can be provided.

In accordance with the invention, the cam surface can be provided on the other of the first and second plates. Alternatively, the cam surface can be on the upper plate. In such an arrangement, the upper plate and the other of the first and second plates can be substantially rigidly connected to one another.

In accordance with a further aspect of the invention, a method of implanting a vertebral column construct on a spinal segment is provided, the method including, in any order, securing each of a plurality of plates of the construct to respective vertebrae, determining whether to apply a preload between first and second levels of vertebrae, and applying a first preload between said first and second levels of vertebrae.

The step of applying the first preload can include rotating a first cam of the dynamic vertebral column construct in a first direction.

The method can further include the steps of evaluating efficacy of the first preload, and applying a second preload, in place of the first preload, between said first and second levels of vertebrae, the second preload being different from the first preload. The second preload being greater than the first preload. Alternatively, the second preload can be less than the first preload.

The step of applying a second preload can include rotating a first cam in a second direction, different from the first direction. The method can further include the steps of determining whether to apply a preload between first and second levels of vertebrae, and applying a third preload between said second and third levels of vertebrae. The step of applying the third preload can include rotating a second cam of the dynamic vertebral column construct in a first direction.

The method can further comprises the steps of evaluating efficacy of the third preload, and applying a fourth preload, in place of the third preload, between said second and third levels of vertebrae, the fourth preload being different from the third preload. The step of applying the fourth preload can include rotating a second cam in a second direction, different from the first direction.

Constructs in accordance with the invention, additionally or alternatively, can be configured to provide a predetermined amount of resistance to contraction and/or to bending between adjacent plate segments thereby allowing for a predetermined amount of load sharing between the construct and the vertebral column segment.

In accordance with the invention, the engagement members, if provided, can be symmetrically arranged in the construct with respect to a longitudinal axis thereof. Moreover, two laterally opposed, springs can be provided in the construct and can be arranged substantially symmetrically with respect to a longitudinal axis of the construct.

In accordance with the invention, a plurality of screws can be provided for engaging the construct to the vertebral column segment. The screws can include a slot or other feature for accepting an engagement element for inhibiting unintentional backout of the screws. In accordance with the invention, one or more of the plate segments can be embodied so as to include respective upper and lower portions.

A plurality of spring elements can be provided for assembly with plate segments, the spring elements being provided in a range of stiffnesses, allowing for selectability of contractive force, or preload, of the construct and/or selectability of resistance to contraction, and/or bending stiffness of the construct, if so-embodied. The engaging element can be received in a corresponding recess provided in each plate segment connected by the engagement member.

In accordance with an embodiment of the subject invention, there is provided a bone plate assembly that includes at least one plate segment having at least one aperture extending therethrough for receiving a head portion of a bone screw, and means supported by the plate segment and extending into or otherwise intersecting the aperture for retaining the head portion of the bone screw with respect to the plate segment. Preferably, the means for retaining the head portion of the bone screw is defined by a spring rod. The spring rod may be generally U-shaped or elongated. The elongated spring rod may include a central mounting portion flanked by at least one curved screw head retention portion. Preferably, the plate segment includes an upstanding yoke for supporting a central mounting portion of the spring rod.

It is envisioned that the aperture in the bone plate segment is defined at least in part by an upstanding peripheral wall, and a window is formed in the wall for accommodating passage of a retention portion of the spring rod. The assembly further includes a bone screw, and the head portion of the bone screw includes a reception groove for engagement by a retention portion of the spring rod. Alternatively, the head portion of the bone screw has an upper reception surface for engagement by a retention portion of the spring rod.

The subject invention is also directed to a dynamic bone plate assembly that includes a plurality of interconnected plate segment each having a pair of apertures extending therethrough for receiving a head portion of a bone screw, and means supported by each plate segment and extending into or otherwise intersecting the apertures associated therewith for retaining the head portion of the bone screws with respect to the plate segment. Preferably, the dynamic bone plate assembly includes a pair of outer plate segments and a central plate segment. In one version of the dynamic plate assembly, the means for retaining the head portion of the bone screws in each outer plate segment is a generally U-shaped spring rod, and the means for retaining the head portion of the bone screws in the central plate segment is an elongated spring rod.

In another version of the dynamic plate assembly, the means for retaining the head portion of the bone screws in the central plate segment is an elongated spring rod having a central mounting portion flanked by oppositely curved screw head retention portions. In yet another version of the dynamic bone plate assembly, the means for retaining the head portion of the bone screws in each of the three plate segments is an elongated spring rod. In still another embodiment of the subject invention, the means for retaining the head portion of the bone screw is defined by a retention clip that extends into the aperture through a side wall of the plate segment. In either of these embodiments, the retaining rods can have circular or square cross-sections, and can be formed by any conventional metal forming process.

The subject invention is also directed to a dynamic bone plate assembly that includes at least first and second plate segments adapted and configured for movement relative to one another from a spaced apart position and an approximated position, and ratchet means for allowing the first and second plate segments to move from the approximated position while preventing the first and second plate segments from moving toward a spaced apart position. Preferably, the ratchet means includes a ratcheting pawl member operatively associated with the first plate segment and a rack of ratchet teeth provided on the second plate segment for interacting with the pawl member.

It is to be understood that both the foregoing general description and the following detailed description are exemplary and are intended to provide further explanation of the invention claimed.

BRIEF DESCRIPTION OF THE DRAWINGS

The accompanying drawings, which are incorporated in and constitute part of this specification, are included to illustrate and provide a further understanding of the systems, devices, kits and related methods of the invention. Together with the description, the drawings serve to explain the principles of the invention, wherein:

FIG. 15E is a left side view of the spring member of FIG. 15A;

FIG. 15F is a right side view of the spring member of FIG. 15A;

FIG. 16-29 illustrate various views of another exemplary embodiment of a dynamic vertebral column plate system in accordance with the invention, having arcuately bent rod or bar-shaped springs and an integral cam element;

FIG. 16 is an isometric view of the plate construct in accordance with this embodiment, shown in an expanded condition;

FIG. 17 is a side view of the plate construct, shown in an expanded condition;

FIG. 18 is an isometric view of the plate construct, shown in a contracted condition;

FIG. 19 is a side view of the plate construct, shown in a contracted condition;

FIG. 20 is a bottom isometric view of the plate construct, shown in an expanded condition;

FIG. 21 is a bottom isometric view of the plate construct, shown in a contracted condition;

FIGS. 22A-C are end views of the plate construct, illustrating engaging steps between an upper plate and a lower end plate segment;

FIG. 23 is a partly exploded isometric view of the plate construct, illustrating internal components thereof and a tool for operating a cam thereof;

FIG. 24 is a bottom isometric of the upper plate of plate construct;

FIG. 25 is an exploded view of the internal components of the plate construct;

FIG. 26 is an isometric view of the plate construct, shown in an expanded condition with both cams rotated out of engagement with opposing recesses therefor, shown with the upper plate removed for visibility;

FIG. 27 is top view of an end portion of the plate construct with the illustrated cam held in an opposing recess, maintaining the expanded condition of the plate, shown with the upper plate removed for visibility;

FIG. 28 is an isometric view of the plate construct with both cams rotated out of engagement with the opposing recesses therefor, shown in a contracted condition, with the upper plate removed for visibility;

FIG. 29 is top view of an end portion of the plate construct with the illustrated cam rotated out of engagement with the opposing recesses therefor, maintaining the expanded condition of the plate, shown in a contracted condition, with the upper plate removed for visibility;

FIG. 30A illustrates the construct during insertion of a final screw for engaging the attached vertebral segment;

FIG. 30B illustrates the construct during rotation of a cam thereof, with a tool therefor;

FIG. 30C illustrates the construct following attachment to the vertebral segment and rotation of both cams from the opposing recesses therefor, shown with the upper plate removed for visibility;

FIG. 32A is an isometric view of a dynamic vertebral column plate system construct in accordance with the invention, having two levels of plate segments;

FIG. 32B is an isometric view of a dynamic vertebral column plate system construct in accordance with the invention, having four levels of plate segments;

FIG. 33 is an isometric view of the construct of this embodiment, shown in an expanded condition;

FIG. 34 is an isometric view of the construct of this embodiment, shown in a contracted condition;

FIG. 35 is an isometric view of the construct of this embodiment, shown in an expanded condition, with the upper plate removed for visibility;

FIG. 36 is a bottom isometric view of the upper plate of this embodiment of the construct;

FIG. 37 is a top view of the construct of this embodiment shown in an expanded condition, with the upper plate removed for visibility;

FIG. 38 is a top view of the construct of this embodiment shown in a contracted condition, with the cams in one position for applying a corresponding preload to a spinal segment, and with the upper plate removed for visibility;

FIG. 39 is a top view of the construct of this embodiment shown in a contracted condition with the cams in another position (as compared with FIG. 38), for applying a different corresponding preload to a spinal segment, also shown with the upper plate removed for visibility;

FIG. 48 is a plan view of a section of the spinal plate assembly of the subject invention, illustrating a ratchet mechanism that allows two plate segments to move toward one another to shorten the length of the plate assembly, while preventing the two segments from moving apart from one another;

FIG. 49 is an enlarged localized view of the ratchet mechanism shown in FIG. 48 when the plate segments are spaced apart from one another; and FIG. 50 is a localized view of the ratchet mechanism showing the plate segments in an approximated position, in which the ratchet arm prevents the plate segments from moving apart from one another;

FIG. 54 is a localized view of section of the spinal plate assembly shown in FIG. 53 illustrating the position of the spring rod in the absence of a bone screw;

FIG. 55 is a cross-sectional view taken along line 55-55 of FIG. 53 illustrating the engagement of a spring rod in the retention channel of the head of a bone screw;

DETAILED DESCRIPTION OF THE PREFERRED EMBODIMENTS

Reference will now be made in detail to preferred embodiments of the invention, an example of which is illustrated in the accompanying drawings.

The devices and methods presented herein may be used for stabilization of a segment of the vertebral column during spinal fusion following surgery.

Figure 1A:
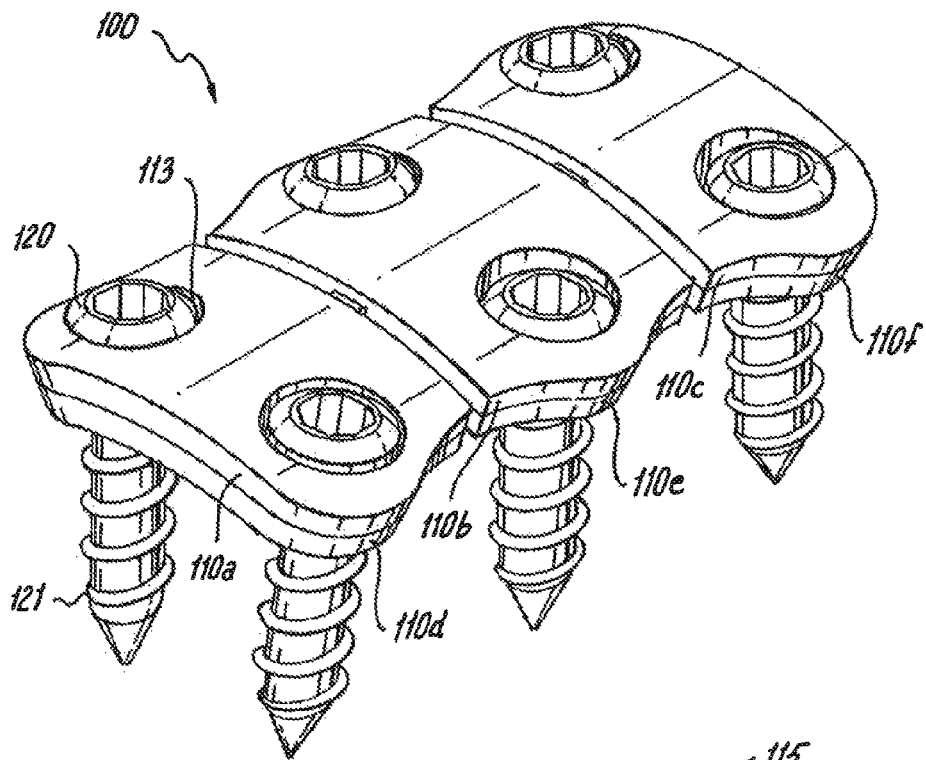
FIGS. 1A and 1B are, respectively, an isometric line drawing and an isometric rendering showing internal structure, of a representative embodiment of a dynamic vertebral column plate system and accompanying screws, in accordance with the present invention, wherein the vertebral column plate system is shown in an extended state.
Figure 1B:
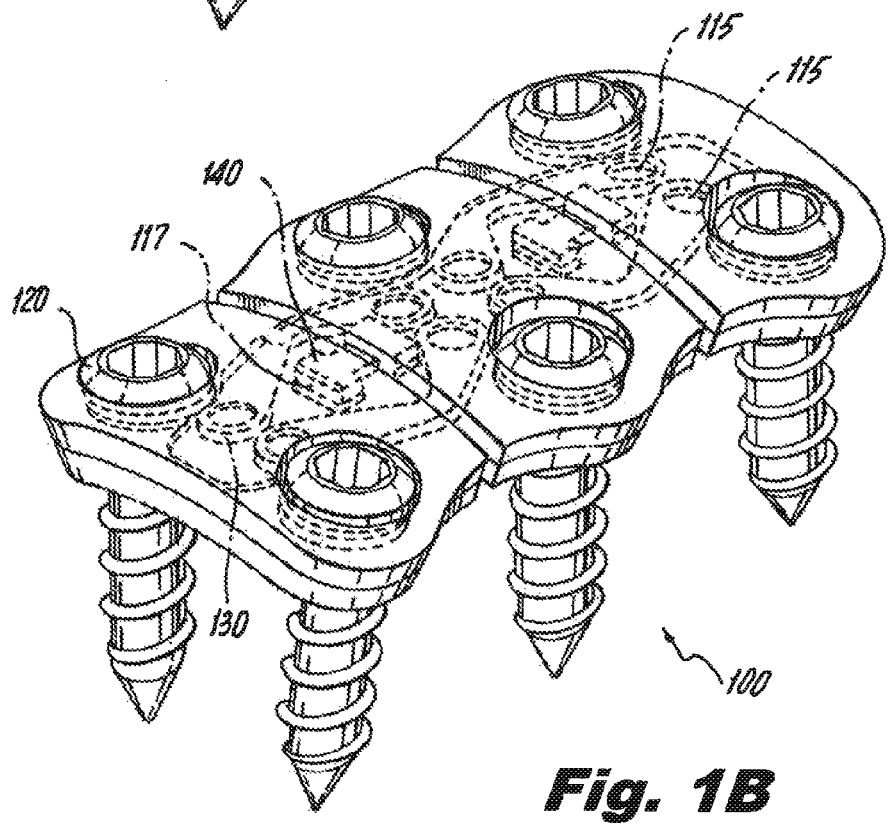
Figure 1C:
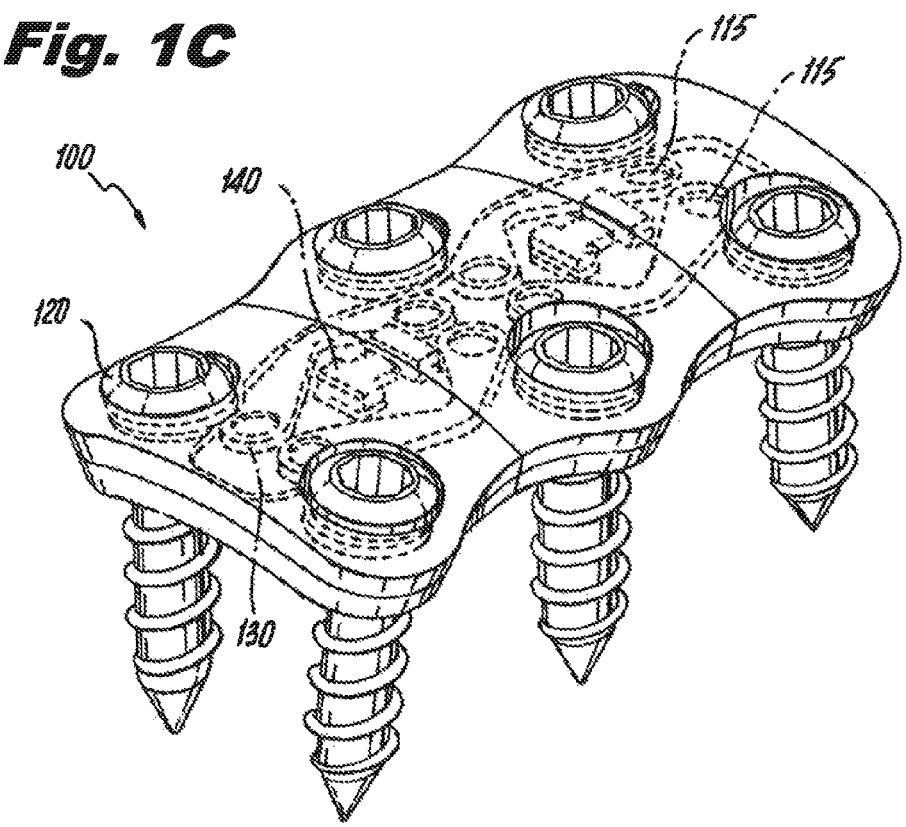
FIGS. 1C and 1D are, respectively, an isometric rendering showing internal structure and an isometric line drawing of a representative embodiment of a dynamic vertebral column plate system and accompanying screws, in accordance with the present invention, wherein the vertebral column plate system is shown in a collapsed state.
Figure 1D:
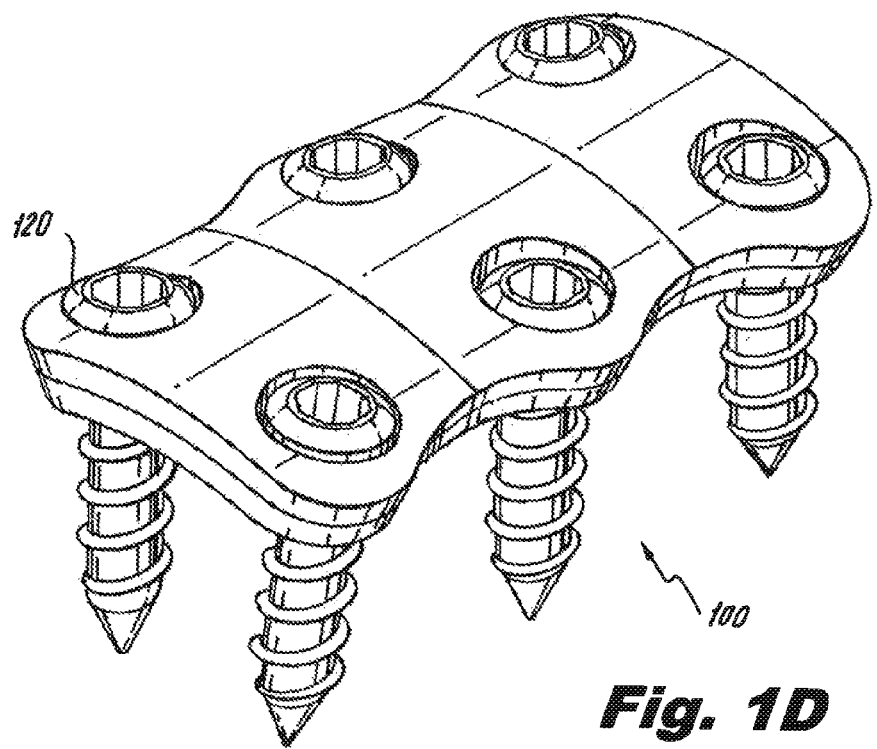

With reference to the figures and as seen, for example, in FIGS. 1A and 1B, a dynamic vertebral column plate system for stabilizing a segment of a vertebral column is able to be assembled into a plate construct 100 for attachment to a vertebral column segment. Such constructs can be provided to a user (such as a surgeon) already assembled, or can be assembled by the user, for example. The plate system includes a first end plate segment, having upper and lower portions 110a and 120a, a second end plate segment having upper and lower portions 110c and 120c connected to and arranged opposite the first plate segment. As illustrated, an intermediate plate segment having upper and lower portions 110b and 120b can be provided. In accordance with further aspects of the invention, additional intermediate plate segments can additionally be provided, yielding a total of 3, 4, 5, 6, 7, 8 or more plate segments in the construct 100 formed from the components of the subject system.

In the illustrated embodiment, an engagement member 140 and spring elements 130 are provided between and connect adjacent plate segments, forming the plate construct 100. Although one engagement member 140 and two springs 130 are illustrated between each adjacent pair of plate segments, it is to be understood that any suitable number of such elements can be provided. It is particularly conceived that two laterally opposed engagement members 140 can be additionally or alternatively provided laterally distal to the springs 130. In such an embodiment, it is conceived that it may prove necessary to provide additional material along the lateral edges of the plate segments 110, 120 to provide structural support and/or simply to provide space for holding the additional engagement members.

The springs 130 are adapted and configured to provide a predetermined amount of contractive force, or preload, of the construct 100. In accordance with alternate embodiments the springs 130 can be adapted and configured to provide a predetermined amount of bending stiffness between adjacent plate segments, thereby allowing for a predetermined amount of load sharing between the construct 100 and the vertebral column segment to which it is attached.

Figure 11A:
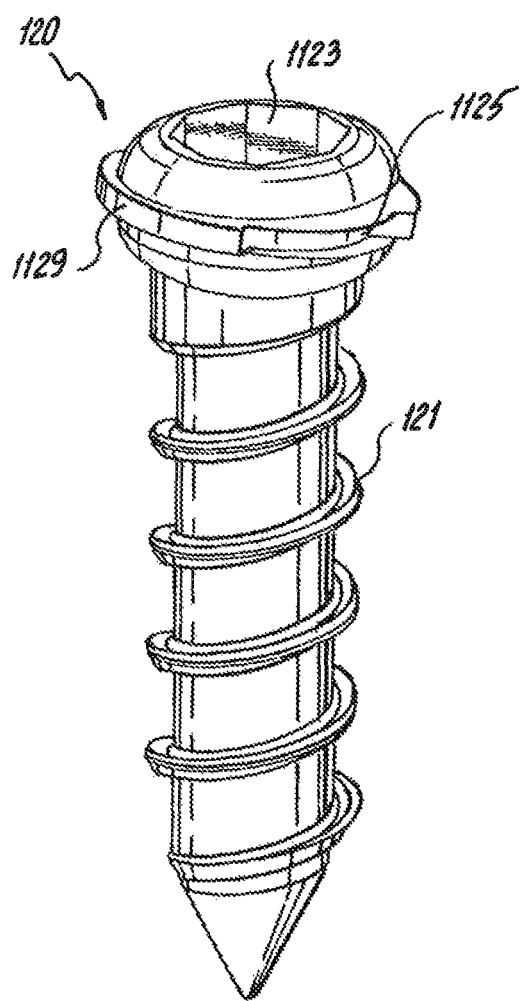
FIGS. 11A and 11B are, respectively, a line drawing and a rendering illustrating a screw and a retaining clip in accordance with the invention for use with the dynamic vertebral column plate system of FIGS. 1A and 1B.
Figure 11B:
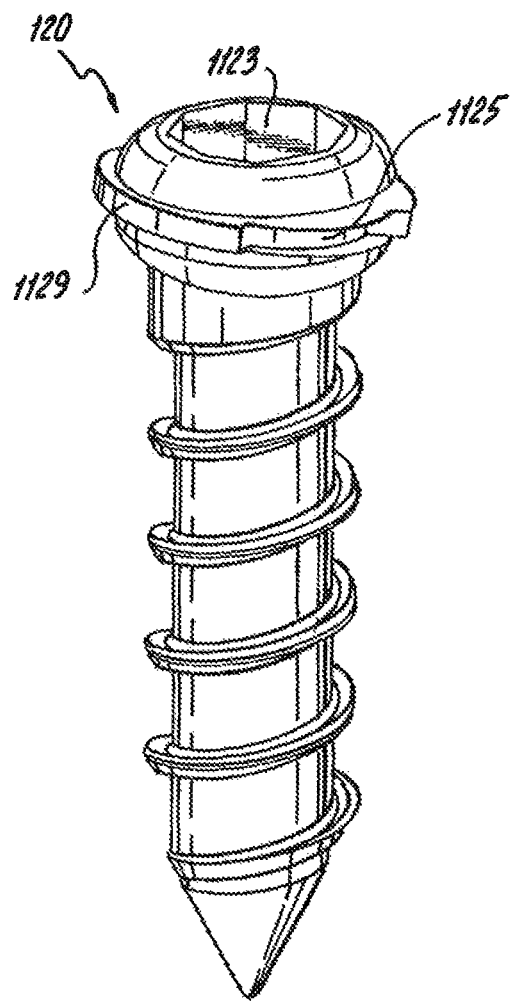
Figure 11C:
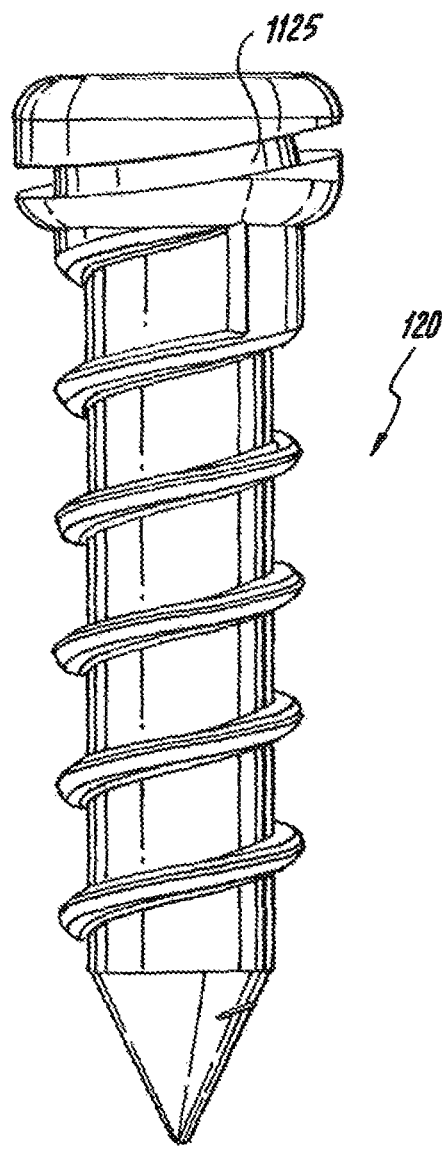
FIG. 11C is a line drawing of the screw of FIGS. 11A and 11B, shown without the retaining clip.

As can be seen in FIGS. 1A and 1B, a plurality of screws 150 are provided for anchoring the construct 100 into the bone. Apertures 113a are provided in upper plate portion 110a, 110b, 110c, in which the head of the screws 150 rest. A groove 155 is provided in the head of the screw 150 for receiving a locking element, such as the retaining clip 159, which is best seen in FIGS. 11A and 11B. The locking element can be any suitable element, including but not limited to a resilient o-ring, cir-clip, or another suitable element, such as a latching toroidal coil available from Bal Seal Engineering, Inc. of Foothill Ranch, Calif., USA. The locking element can be formed of any suitable material, such as a metal, metal alloys, an elastomeric material, silicone, polychloroprene (e.g. Neoprene), or a plastic material such as polyetheretherketone (PEEK), for example. The locking element, carried by the screw can seat in a groove provided in the construct being used.

As seen in FIG. 1B, as well as in FIGS. 1C, 8B, 9 and 10, spring engagement members or bosses 115, 125 can be provided in connection with or integrally with the plate segments, such as with upper plate portion 110a or lower plate portion 120a, respectively, for engaging the springs 130. Similarly, the engagement members 140 are secured to adjacent plates by a recess 117, 127 provided in each respective upper plate portion 110a-c and lower plate portion 120a-c. The recesses 117, 127 are shaped with a corresponding partial "I" shape to capture the engagement members 140, and to allow for axial motion between the plate portions 110, 120 and the engagement members 140. Accordingly, the transverse section of the recess 117, 127 can be deeper than that of the engagement member 140 to allow for axial motion. Moreover, it is to be understood that various shapes of engagement members 140 can be used, and are not be limited solely to the shape illustrated.

Although illustrated as independent components, it is to be understood that in alternative embodiments, engagement members 140 can be integrally formed with one plate, fitting into a corresponding recess 117, 127 in an adjacent plate. Accordingly, relative motion between plate segments is allowed, without necessitating manufacture and assembly of separate components. In line with such embodiments, it is particularly conceived that any permutation of arrangements of separate or integral engagement members 140 is possible, with any suitable number of engagement members 140 being provided between adjacent plates.

Figure 8A:
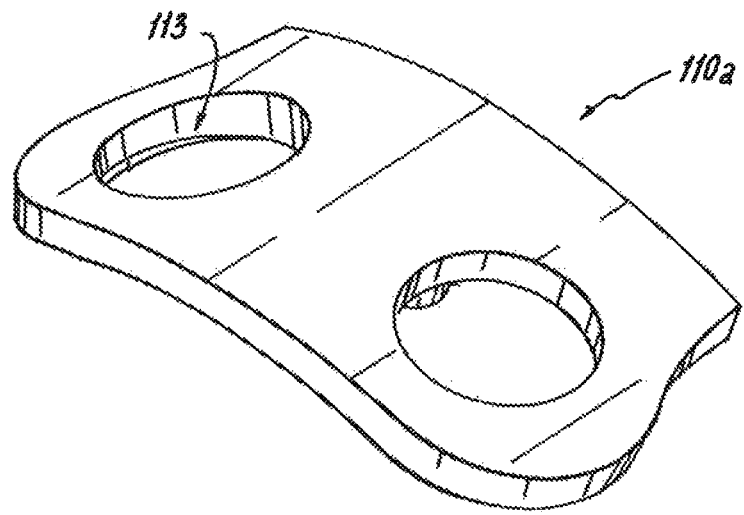
FIGS. 8A and 8B are, respectively, isometric line drawings of top and bottom surfaces of an upper plate segment of the dynamic vertebral column plate system of FIGS. 1A and 1B.
Figure 8B:
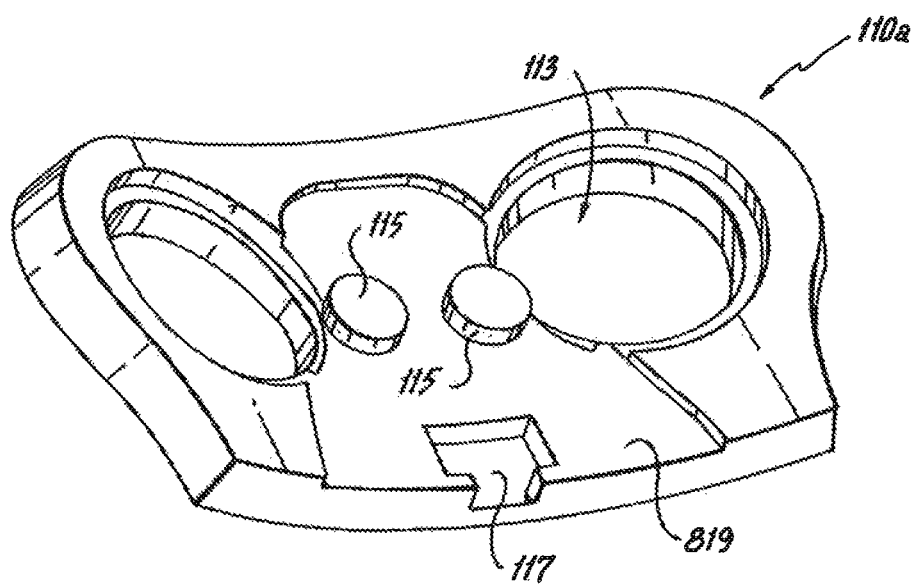

The round spring engagement members or bosses 115, 125 allow for relative movement of the springs when the construct 100 is subjected to different loading conditions, such as axial tensile or compressive forces or lateral bending (in a plane that is substantially parallel to the plate surface and parallel to the longitudinal axis of the construct, for example). Alternatively, the bosses 115, 125 can be any suitable shape, including but not limited to elliptical, oblong, polygonal (e.g., square, hexagonal). Shapes of bosses 115, 125 that inhibit rotation thereabout can enhance lateral stability of the construct 100. A relatively shallow recess 119 is provided in one or more of the upper plate portions 110a-c and lower plate portions 120a-c, as best seen in FIG. 8B. The recesses 119 are configured to provide room for elastic deformation of the springs 130 under the aforementioned axial compression and/or bending conditions.

Upper and lower portions of the plate segments, such as upper plate portion 110a and lower plate portion 120a, can be mutually secured in any suitable manner, including but not limited to welding, mechanical fasteners, solders, adhesives, epoxy materials, mechanical interlock features or the like.

Figure 2A:
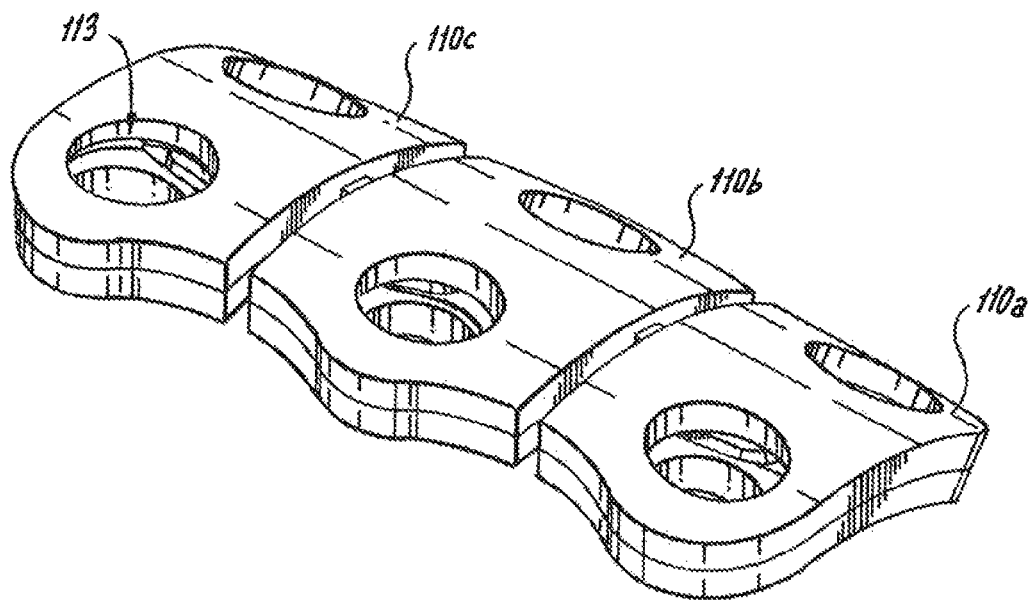
FIGS. 2A and 2B are, respectively, an isometric line drawing and an isometric rendering showing internal structure, of the dynamic vertebral column plate system of FIGS. 1A and 1B, shown without accompanying screws, in accordance with the present invention.
Figure 2B:
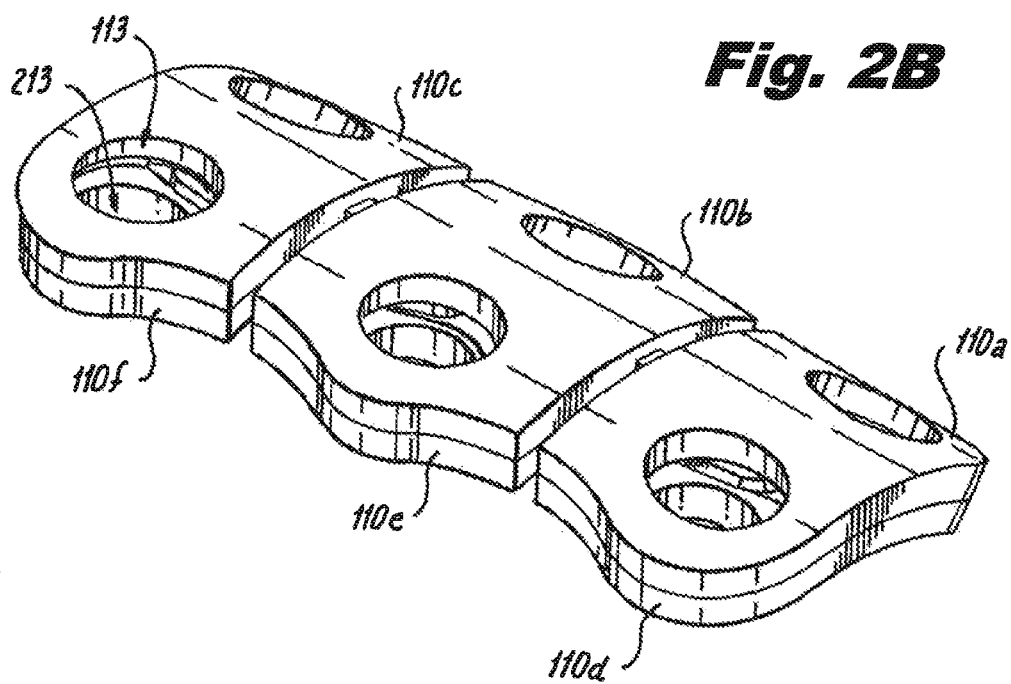
Figure 3A:
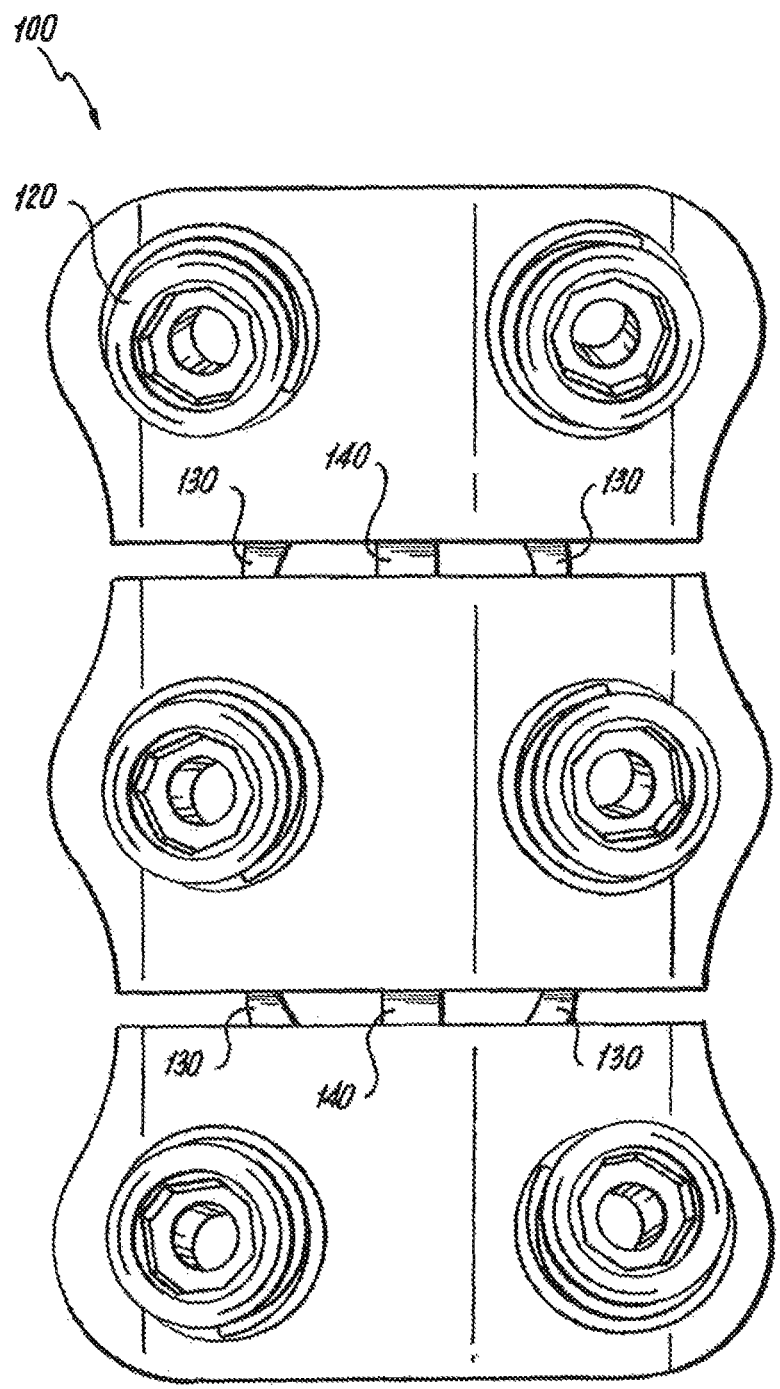
FIGS. 3A and 3B are, respectively, a top line drawing and a top rendering showing internal structure, of the dynamic vertebral column plate system of FIGS. 1A and 1B, shown with accompanying screws.
Figure 3B:
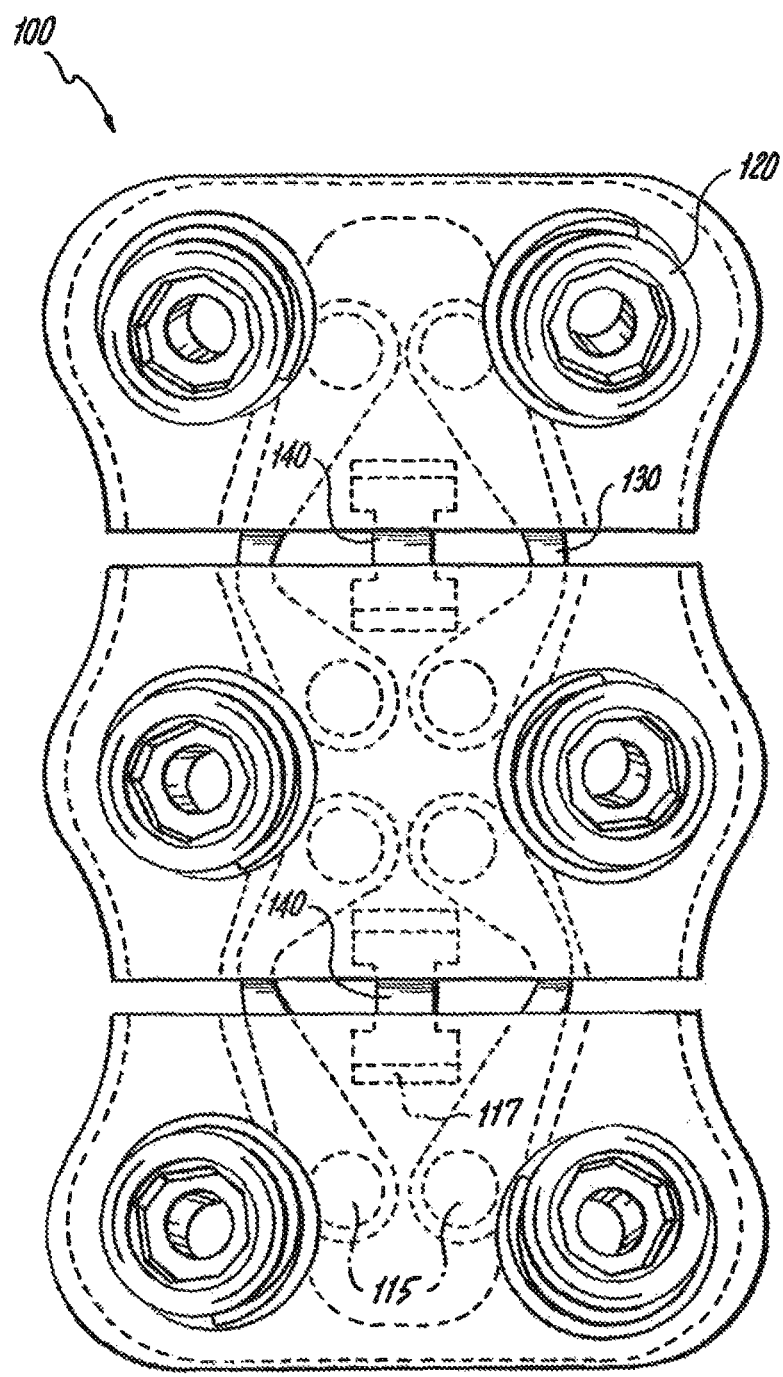
Figure 3C:
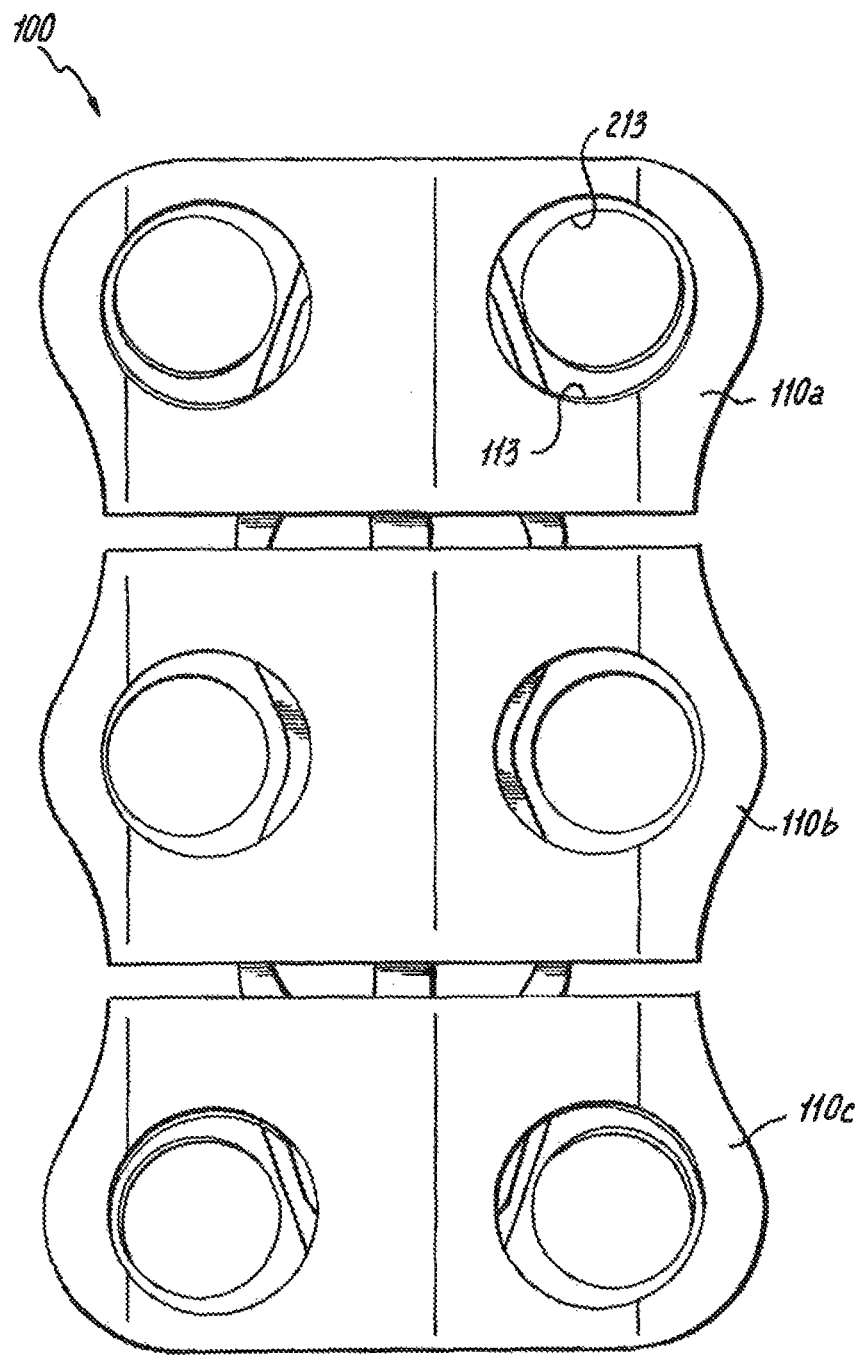
FIG. 3C is a top line drawing of the dynamic vertebral column plate system of FIGS. 1A and 1B, shown without the accompanying screws.
Figure 4A:
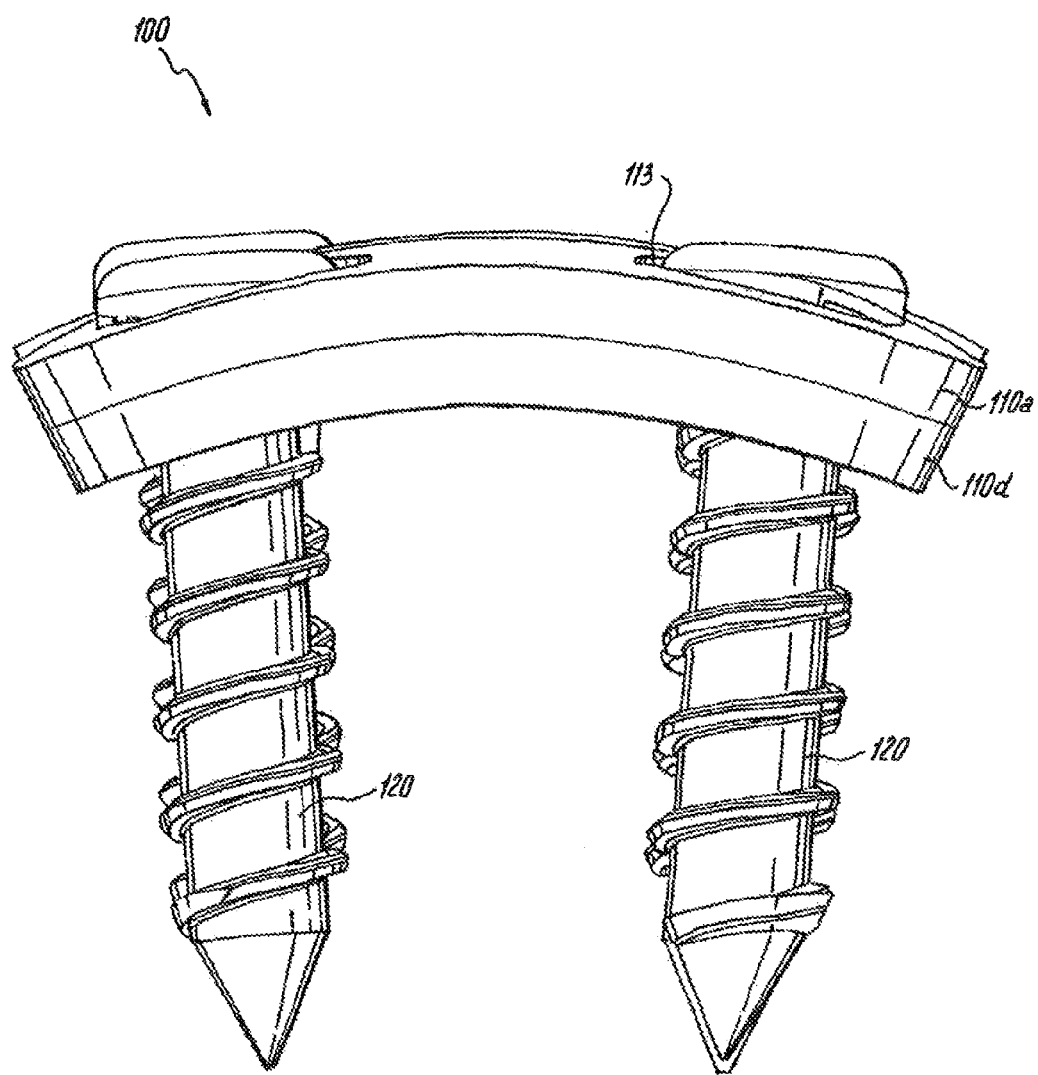
FIGS. 4A and 4B are, respectively, an end line drawing and an end rendering showing internal structure of the dynamic vertebral column plate system of FIGS. 1A and 1B, shown with accompanying screws.
Figure 4B:
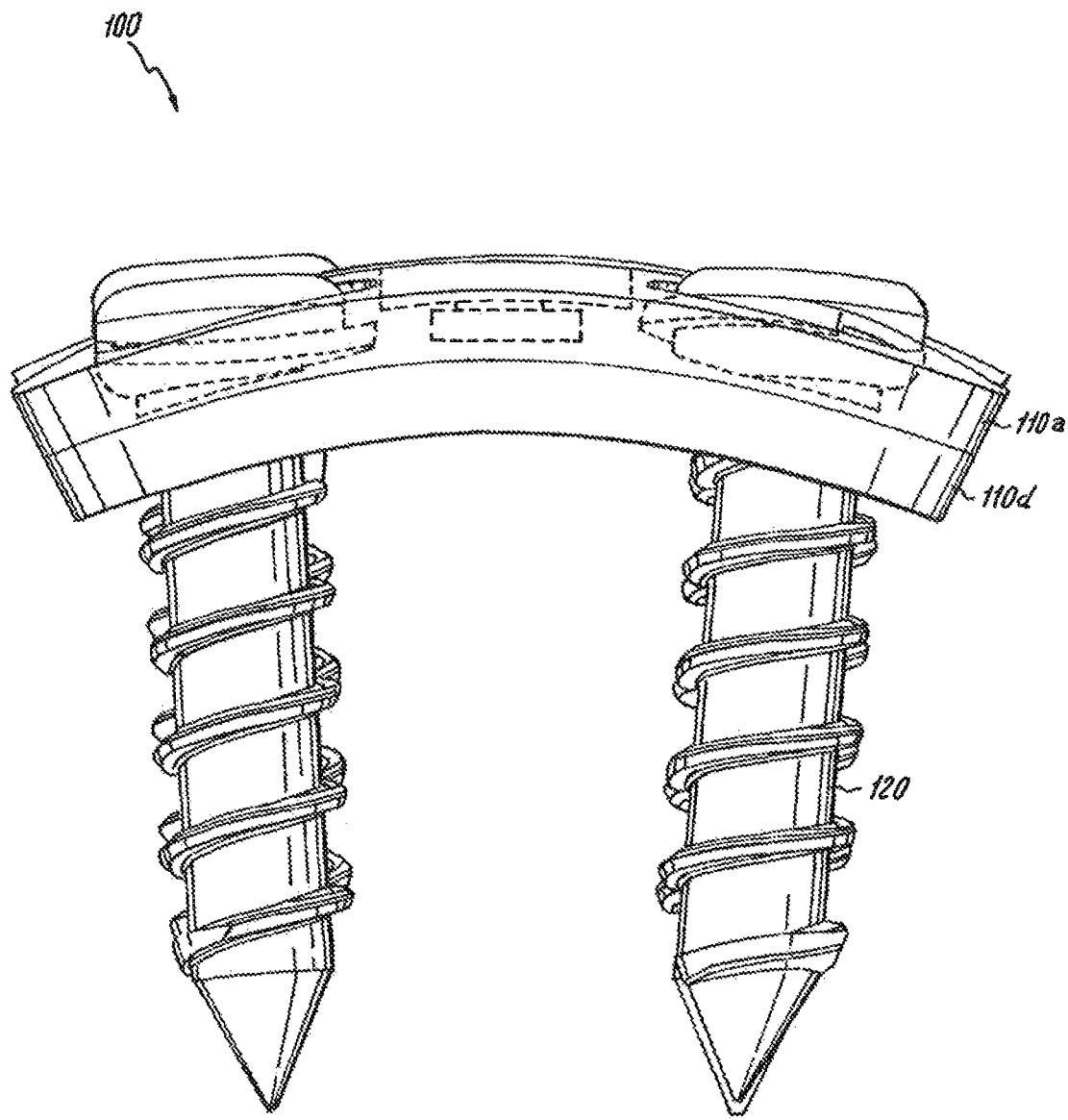
Figure 5A:
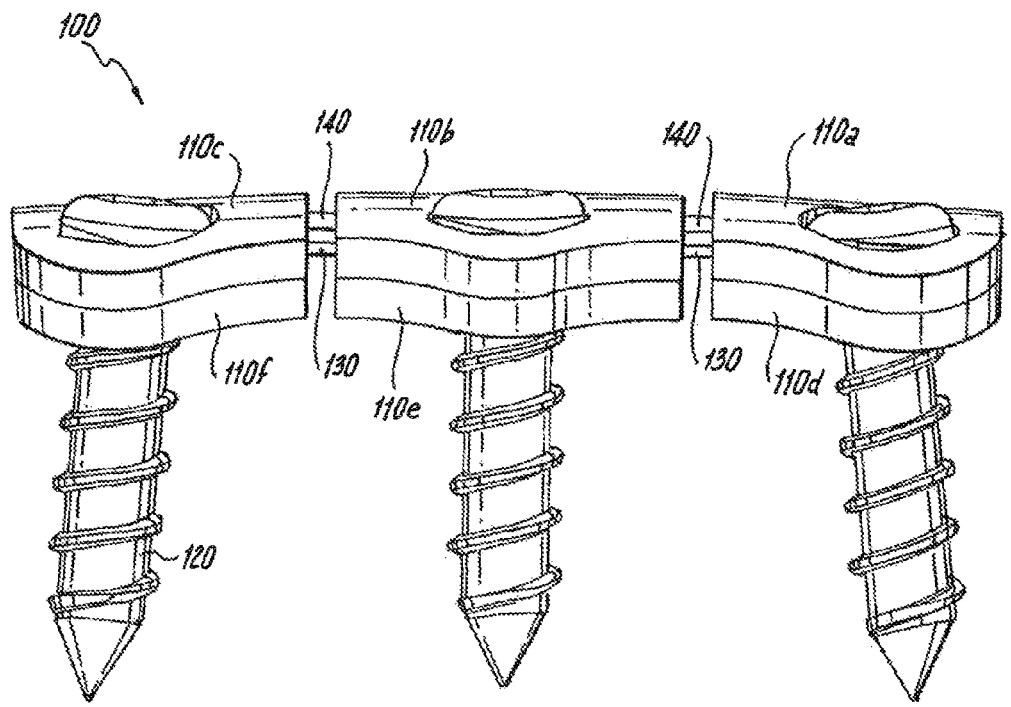
FIGS. 5A and 5B are, respectively, a side line drawing and a side rendering showing internal structure, of the dynamic vertebral column plate system of FIGS. 1A and 1B, shown with accompanying screws.
Figure 5B:
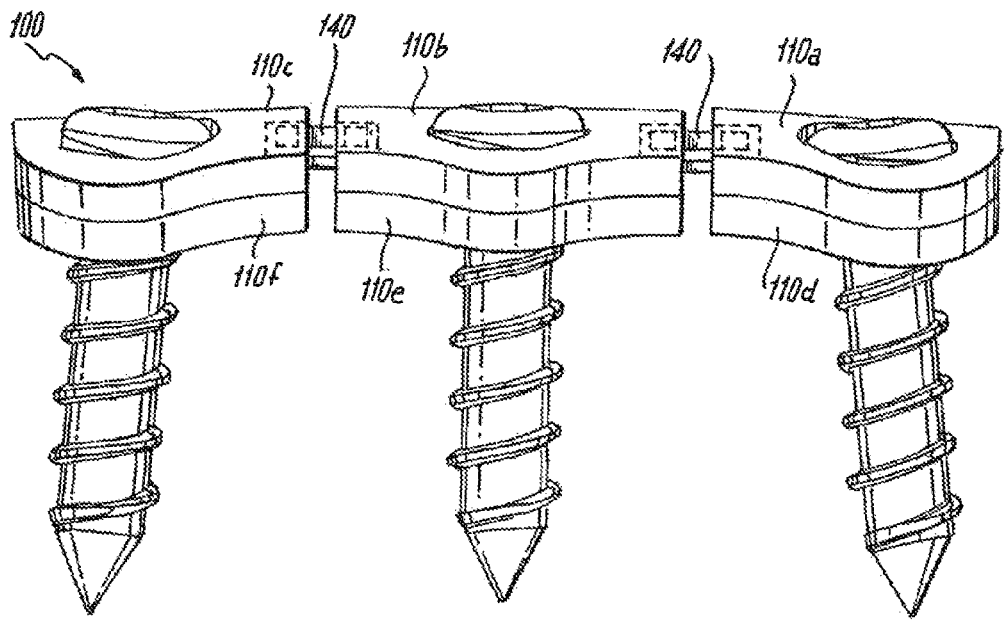

As mentioned above, FIGS. 2A and 2B are, respectively, an isometric line drawing and an isometric rendering showing internal structure of the dynamic vertebral column plate system of FIGS. 1A and 1B, shown without accompanying screws, in accordance with the present invention. FIGS. 3A and 3B are, respectively, a top line drawing and a top rendering showing internal structure of the dynamic vertebral column plate system of FIGS. 1A and 1B, shown with accompanying screws. FIG. 3C is a top line drawing of the dynamic vertebral column plate system of FIGS. 1A and 1B, shown without the accompanying screws. FIGS. 4A and 4B are, respectively, an end line drawing and an end rendering showing internal structure of the dynamic vertebral column plate system of FIGS. 1A and 1B, shown with accompanying screws. FIGS. 5A and 5B are, respectively, a side line drawing and a side rendering showing internal structure, of the dynamic vertebral column plate system of FIGS. 1A and 1B, shown with accompanying screws.

Figure 6A:
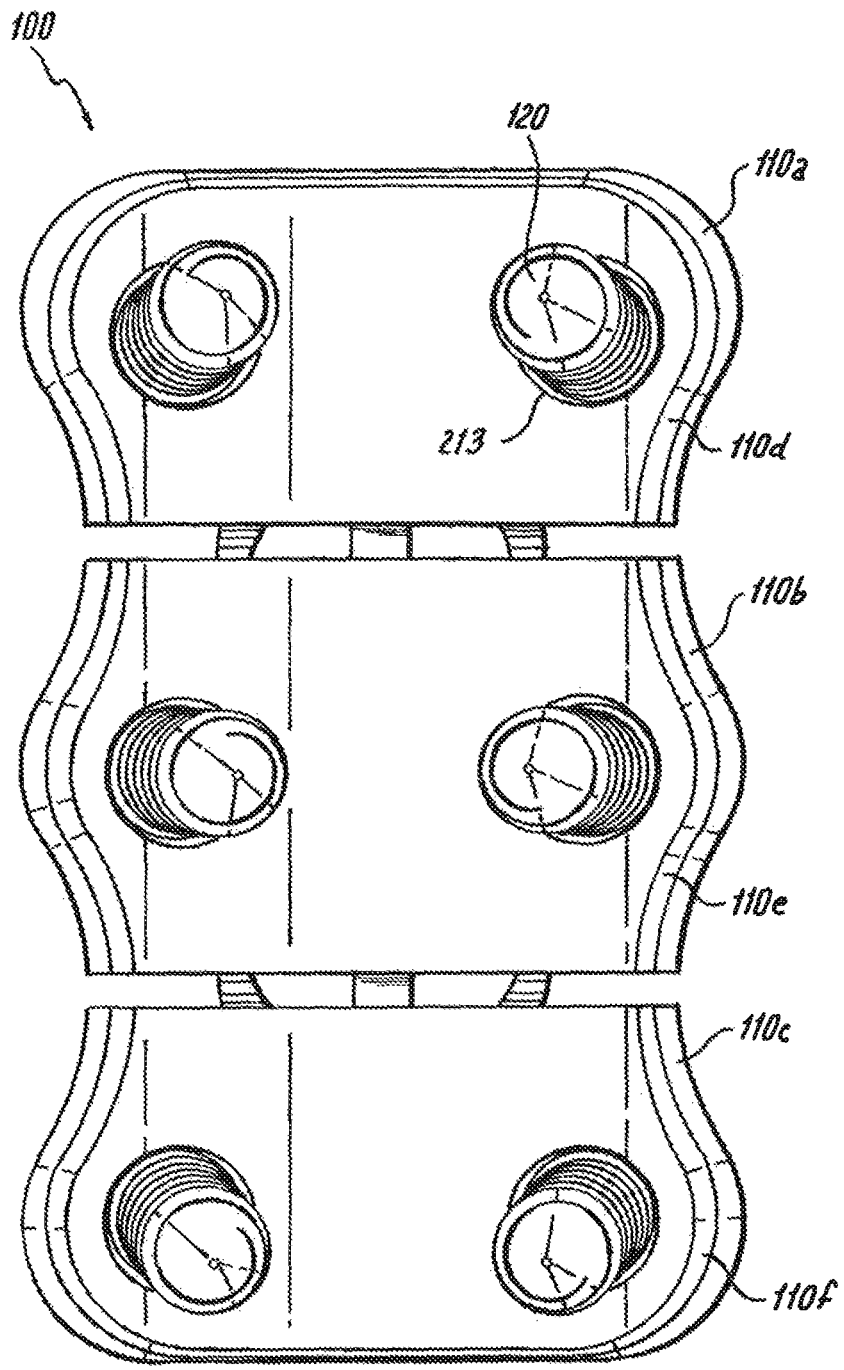
FIG. 6A is a bottom line drawing of the dynamic vertebral column plate system of FIGS. 1A and 1B, shown with accompanying screws.
Figure 6B:
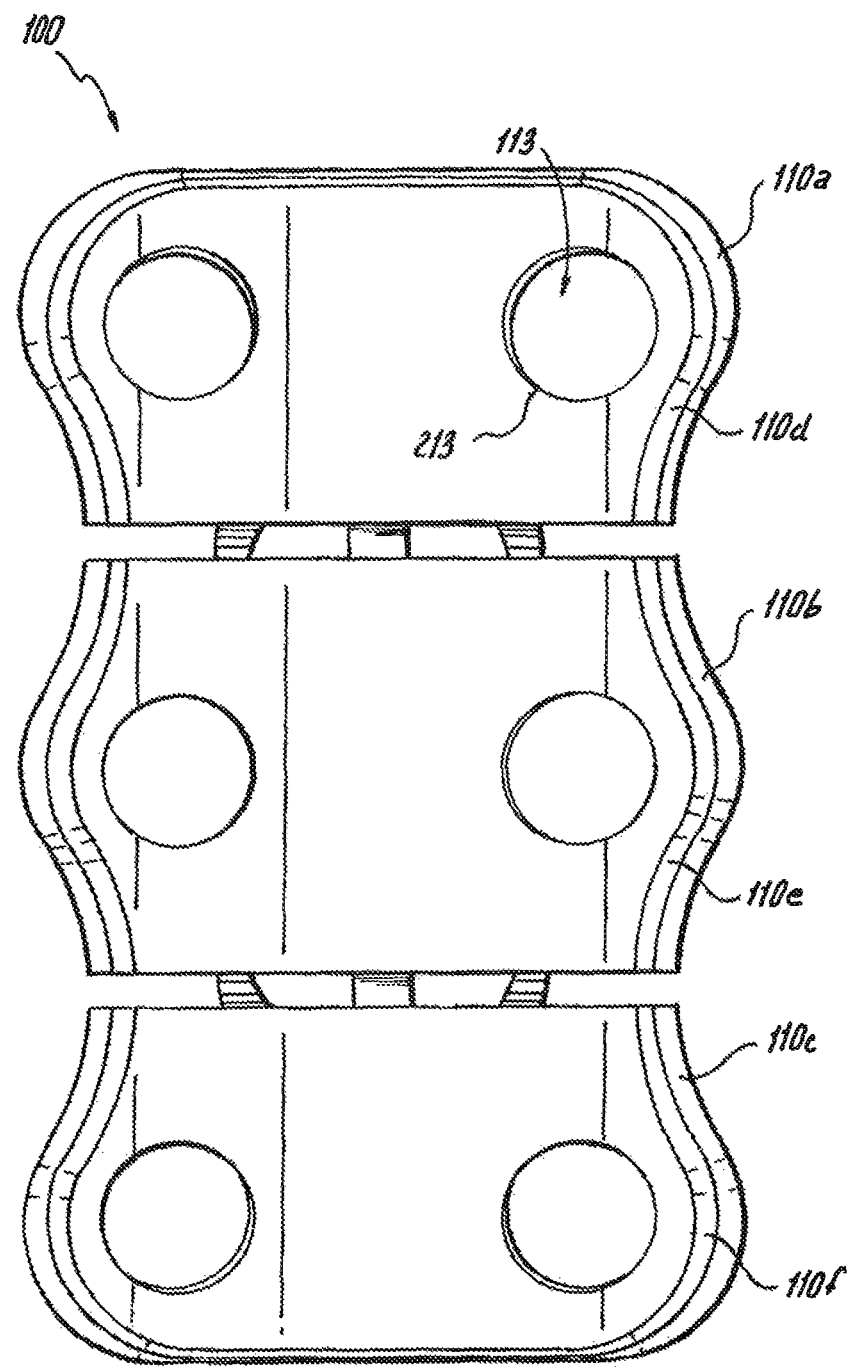
FIG. 6B is a bottom line drawing of the dynamic vertebral column plate system of FIGS. 1A and 1B, shown without the accompanying screws.
Figure 7A:
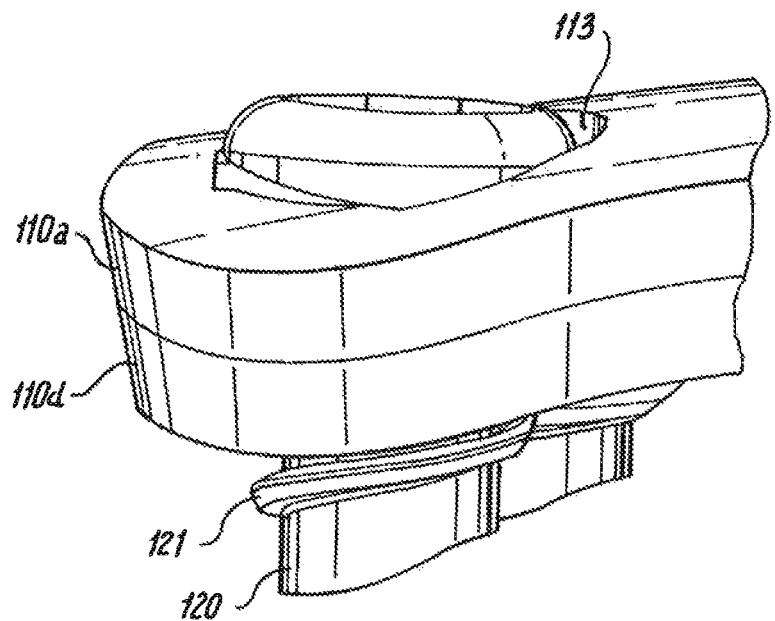
FIGS. 7A and 7B are, respectively, a line drawing and a rendering illustrating a detail view of a portion of the dynamic vertebral column plate system of FIGS. 1A and 1B, shown with an accompanying screw.
Figure 7B:
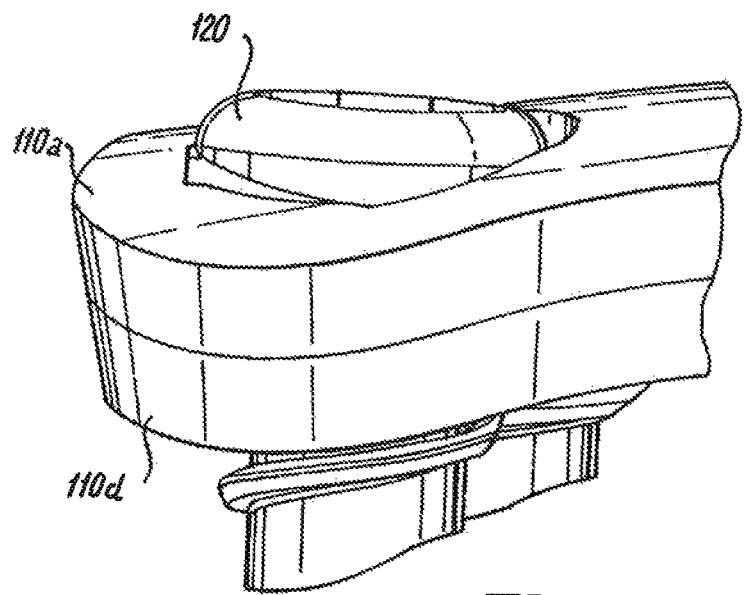
Figure 9:
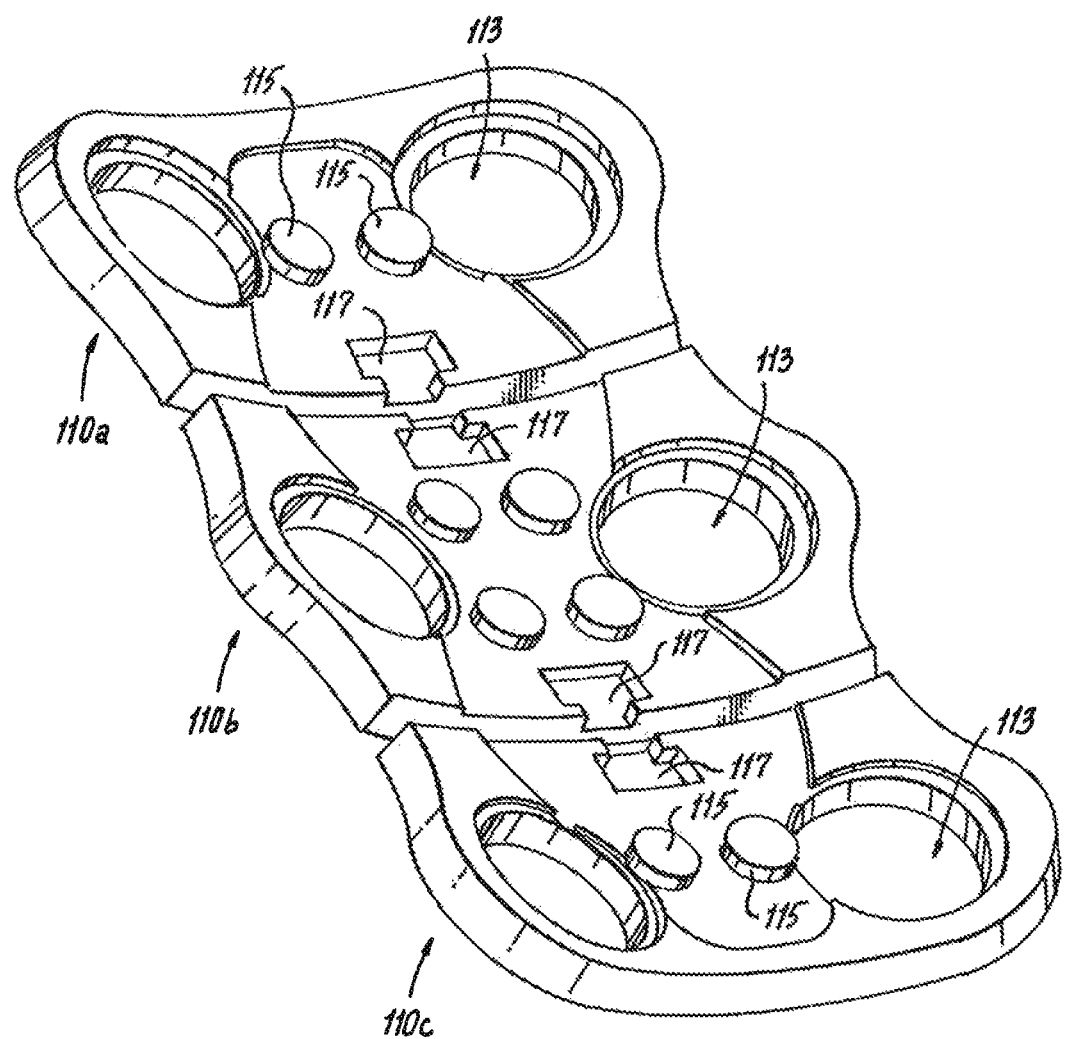
FIG. 9 is an a isometric line drawing, showing the lower surface of the upper plate segments of the dynamic vertebral column plate system of FIGS. 1A and 1B.
Figure 10:
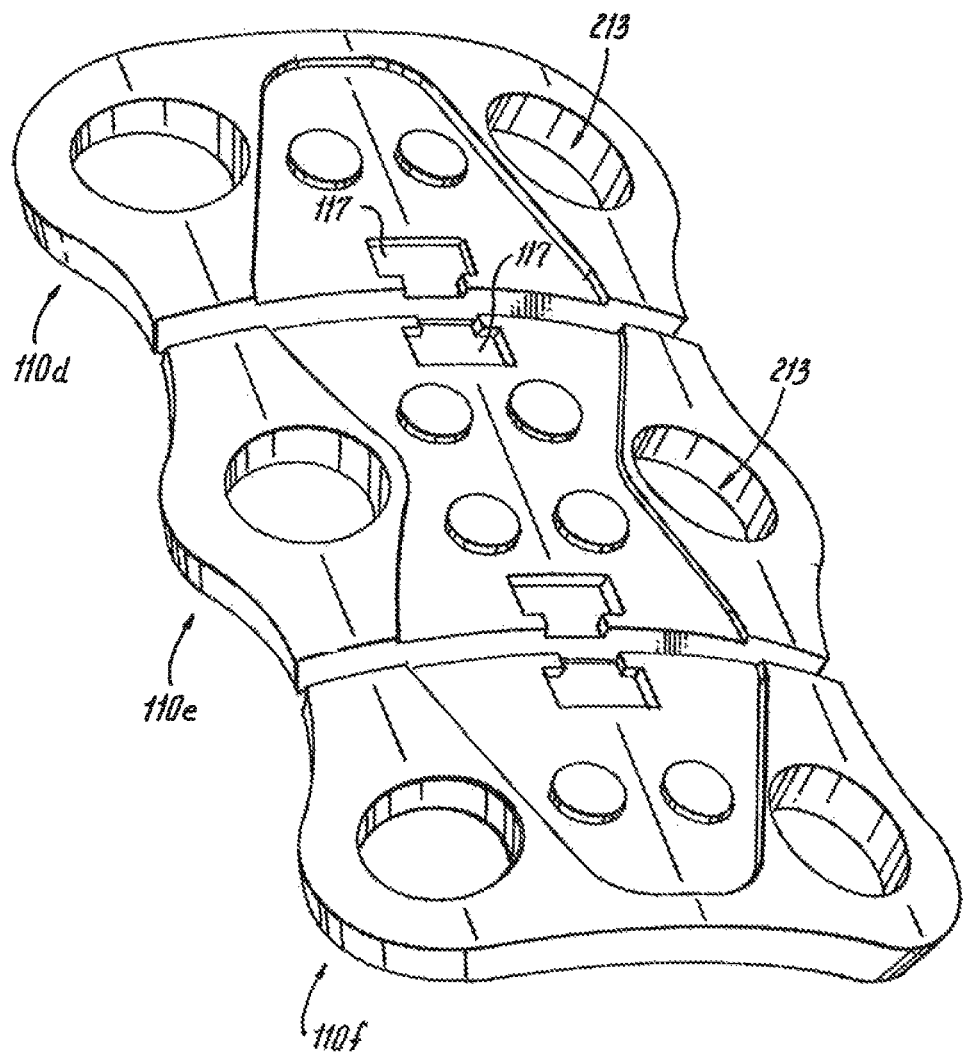
FIG. 10 is an an isometric line drawing, showing the upper surface of the lower plate segments of the dynamic vertebral column plate system of FIGS. 1A and 1B.

FIG. 6A is a bottom line drawing of the dynamic vertebral column plate system of FIGS. 1A and 1B, shown with accompanying screws. FIG. 6B is a bottom line drawing of the dynamic vertebral column plate system of FIGS. 1A and 1B, shown without the accompanying screws. FIGS. 7A and 7B are, respectively, a line drawing and a rendering illustrating a detail view of a portion of the dynamic vertebral column plate system of FIGS. 1A and 1B, shown with an accompanying screw. FIGS. 8A and 8B are, respectively, isometric line drawings of top and bottom surfaces of an upper plate segment of the dynamic vertebral column plate system of FIGS. 1A and 1B. FIG. 9 is an a isometric line drawing showing the lower surface of the upper plate segments of the dynamic vertebral column plate system of FIGS. 1A and 1B, and FIG. 10 is an a isometric line drawing, showing the upper surface of the lower plate segments of the dynamic vertebral column plate system of FIGS. 1A and 1B.

As best seen in FIG. 3C, for example, the lower plate portions 120a-c of each plate segment include smaller apertures 123a, b or c, respectively for the screws 150 than the apertures 113a-c provided, respectively in the upper plate portions 110a-c. This allows firm engagement of the construct 100 to the vertebral column, with the larger apertures 113a-c allowing space for inserting the retaining clip 159.

Figure 12:
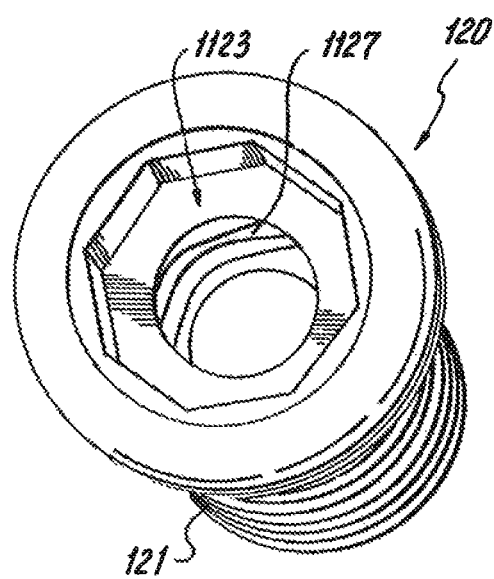
FIG. 12 is a top isometric view of the screw of FIGS. 11A, 11B and 11C, shown without the retaining clip, and illustrating a socket portion thereof.

As seen best in FIGS. 11A-11D, the screws 150 illustrated can include external threads 151 thereon for securely engaging bone. A proximal groove 155 accepts a retaining clip 159 for facilitating engagement with the construct 100. As seen in FIG. 12, the screw 150 can include a socket portion 153 and internal threads 157 provided therein to facilitate removal of the screw 150 from the bone, if necessary or desired. Such threads 157 are preferably opposite in directionality to the threads 151 of the screw 150, so that as the screw is being removed, the extraction tool does not disconnect itself from the screw 150.

Figure 13:
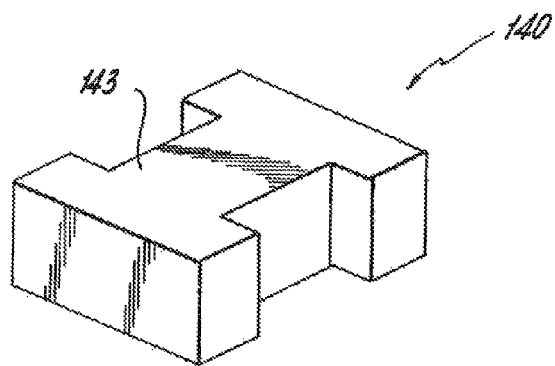
FIG. 13 is an isometric line drawing showing an engagement member for joining adjacent plate segments of the dynamic vertebral column plate system of FIGS. 1A and 1B.
Figure 14:
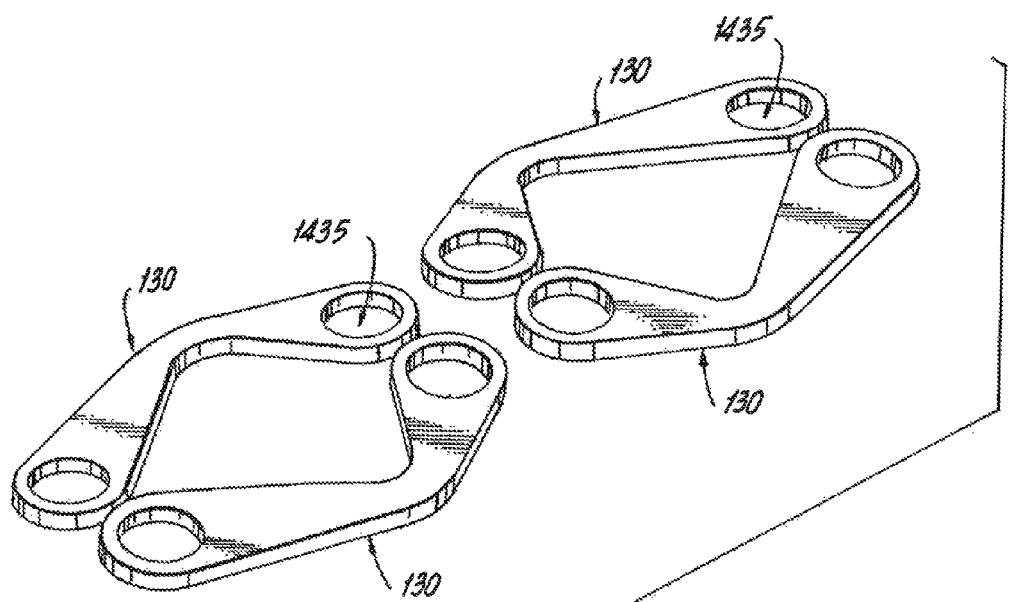
FIG. 14 is an isometric line drawing showing spring members for joining adjacent plate segments of the dynamic vertebral column plate system of FIGS. 1A and 1B.
Figure 15A:
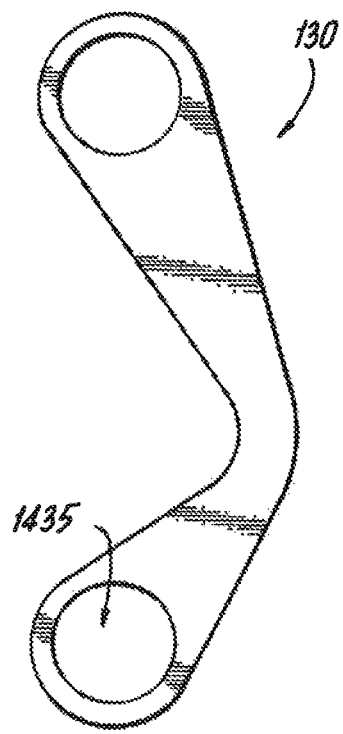
FIG. 15A is a top view of a spring member of FIG. 14.
Figure 15B:
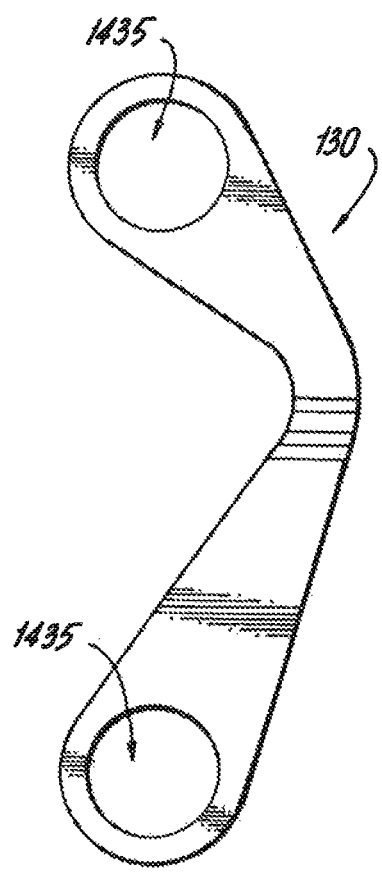
FIG. 15B is a bottom view of the spring member of FIG. 15A.
Figure 15C:
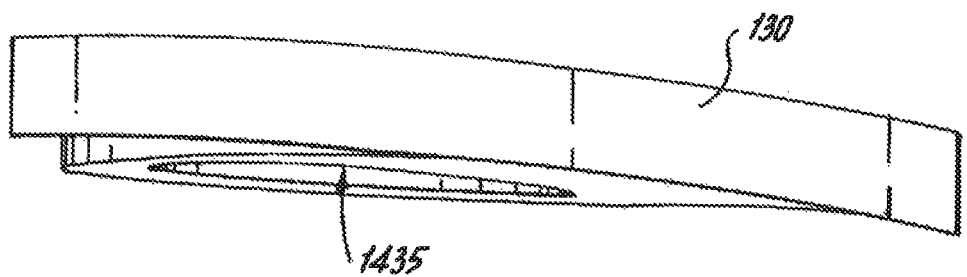
FIG. 15C is a front isometric view of the spring member of FIG. 15A.
Figure 15D:
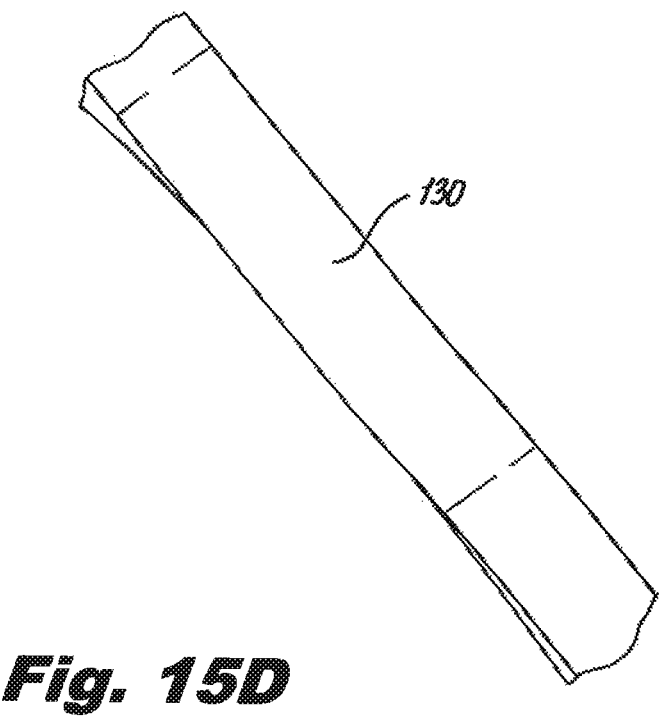
FIG. 15D is a an enlarged partial view of the spring member of FIG. 15A, illustrating a central bend thereof.
Figure 16:
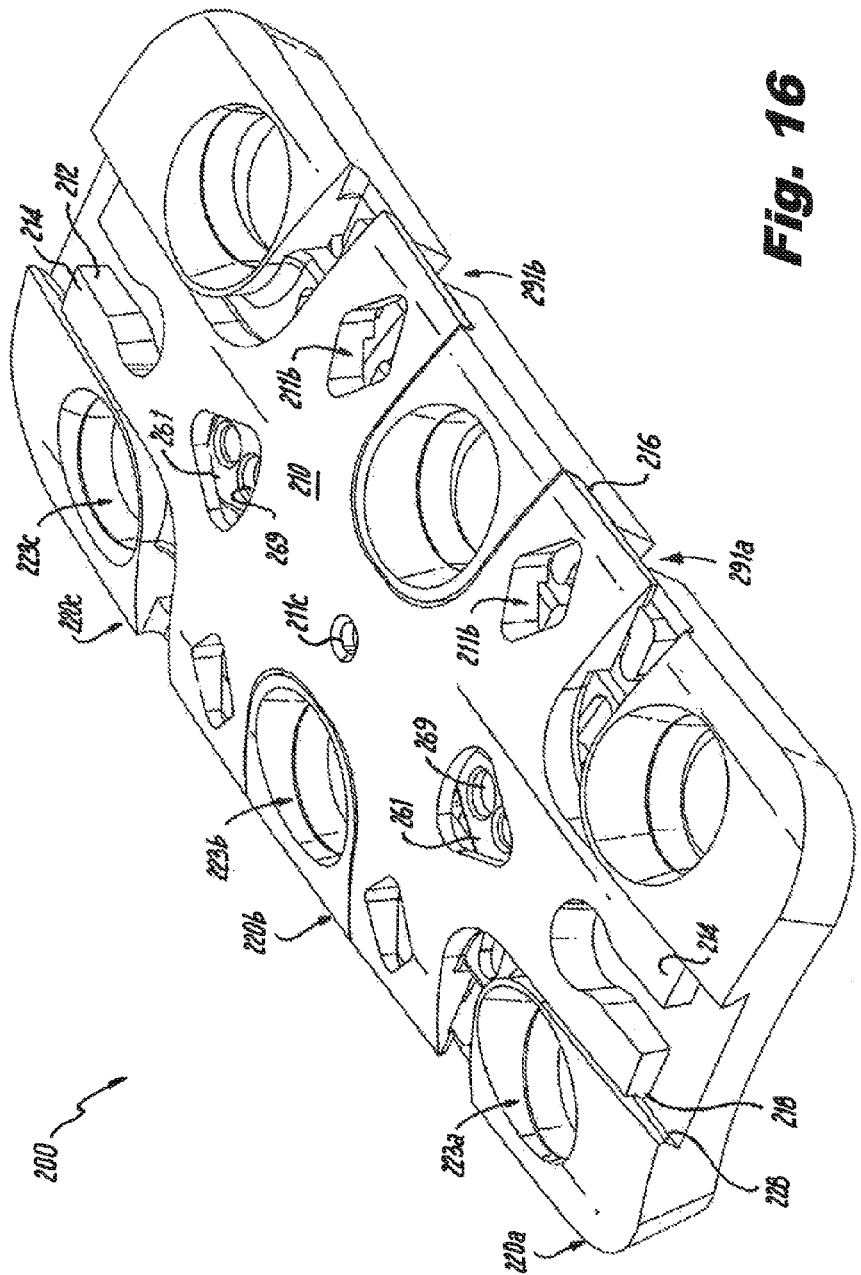
Figure 17:
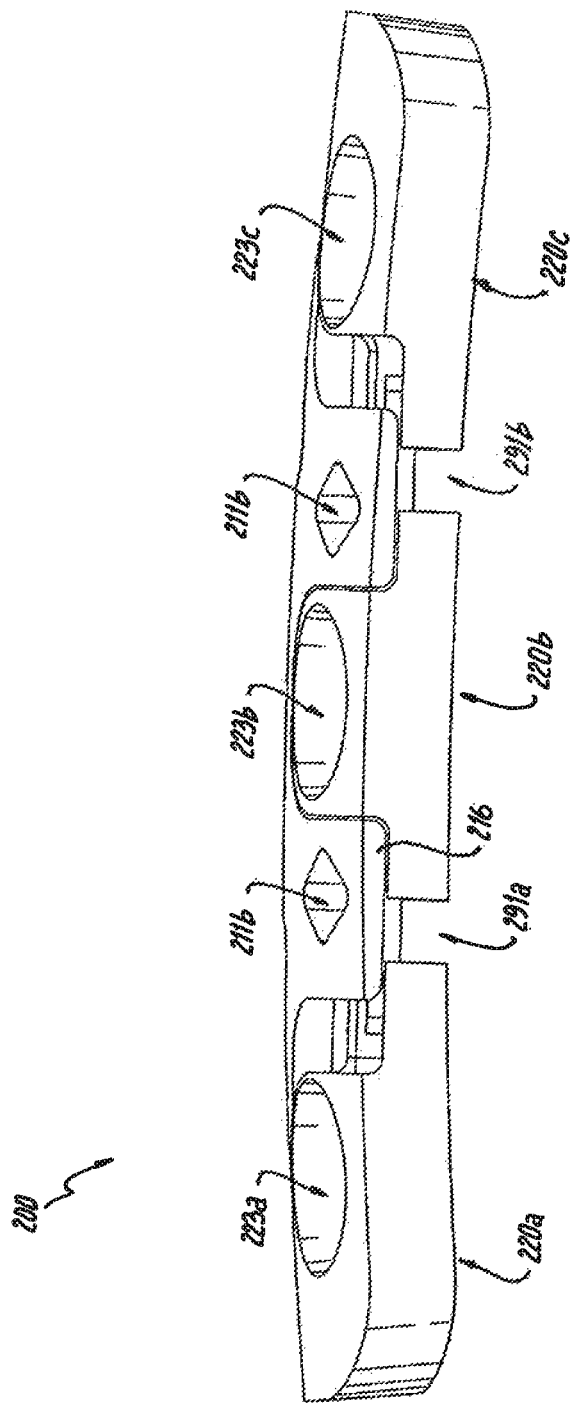
Figure 18:
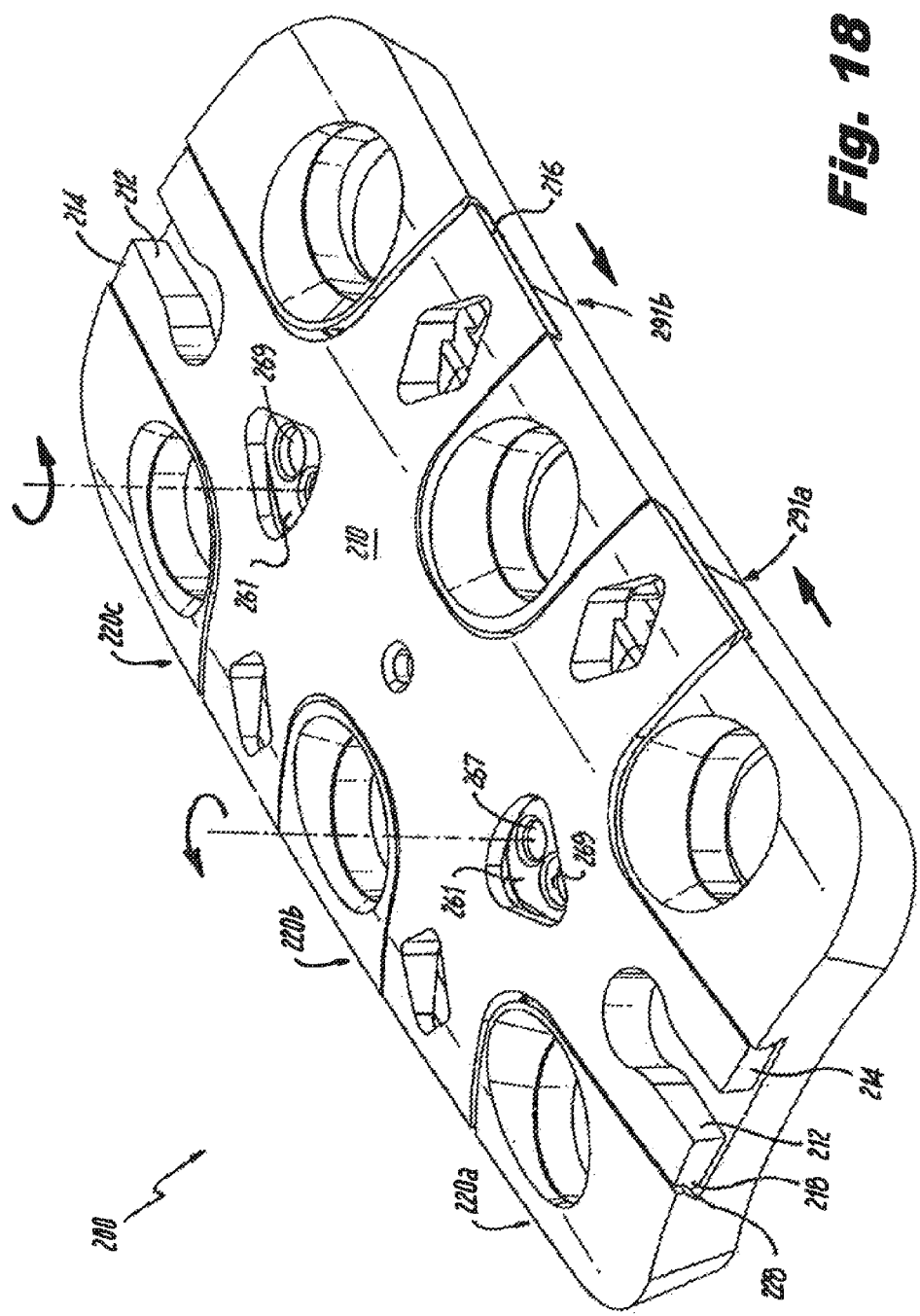
Figure 19:
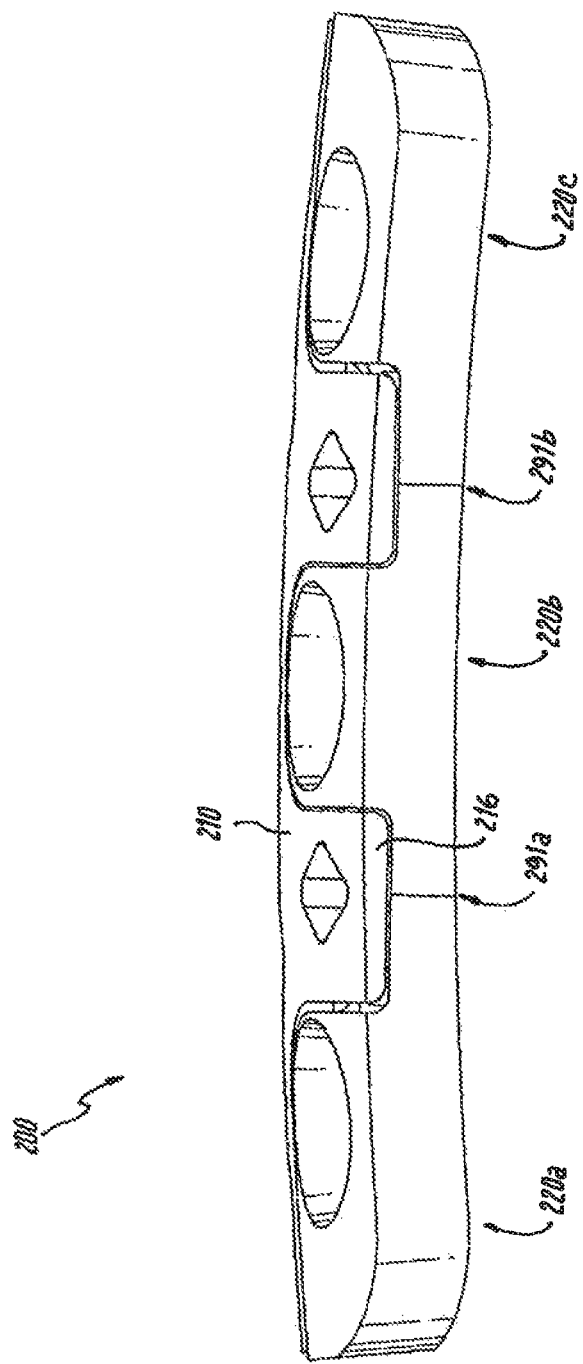
Figure 20:
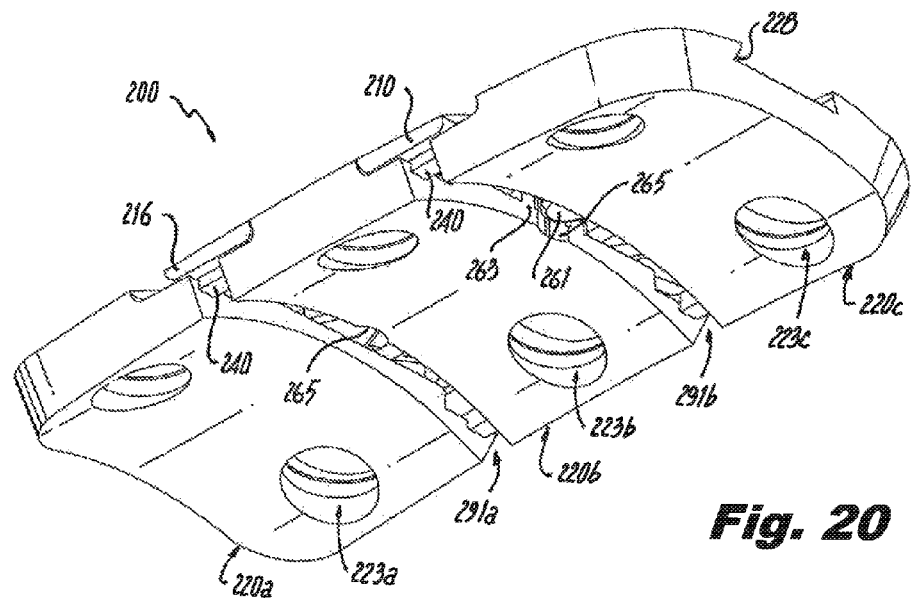
Figure 21:
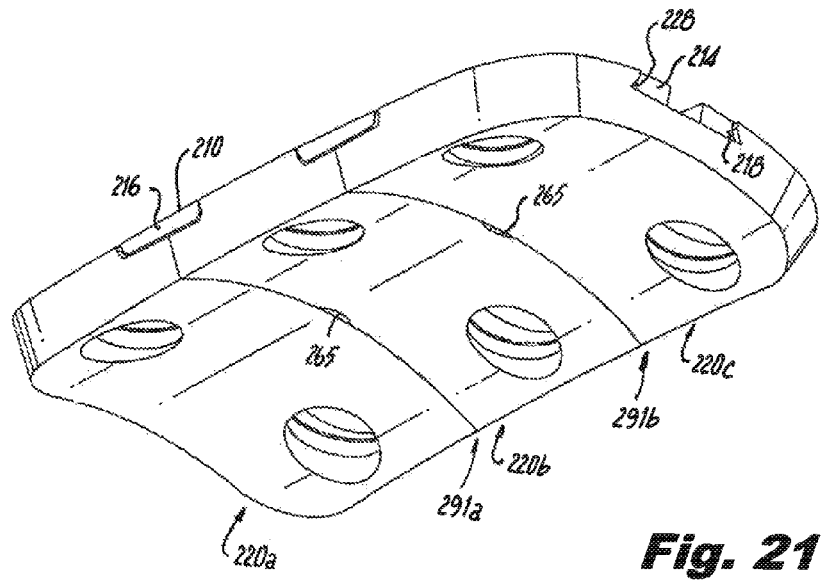

As best seen in FIG. 13, the engagement member 140 is shaped in this embodiment substantially as a solid "I-beam." Any of a variety of materials can be used, including but not limited to stainless steel, titanium alloys, nickel alloys such as Nitinol, polymeric materials, ceramic materials or composite materials, for example. The shape of the engagement member 140, and particularly the web portion 143 thereof, provides resistance to, but can allow, if so-embodied, a predetermined amount of bending of a construct created therewith.

In accordance with a preferred embodiment, the plate segments move in an axial direction (parallel to the longitudinal axis of the construct 100), guided by the engagement members 140. The springs 130 exert a compressive force between segments of the construct 100, while the engagement members 140 help stabilize the construct 100. In such embodiments, the engagement members 140 are preferably relatively strong, and stiff (i.e. resistant to bending forces).

Alternatively, if embodied to allow bending of the construct 100, due to the placement of the springs 130 with respect to the engagement member 140, lateral bending (roughly in the plane of the plate segments 110, 120, but parallel to the longitudinal axis thereof) would generally be less than in the direction perpendicular thereto (out of the plane of the plate segments 110, 120 (but still in a plane parallel to the longitudinal axis of the construct). The stiffness of the engagement member 140 in such embodiments can be selected by varying the material properties thereof, by changing the composition of the material, treating the material, or by altering the shape thereof—particularly the cross-sectional shape to alter the area moment of inertia thereof.

As seen in FIGS. 14 and 15A-15F, the spring elements 130 include engagement apertures 135 for mating with the spring engagement members 115 formed on the upper plate portions 110a-c and spring engagement members 125 formed on the lower plate portions 120a-c. The spring elements 130 can be formed of any suitable material, including but not limited to stainless steel, titanium alloys, nickel alloys such as Nitinol, polymeric materials, ceramic materials or composite materials, for example. The stiffness of the spring elements 130 can be selected by varying the material properties thereof, by changing the composition of the material, treating the material, or by altering the shape thereof. With respect to the springs 130, the nature of the integral bend and the cross-section of the component in that area can be altered to increase or decrease the stiffness thereof.

As illustrated, the spring 130 narrows to a relatively small cross-sectional area. When axial compression is the main modality of loading, the springs 130 can be provided pre-stressed, wherein the relaxed state of the spring results in a shorter length of the construct 100 than the pre-stressed state. In such embodiments, the construct 100 can be provided with removable spacers 160 (FIG. 1C) between plate segments that are removed following attachment to the vertebral column segment. Thereafter, the springs 130 exert a constant axial compressive force on the vertebral column segment.

In accordance with the invention, the stiffness of the engagement members 140, springs 130, in conjunction with the materials of the plate segments 110, 120 are selected to provide a desired amount of flexion in the construct when joined with a vertebral column segment. In accordance with one aspect, devices in accordance with the invention allow for between about 0 and 5.0 mm, and preferably between about 1.0 mm to 3.0 mm of axial contraction at each level, across each inter-vertebral space. In accordance with another preferred aspect, the subject devices allow for about 2.0 mm of axial contraction at each level. If desired, the characteristics of the construct can be varied at different levels, providing greater preload force, or alternatively resistance to axial contraction and/or bending at one level than at another level, if desired.

The shape of the plate segments 110, 120, engagement members 140 and springs 130 preferably result, when combined with the respective vertebral column segment, in a curvature very close to the natural curvature of that vertebral segment. Other than providing a bias to maintain pressure across the inter-vertebral spaces to promote fusion of bone grafts, the curvature is preferably very close to that of the vertebral column segment to which it is to be attached.

Further, the spacing between adjacent plate segments can be selected as desired, and can vary between adjacent levels, across consecutive inter-vertebral spaces, for example. Such flexibility allows for more versatility when used with a patient's individual anatomy.

Moreover, devices in accordance with the invention can be configured so as to provide preloading across an inter-vertebral space to facilitate spinal fusion. This is accomplished, for example, by providing a bias in the curvature of the assembled construct 100. This can be achieved by providing the engagement members 140 and/or springs 130 with a pre-formed bend. Such bend need only be slight to result in an effective bias.

Screws, such as screws 150, for use in conjunction with devices in accordance with the invention can include any desired features known in the art. Such screws can be adapted for fixed angle insertion or variable angle insertion having an arcuate lower surface at the junction of the plate segments 110, 120. Such screws can be self-tapping or self-drilling. Features of example screws for use with devices in accordance with the invention are described below in connection with FIGS. 31A-H.

Figure 23:
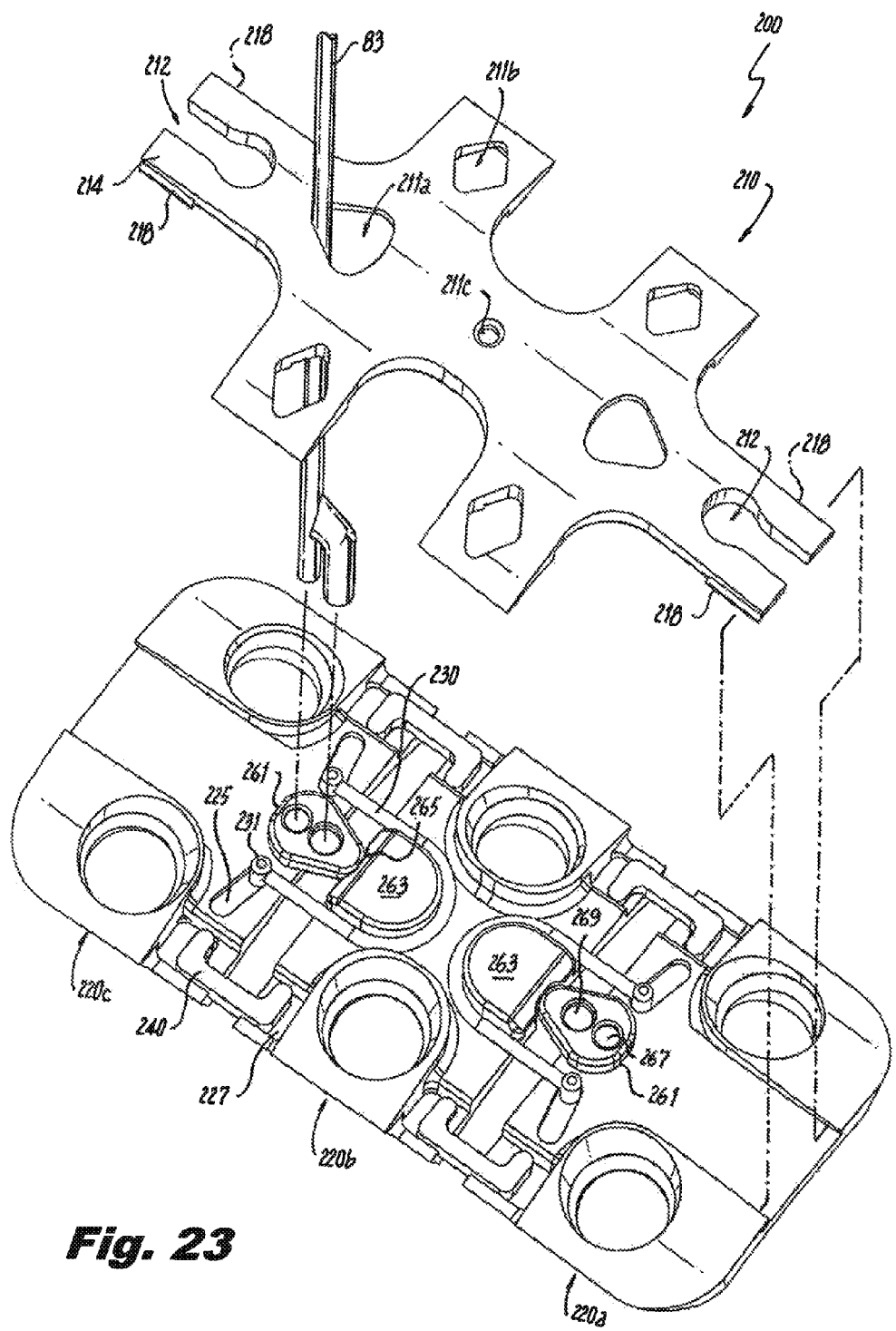
Figure 24:
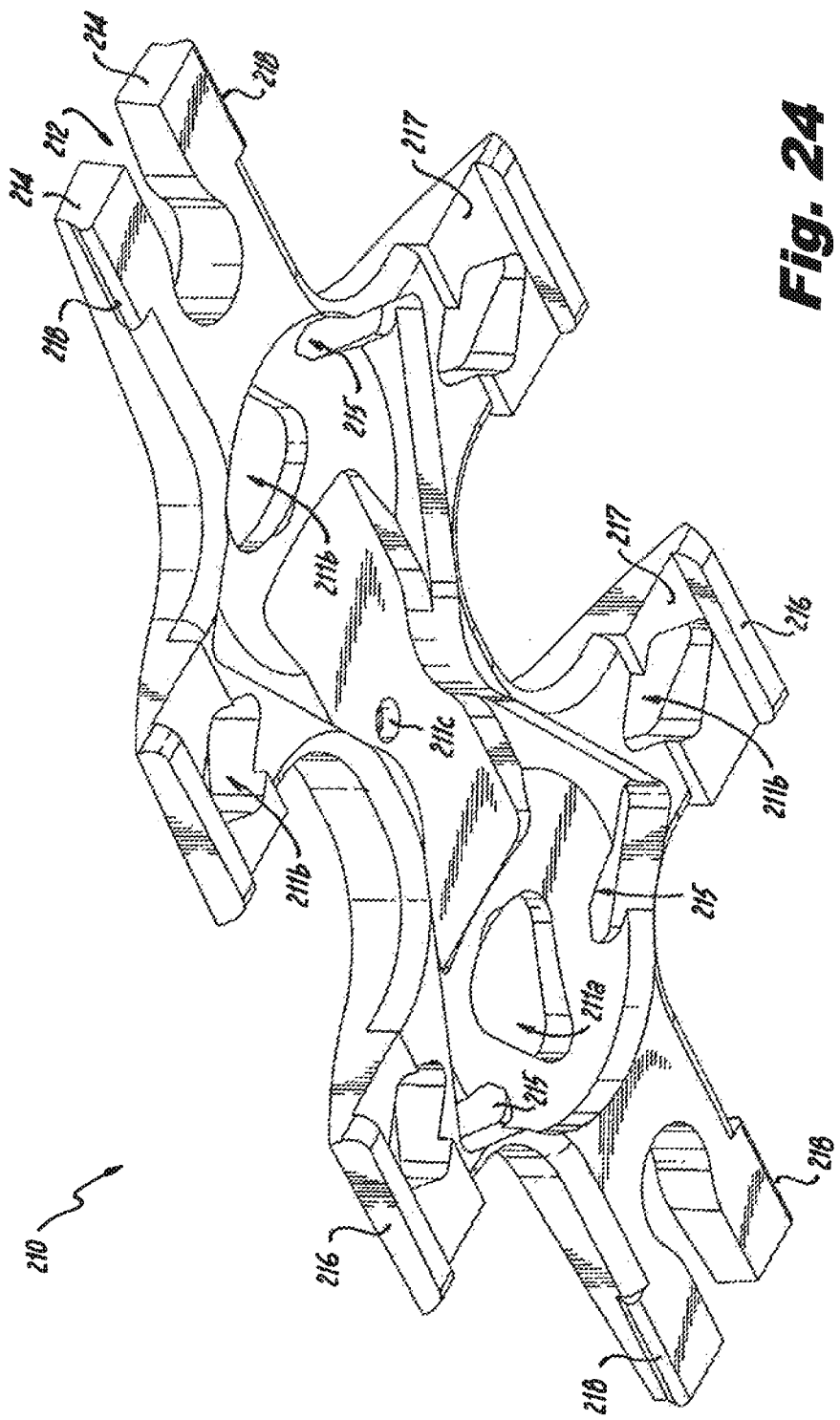
Figure 25:
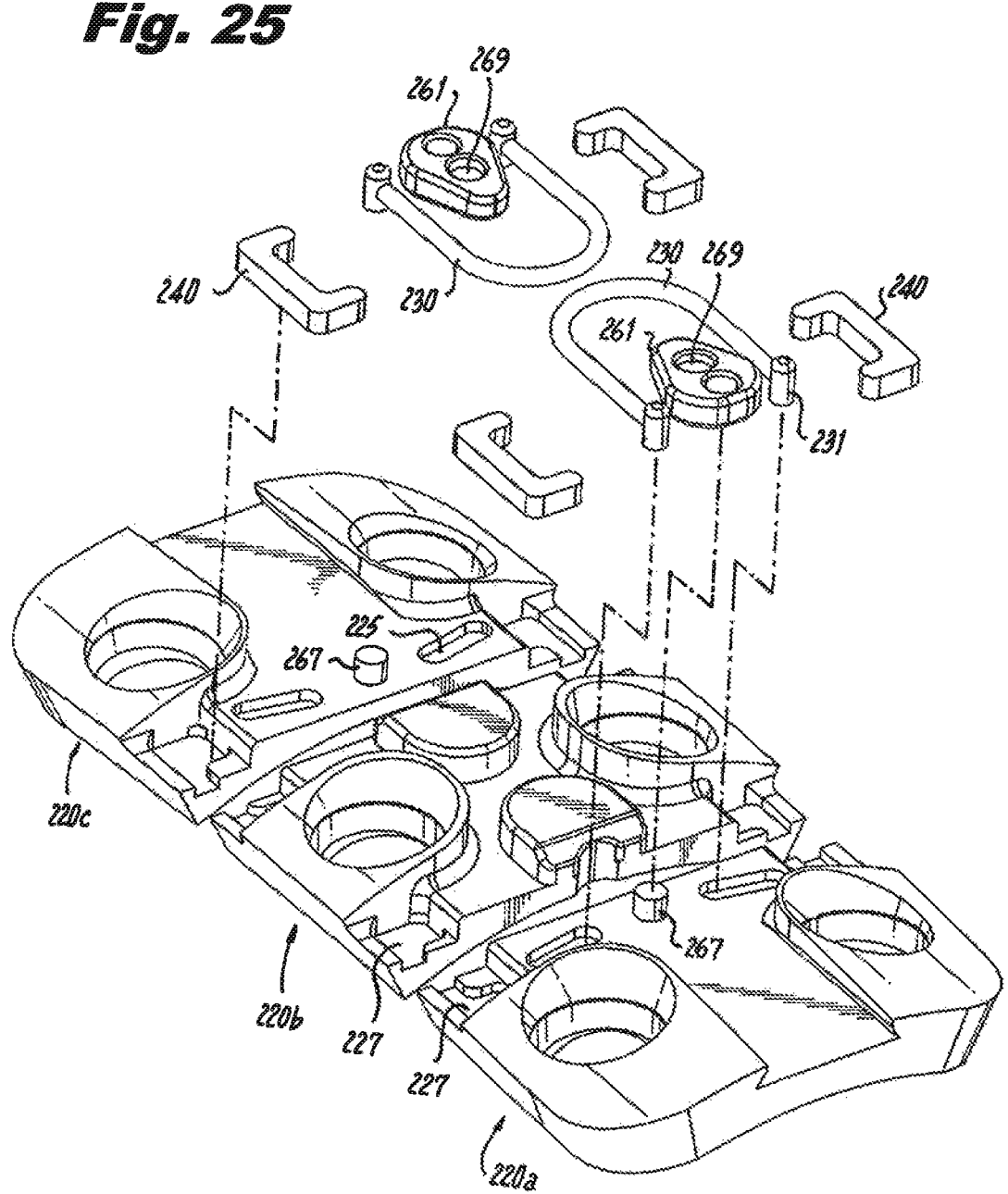

FIGS. 16-29 illustrate various views of another exemplary embodiment of a dynamic vertebral column plate system construct in accordance with the invention, designated generally by reference number 200. The construct 200 has, among other features, arcuately bent rod or bar-shaped springs 230 and an integral cam element 261 that permits use of the construct 200 as either a static plate or dynamic plate, providing preload at one or more levels of a spinal segment. Simply put, if the cam 261 is left in a locked position (e.g., as shown in FIG. 23) following implantation or alternatively, unlocked prior to implantation, then no preload will be applied to that respective level. If, however, the cam 261 is locked during implantation and unlocked following attachment to a spinal segment, a preload, provided by a respective spring 230, will be applied at that level.

The construct 200 includes a number of features analogous to the construct 100 discussed in connection with FIGS. 1-15F. For example, the construct 200 includes a plurality of apertures 223a-c for accepting screws for connection with respective vertebrae, a plurality of lower plate portions 220a-c, engagement members or guides 240, and springs 230 for applying preload at respective levels, although the configuration of these features may vary somewhat substantially from those of the construct 100, as will be described in more detail below.

Notable differences between the construct 100 discussed in connection with FIGS. 1-15F, and the construct 200 of FIGS.

16-29 include a unitary upper plate 210, an integral cam 261 and associated features, a different arrangement of the springs 230 that apply a preload, if desired.

The unitary upper plate 210 of the construct 200, is distinct in configuration from the individual upper plate portions 110a-c of the construct 100 of FIGS. 1-15F. The unitary upper plate advantageously enhances stability of the construct 200, and thus also any attached spinal segment, while permitting linear translation of adjacent lower plate segments 220a, 220b, 220c, and therefore also permitting an axial application of load across the attached spinal segment to promote fusion.

As can be seen particularly in FIGS. 22A, 22B and 22C, the end plate segments 220a, 220c are engaged with the upper plate 210 by way of a female dovetail 228 formed in the lower plate segments 220a, 220c, and a male dovetail 218 formed on the upper plate 210. The dovetails 218, 228 restrain the relative movement between the end plate segments 220a, 220c and the top plate 210 along each axis except for along a longitudinal axis, which movement is restrained in expansion by engagement members 240 and springs 230, and restrained in contraction by interference with adjacent plates, such as the intermediate plate 220b. Engagement of the dovetail 218 of the upper plate 210 is permitted with the provision a cutout 212, which allows for deflection of resulting forks 214 of the upper plate 210, surrounding the cutout 212, on which the dovetail 218 is formed.

As with the construct 100, engagement members 240 are provided, which serve to promote stability of the construct 200 and to limit expansion of the construct 200 beyond a predetermined amount. The lower plate segments 220a-c include slots 227 to accommodate the engagement members 240, while the upper plate 210 includes corresponding slots 217 for that purpose. The upper plate 210 includes tail portions 216 that partially define slots 217 therein for the engagement member 240, and permit close engagement at lateral edges of the construct 200 between the upper plate 210 and lower plate segments 220a, 220b, 220c.

Various apertures 211a, 211b, 211c are provided in the upper plate 210 for respective purposes. A central aperture 211c is provided to permit pinning of the lower intermediate plate segment 220b to the upper plate 210 during assembly. Such a pin can be peened, welded or connected to the upper and lower plates in another suitable manner. Such a pin can be integrally formed, such as by casting and/or machining, with one of the lower intermediate plate segment 220b and the upper plate 210, for example. Alternatively, any intermediate plate such as plate 220b can be connected to the upper plate 210 in another manner, such as by a dovetail feature discussed in connection with the end plate segments 220a, 220c, for example.

Figure 30A:
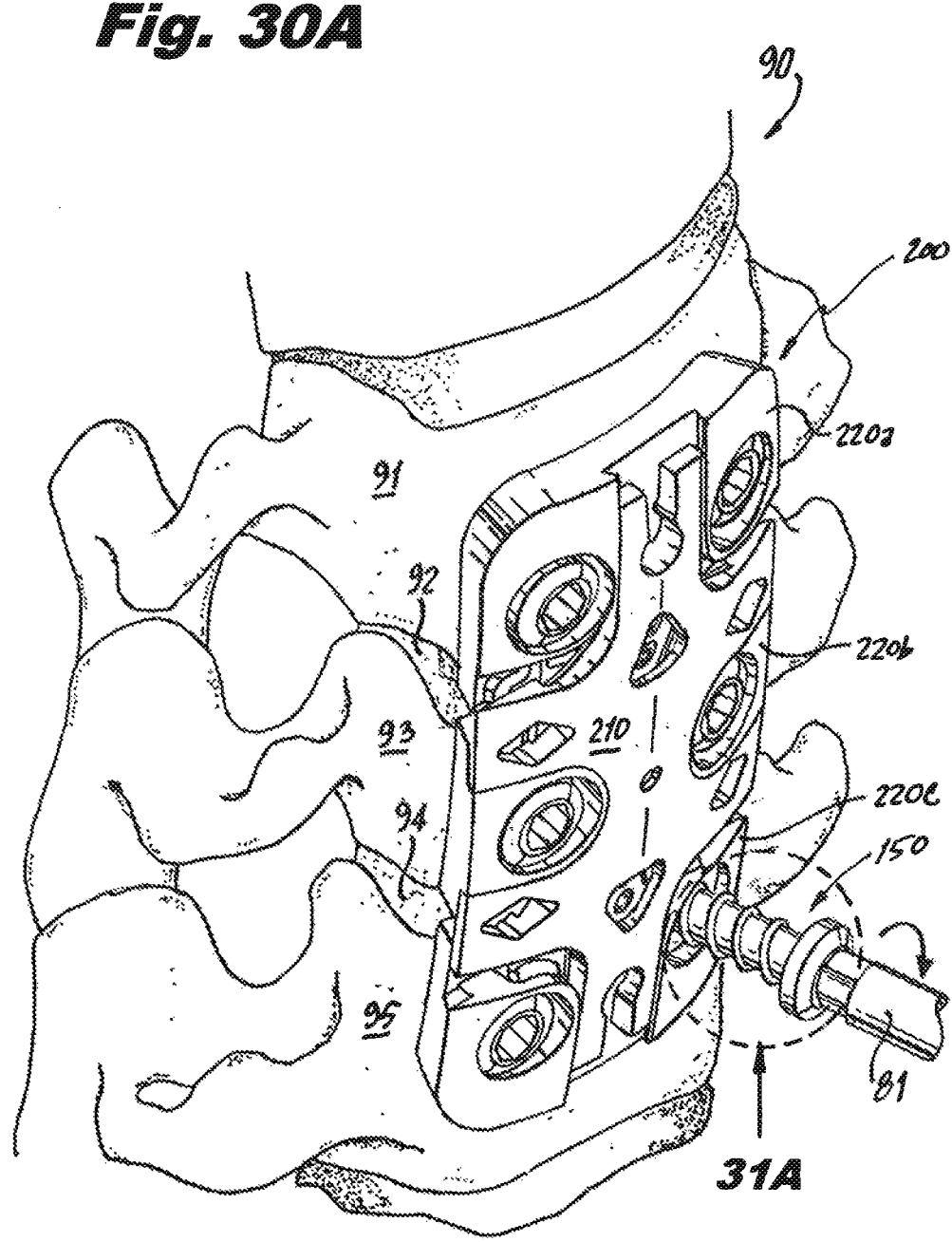
FIGS. 30A-C illustrate implantation steps of the dynamic vertebral column plate system construct of FIGS. 16-29, but which steps apply generally to other embodiments of the invention.
Figure 30B:
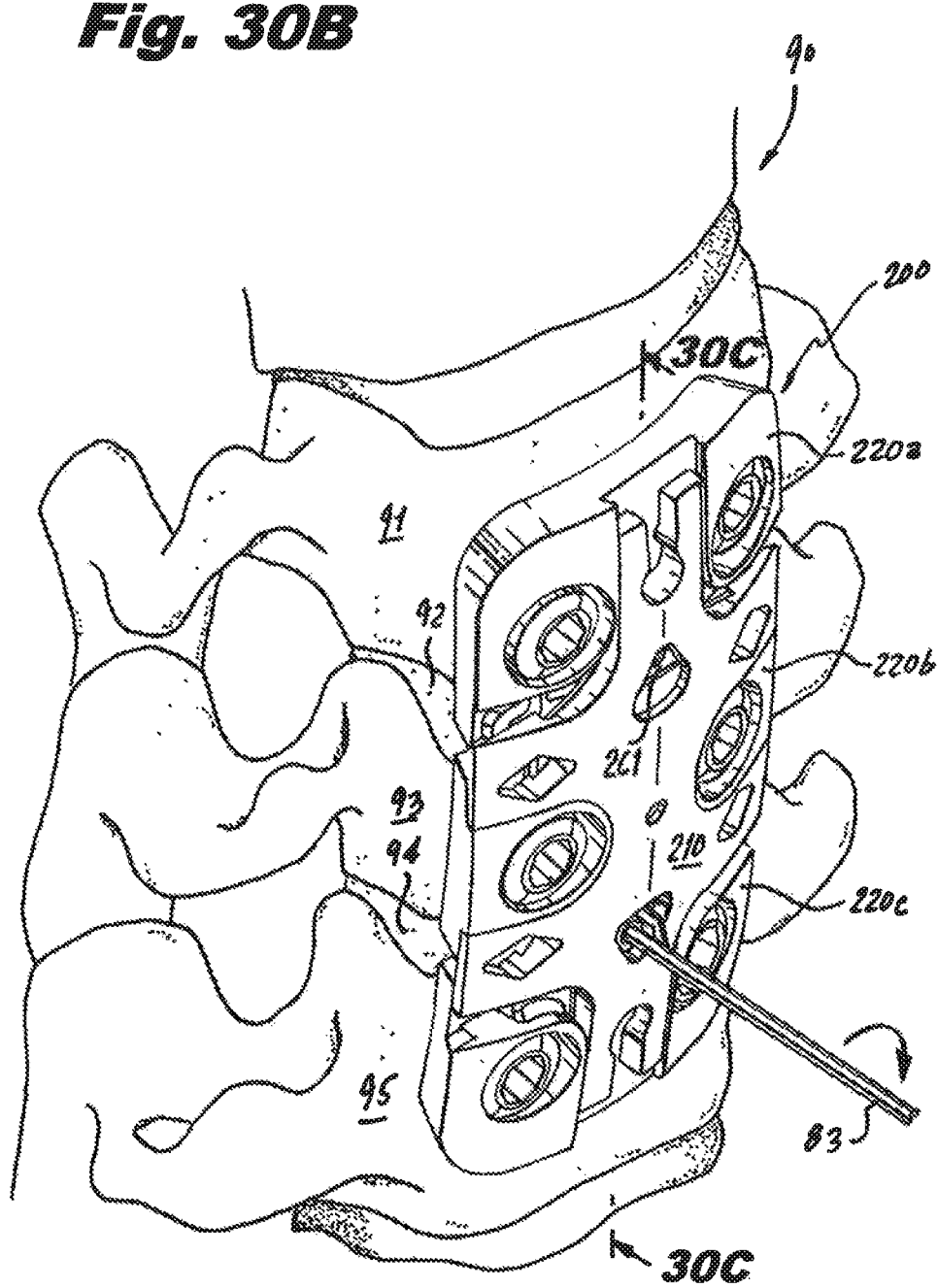

Respective apertures 211a, 211b are provided to enable access to each cam 261, to rotate the cam 261 between locked and unlocked positions, as illustrated in FIG. 30B, for example. Apertures 211b are also provided in line with the spaces 291a, 291b between lower plate segments 220a, 220b, 220c, which apertures 211b provide a viewing window of the inter-vertebral space, through the construct 200, so that a surgeon can view the relative spacing between lower plate segments 220a, 220b, 220c, and also the condition of a bone graft (of the vertebrae and any fusion devices or materials), during and after attachment of the construct 200 to a spinal segment. A surgeon can therefore determine, based on his or her experience, whether or not that level of the construct should remain static or if the cam 261 should be unlocked to provide a dynamic load application at that level. The surgeon may take various factors into account, including any gaps that he or she may see in the inter-vertebral space, between vertebrae and any fusion materials, for example.

Figure 26:
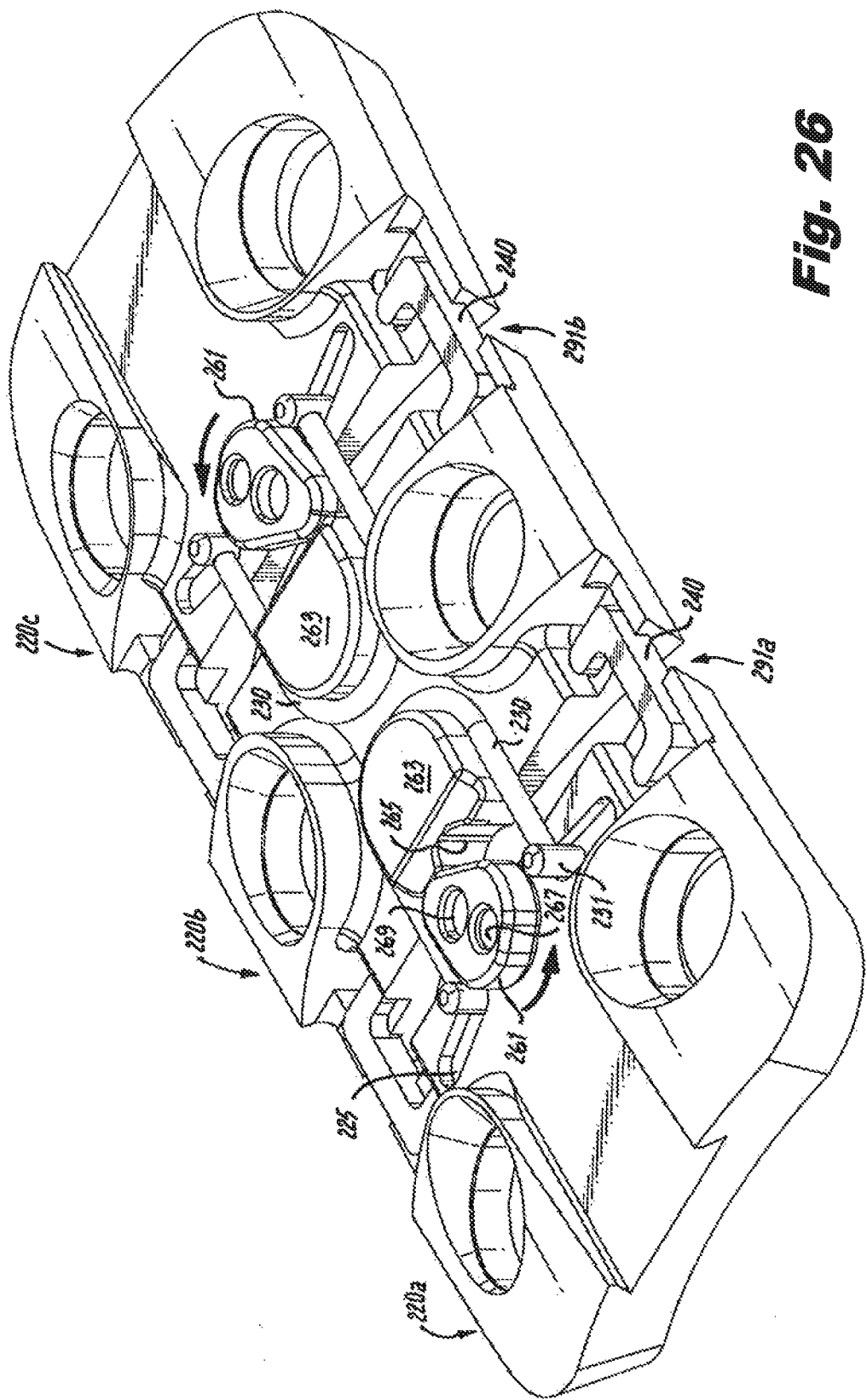
Figure 27:
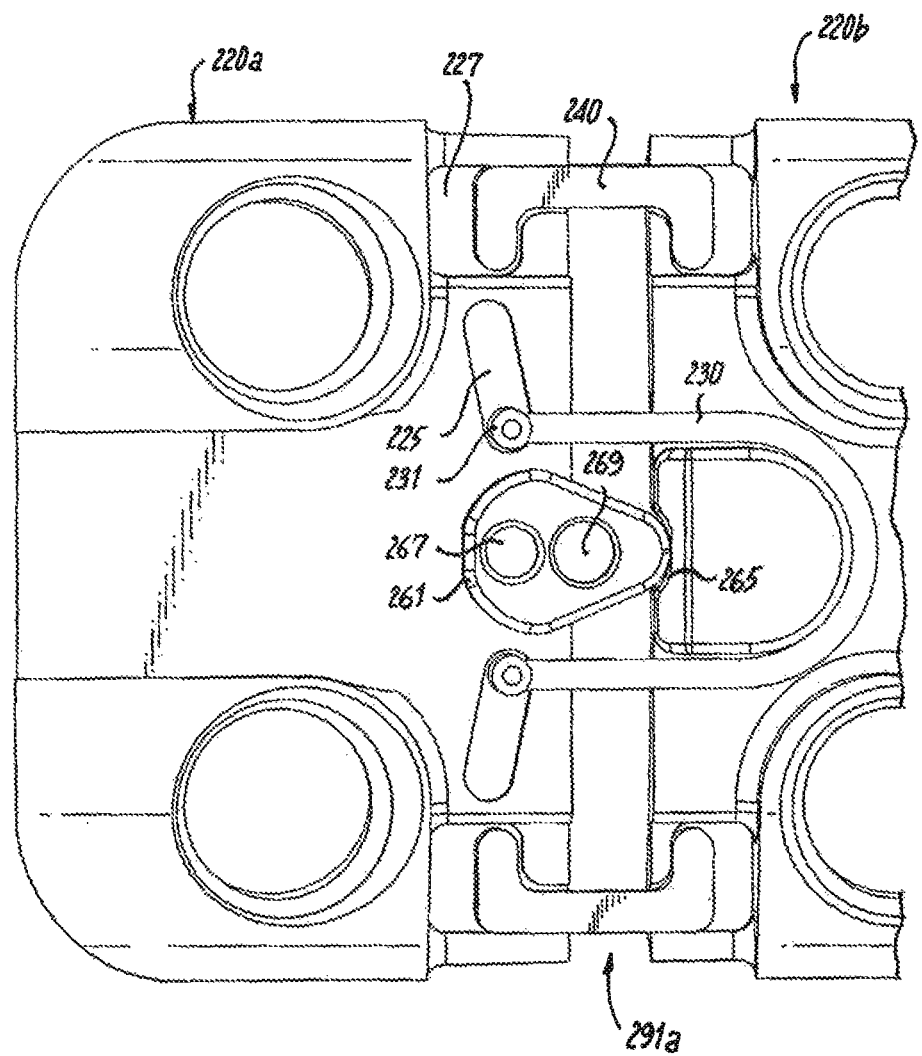

Following implantation, a surgeon can elect to leave one or more of the cams 261 in the locked position, or alternatively can unlock one or more cams prior to implantation, causing the corresponding gap (e.g. 291a, 291b) to close. In either case, that level of the construct 200 would behave essentially as a static plate. More typically, however, following implantation, each of the cams 261 will be unlocked by turning the cam 261 from its seat in recess 265, as shown in FIG. 26, for example. At that time, even if no visible contraction occurs, the spring 230 at that level begins to exert force across the corresponding gap (e.g. 291a), and therefore to the spinal segment, which will typically be a fusion between vertebrae.

In accordance with an alternative embodiment, the cam 261 can be provided that is similar to the cam 561 discussed below in connection with the embodiment of FIGS. 33-39. Alternatively still, the cam 261 can be configured and adapted to engage a pin at one position to stretch the respective spring 230, to thus effect an increased preload following implantation.

The springs 230 are configured as an arcuate rod or bar. As illustrated, the ends of the springs 230 are held in pins 231 that are translatable with respect to slots 215 and 225, formed respectively in the upper plate 210 and lower plates 220a, 220c (See FIGS. 23 and 24).

At the maximum extent of expansion of the construct 200, illustrated for example in FIGS. 16, 17, 20, and 23, gaps 291a, 291b between adjacent lower plate segments 220a, 220b and 220c are also at their maximum, which is limited by the central spring 230 and the laterally placed U-shaped engagement members 240, which are engaged in recesses 117, 127 formed in the top plate 210 and each of the bottom plate segments 220a-c, respectively. The cams 261, rotate on respective bosses 267 and in their locked position, engage recesses 265 formed on a facing surface of the adjacent plate, maintaining a predetermined spacing. In addition to an aperture in the cam 261 for accommodating the boss 267, an aperture 269 can be provided in the cam for engagement with a tool for rotating the cam 261.

The dimensions of the components can be selected to vary the amount of spacing between adjacent plates, however, in accordance with one preferred embodiment, the maximum spacing of the gaps 291a, 291b is about 2.0 mm, for example, for use in a cervical spinal segment. This spacing can be selected to be smaller or larger, such as between 1.0 mm and 3.0 mm of translation, depending on the placement of the construct 200 (or any other construct in accordance with the invention). That is, if used on a lumbar spinal segment, the construct can be configured so as to provide a larger maximum spacing between plate segments, for example 3.0 mm or perhaps larger if indicated for a particular application. The maximum spacing 291a, 291b between plate segments 220a-c determines the maximum range of travel along which the spring 230 can apply a preload to a level of the spine, such as across a fusion.

A block of bone, a fusion cage or other fusion material is typically inserted in place of a disc, between vertebrae that are to be fused together and carries the bulk of load carried by the spine. The construct 200, then provides stabilization to the spinal segment to which it is attached while minimizing load transfer to the construct, which promotes proper fusion. The springs 230 also maintain a load on the segment even in the absence of external load. In this manner, the construct 200 (and other constructs in accordance with the invention) advantageously permit settling of fusion materials, while minimizing any spacing between adjacent vertebrae and the fusion materials, further enhancing fusion.

Figure 29:
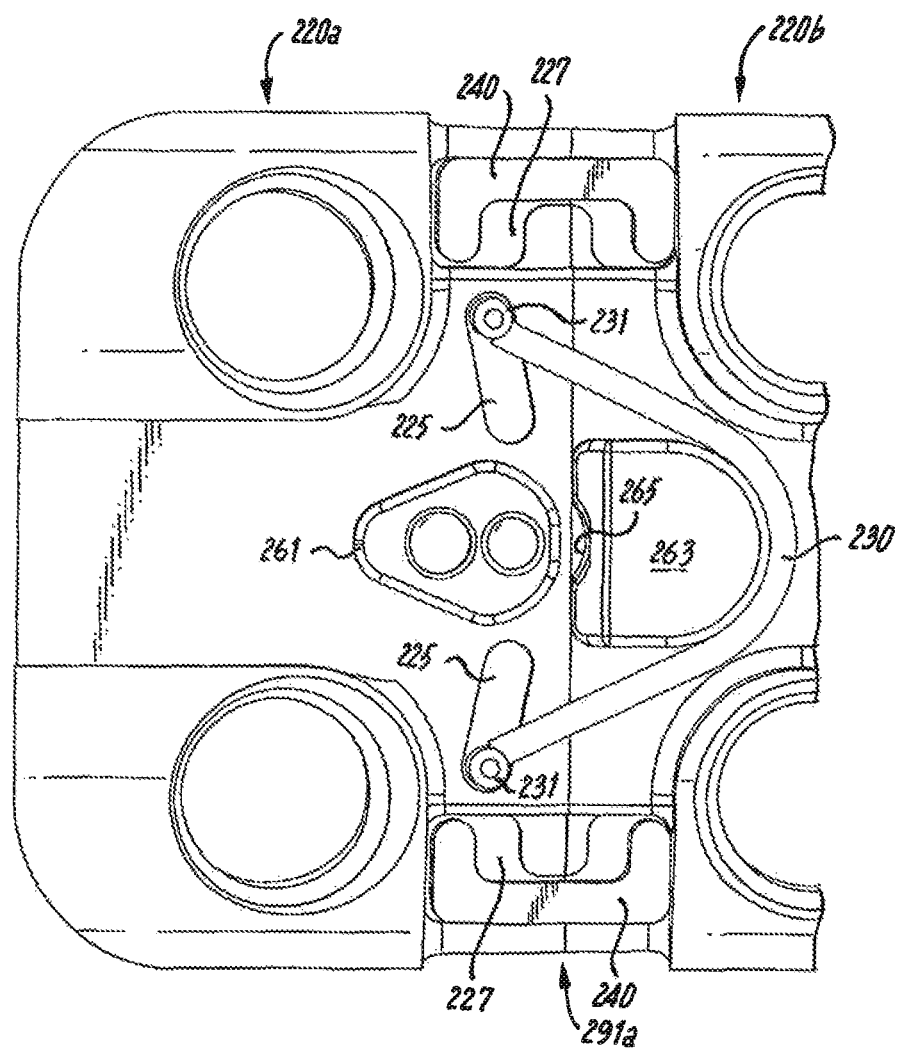
Figure 30C:
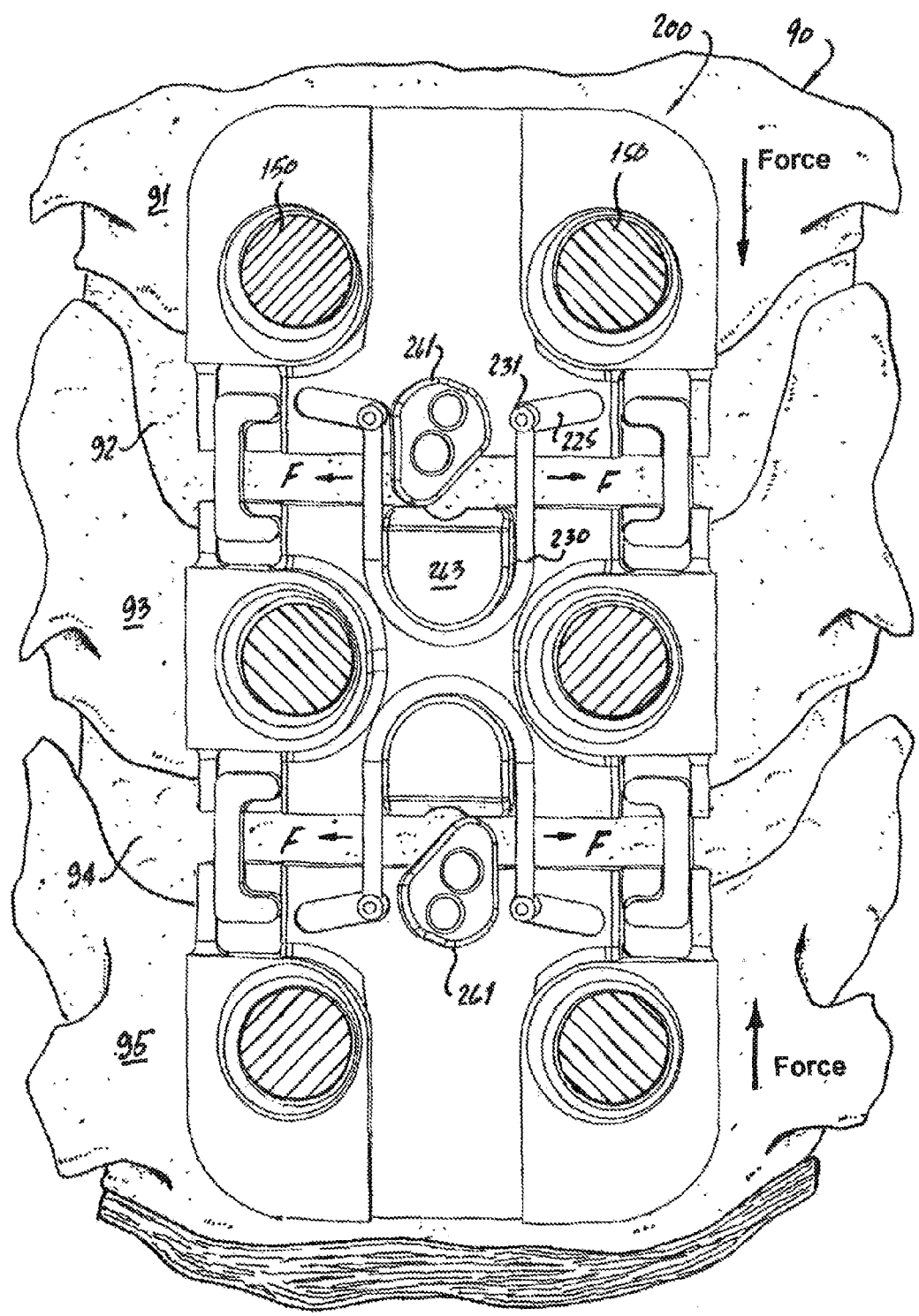

In the embodiment of the construct 200 of FIGS. 16-29, implantation of which is illustrated in FIGS. 30A, 30B and 30C, the springs 230 are arcuately-shaped rod or bar elements, formed from a resilient material. In accordance with a preferred aspect, the springs 230 are formed of a shape memory alloy, such as Nitinol. In accordance with one aspect, the springs 230 are linear in their natural state and are bent into the illustrated arcuate configuration upon assembly of the construct 200. The diameter of the springs 230 is selected based on the desired amount of force to be applied. Accordingly, the springs 230, in attempting to revert to their natural configuration, rotate in an outward arc, exerting initially a substantially laterally outward force through the pins 231 at the ends thereof to the outer plate segments 220a, 220c by way of the slots 225 formed therein.

The slots 215 formed in the underside of the top plate follow the arc of the pins 231 caused by the spring 230. The slots 225 in the lower end plate segments 220a, 220c are linear in configuration, with the longitudinal component of the arc of travel of the pins 231 being provided in the translation of the plate segments 220a, 220c themselves, in closing the gaps 291a, 291b. The linear configuration of the slots 225 of the lower end plate segments 220a, 220c in which the pins 231 ride, promote resolution of the generally arcuate application of spring force into an axial force, parallel to the translation of the end plate segments 220a, 220c. As can be appreciated, any transverse component of force applied by the spring will be applied symmetrically by each of the pins 231, which forces will therefore cancel one another within the outer plate segments 220a, 220c, and not result in any net external forces.

As configured, the slots 225 are not perfectly parallel to the edge of the plates 220a, 220c. The degree of angle of the slots 225 is provided to increase the distance of translation of the outer plate segments 220a, 220c across which sufficient force application is applied.

In accordance with the invention, a target force application can be between about 0 N and 90 N (between about 0-20 pounds-force). In accordance with one embodiment of the invention, a target force application is between about 13 N and 44 N (between about 3-10 pounds-force) for applications on a cervical vertebral segment. Alternatively, depending on the spinal segment, the target force application can be greater or smaller. In accordance with another embodiment of the invention, a target force for application is between about 44 and 89 N (between about 10-20 pounds-force) for thoracic or lumbar vertebral segments. As discussed herein, if resistance to compressive forces are desired and application of a preload by any of the constructs described herein is not desired, then such target force is 0N. Any application of force sufficient to safely achieve the desired effect is possible in accordance with the invention.

Figure 28:
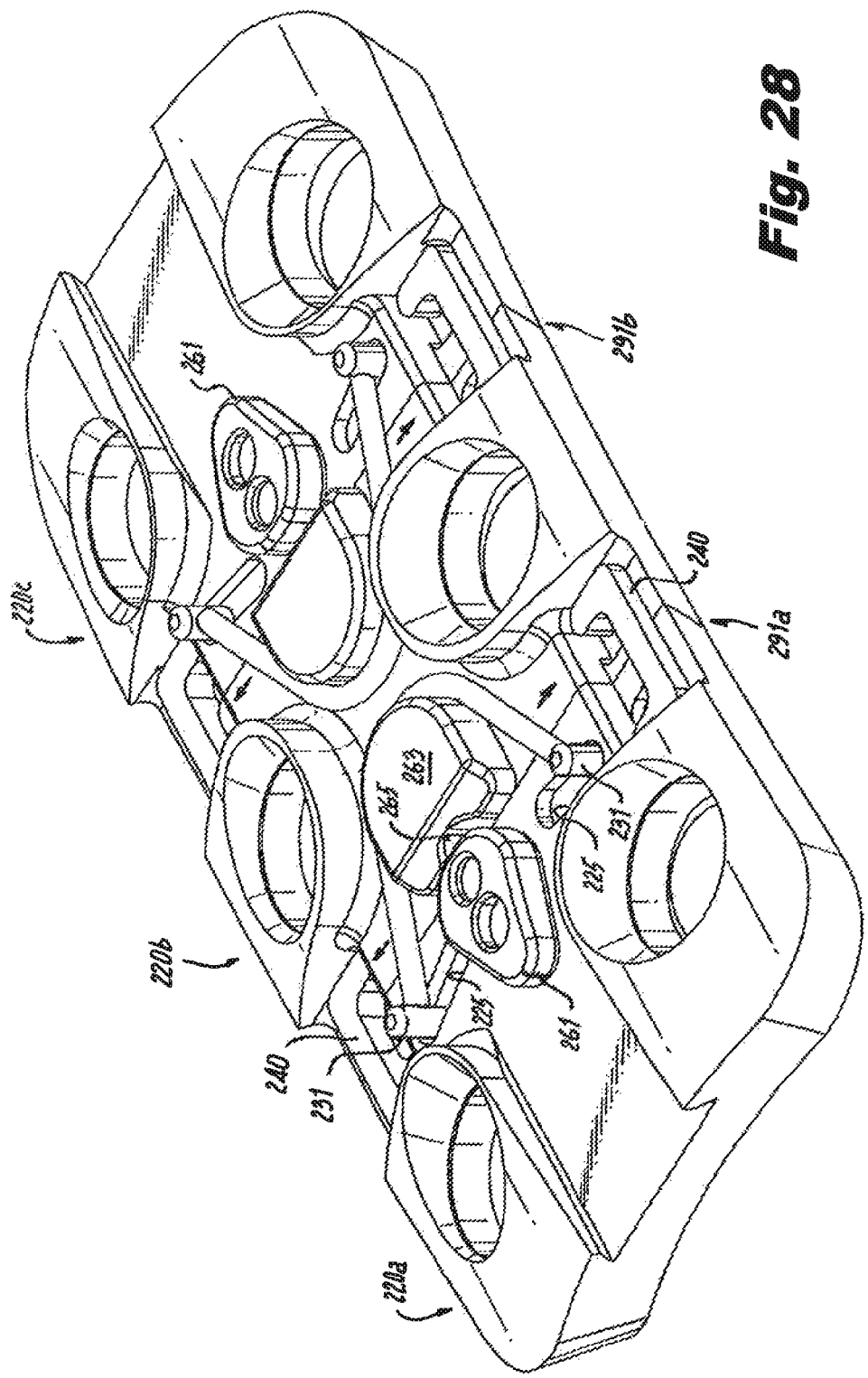

FIG. 26 illustrates the construct 200 in an expanded condition, just after disengagement of the cams 261 from the opposing recesses 265. As illustrated in FIGS. 28 and 29, in the absence of an attached spinal segment, upon disengagement of the cam 261 from the opposing recess 265, the outer plate segments 220a, 220c are pulled inward by the action of the springs 230.

FIGS. 30A-C illustrate implantation of the dynamic vertebral column plate system construct 200 of FIGS. 16-29 in various stages of attachment to a spinal segment 90. FIG. 30A illustrates the construct 200, in an expanded condition, attached to three vertebral bodies 91, 93 and 95, and spanning two inter-vertebral spaces 92 and 94 of a spinal segment 90, and insertion of a screw 150 with an insertion tool 81 therefor. FIG. 30B illustrates the construct 200 during disengagement of the lower cam 261 with a tool 83 therefor. FIG. 30C is a plan view of the construct 200, with the upper plate 210 removed for visibility, following disengagement of each cams 261 from its respective opposing recess 265. Force applied by the springs 230 is indicated by arrows, with resultant force applied to the spinal segment illustrated by arrows parallel to the longitudinal axis thereof. As illustrated, the cams 261 can't rotate fully away from the adjacent plate due to the position of pins 231 following disengagement. However, as settling occurs and the pins 231 move laterally outward, the cam 261 can continue to rotate away from the adjacent plate.

Figure 31A:
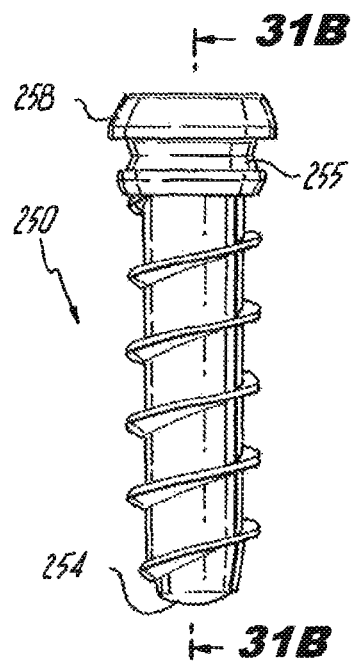
FIGS. 31A-H are side and cross-sectional views of various screw configurations for use with the dynamic vertebral column plate systems of the invention.
Figure 31B:
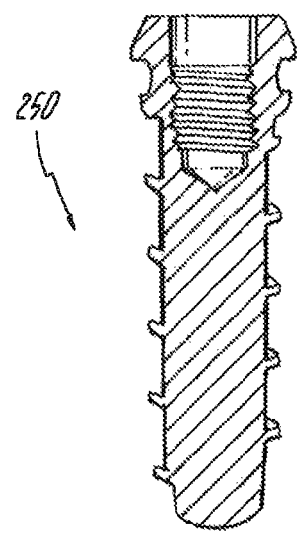

FIGS. 31A-H are side and cross-sectional views of various screw configurations for use with the dynamic vertebral column plate systems of the invention. FIGS. 31A and 31B illustrate a screw 250 having a self-tapping end 254 and a head 258 permitting variable angle engagement with an attached plate. A groove 255 is provided in the head 258 of the screw 250 for receiving a locking element, which can be any suitable element, including but not limited to a resilient o-ring, cir-clip, or another suitable element, such as a latching toroidal coil available from Bal Seal Engineering, Inc. of Foothill Ranch, Calif., USA. The locking element can be formed of any suitable material, such as a metal, metal alloys, an elastomeric material, silicone, polychloroprene (e.g. Neoprene), or a plastic material such as polyetheretherketone (PEEK), for example. The locking element, carried by the screw can seat in a groove provided in the construct being used.

Figure 31C:
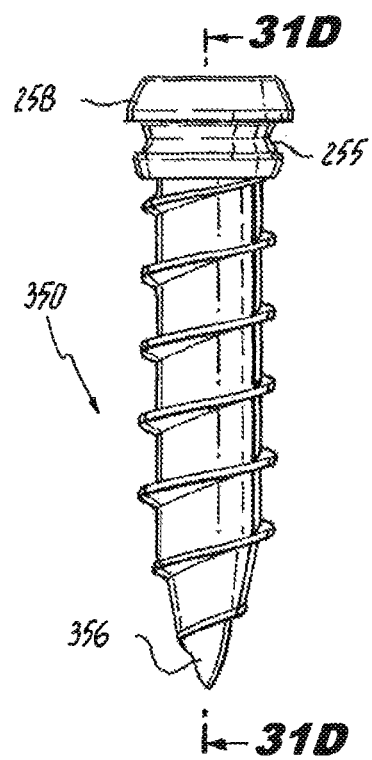
Figure 31D:
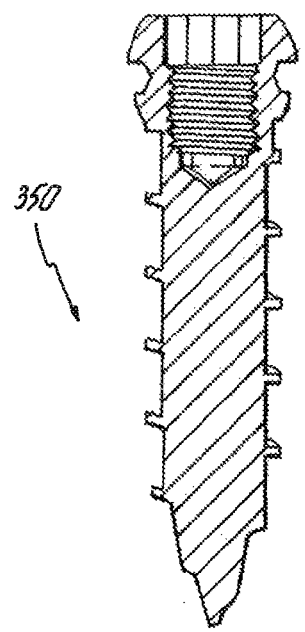
Figure 31E:
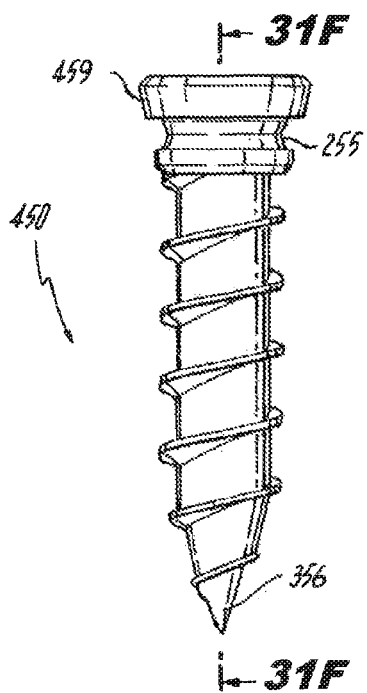
Figure 31F:
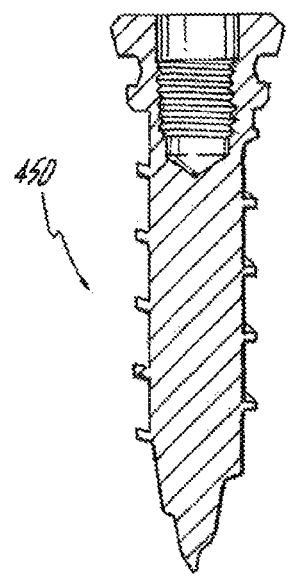
Figure 31G:
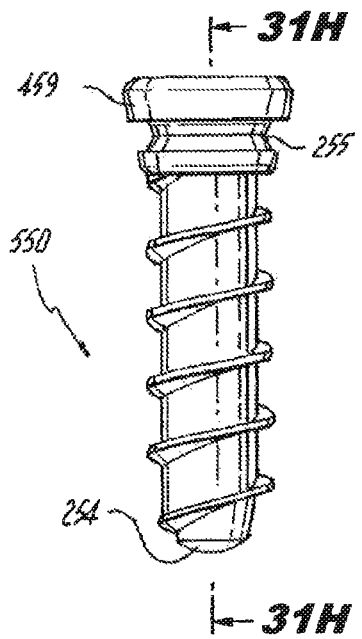
Figure 31H:
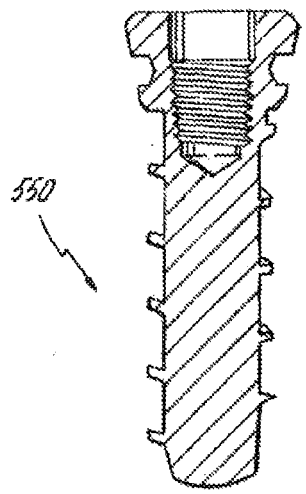

As with the screw 150 discussed in connection with the embodiment of FIGS. 1-15F, the screw 250 includes a socket 153 for engaging an insertion tool for implantation, and internal threads 157 are preferably provided to facilitate removal of the screw 250, if necessary. FIGS. 31C and 31D are side and cross-sectional views of a screw 350, having a head 258 permitting variable angle engagement, and a self-drilling end 356. FIGS. 31E and 31F are side and cross-sectional views of a screw 450 having a head 459 permitting only fixed-angle engagement with an attached plate, due to the trapezoidal cross-section thereof, as compared with the more rounded cross-section of the head 258 of screws 250 and 350. The screw 450 also includes a self-drilling end 356. FIGS. 31G and 31H illustrate a screw 550 with a head 459 for fixed-angle engagement, and a self-tapping end 254.

FIG. 32A is an isometric view of a dynamic vertebral column plate system construct 300 in accordance with the invention having two levels of plate segments, 320a, 320b and a unitary upper plate 310. The internal components can be any of those illustrated herein, but as illustrated, the construct 300 is provided with a spring arrangement similar to that of the construct 200 described in connection with FIGS. 16-29.

FIG. 32B is an isometric view of a dynamic vertebral column plate system construct 400 in accordance with the invention having four levels of plate segments, 420a, 420b, 420c and 420d, and a unitary upper plate 410. The internal components can be any of those illustrated herein, but as illustrated, the construct 400 is provided with a spring arrangement similar to that of the construct 200 described in connection with FIGS. 16-29. As discussed above, the intermediate plates 420a, 420b can be connected by way of a pin, or in an alternative manner.

In any case, it is generally preferred, but not required, that no more than one lower plate segment (e.g. 420a-d) be non-translatably secured to the upper plate 410. In the case of a two-level construct, one level can be pinned to the upper plate, or alternatively, both can be slideable with respect thereto. In the case of a three-level construct, as illustrated in FIGS. 16-29, the intermediate plate can be non-translatably secured by a pin or other feature. Although a dovetail feature can be applied to intermediate plates, connection with one or more pins may provide for easier assembly of the construct 400. Accordingly, in a four-level construct, as with construct 400, one of the intermediate plates, e.g., 420b can be non-translatably pinned, while the other of the intermediate plates e.g., 420c can be pinned by way of a slot 411 in the upper plate 410. Such a pin and slot 411 configuration can additionally be applied to, or alternatively in place of, any dovetail configuration described herein, if desired.

In accordance with the invention, the number of lower plates can be selected as desired. In practice, the number of lower plate levels that would typically be used would range from between two and six. Accordingly, any construct in accordance with the invention could include five or six levels, even though those are not explicitly illustrated herein.

FIGS. 33-39 various views of further exemplary embodiment of a dynamic vertebral column plate system construct 500 in accordance with the invention, having band-shaped springs 530 and an integral cam element 561 adapted and configured to permit a plurality of selectable preloads. The springs 530 can be formed of any suitable material, but in accordance with one preferred embodiment are a shape memory alloy, such as Nitinol.

Figure 33:
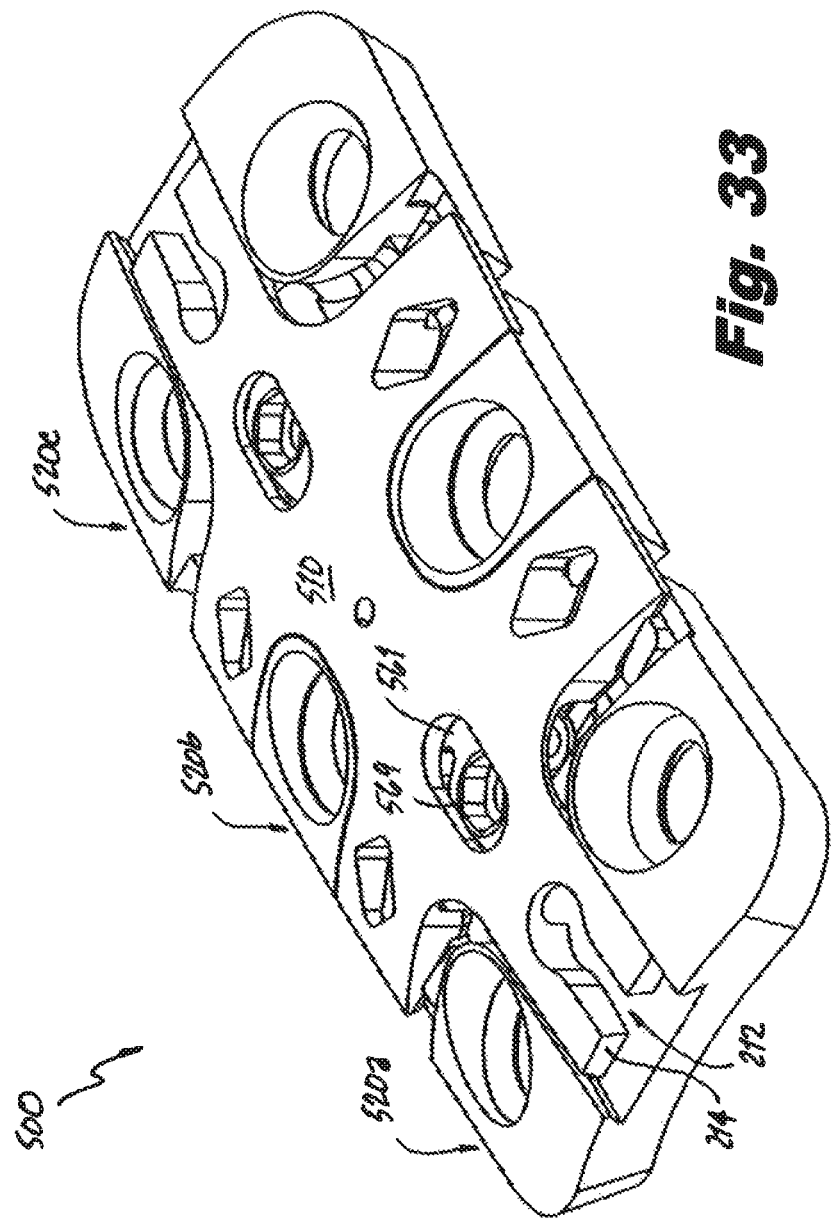
FIGS. 33-39 various views of further exemplary embodiment of a dynamic vertebral column plate system construct in accordance with the invention, having band-shaped springs and an integral cam element configured to permit a plurality of selectable preloads.
Figure 34:
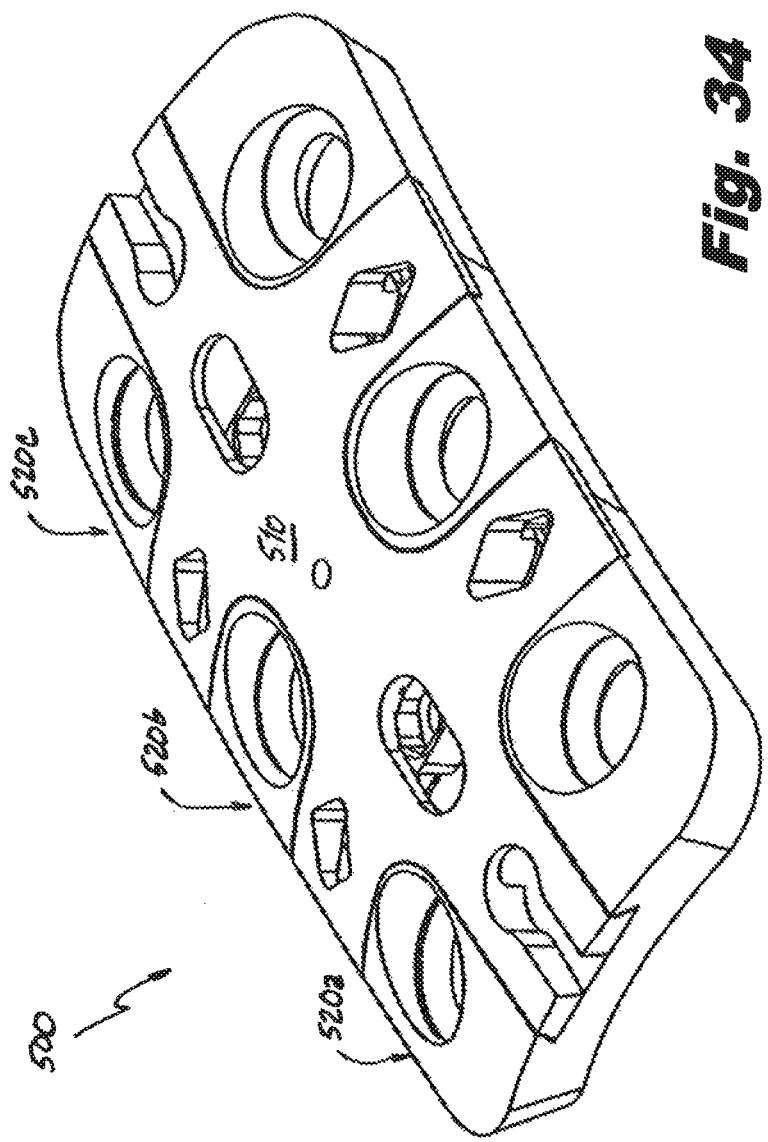
Figure 35:
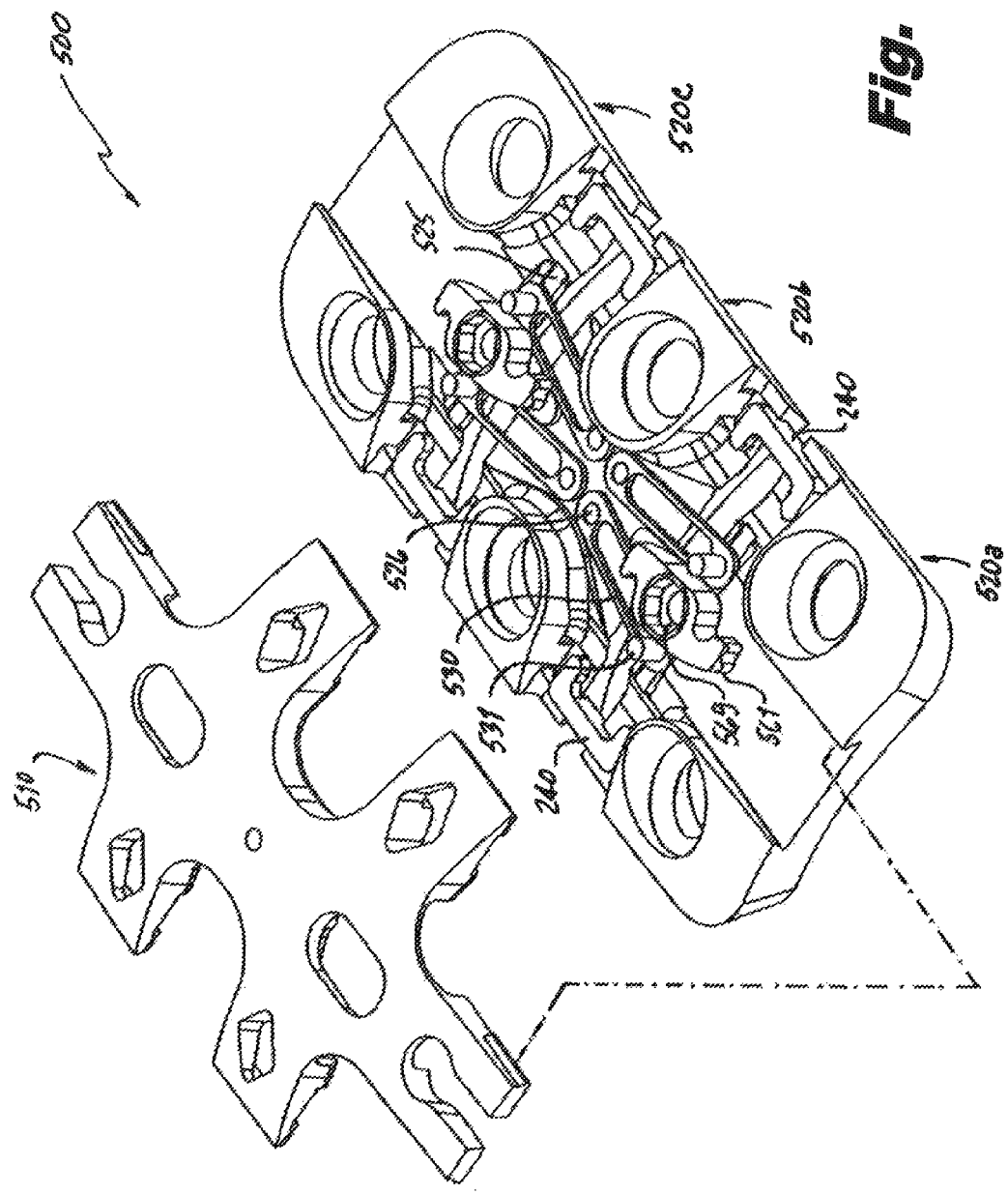
Figure 36:
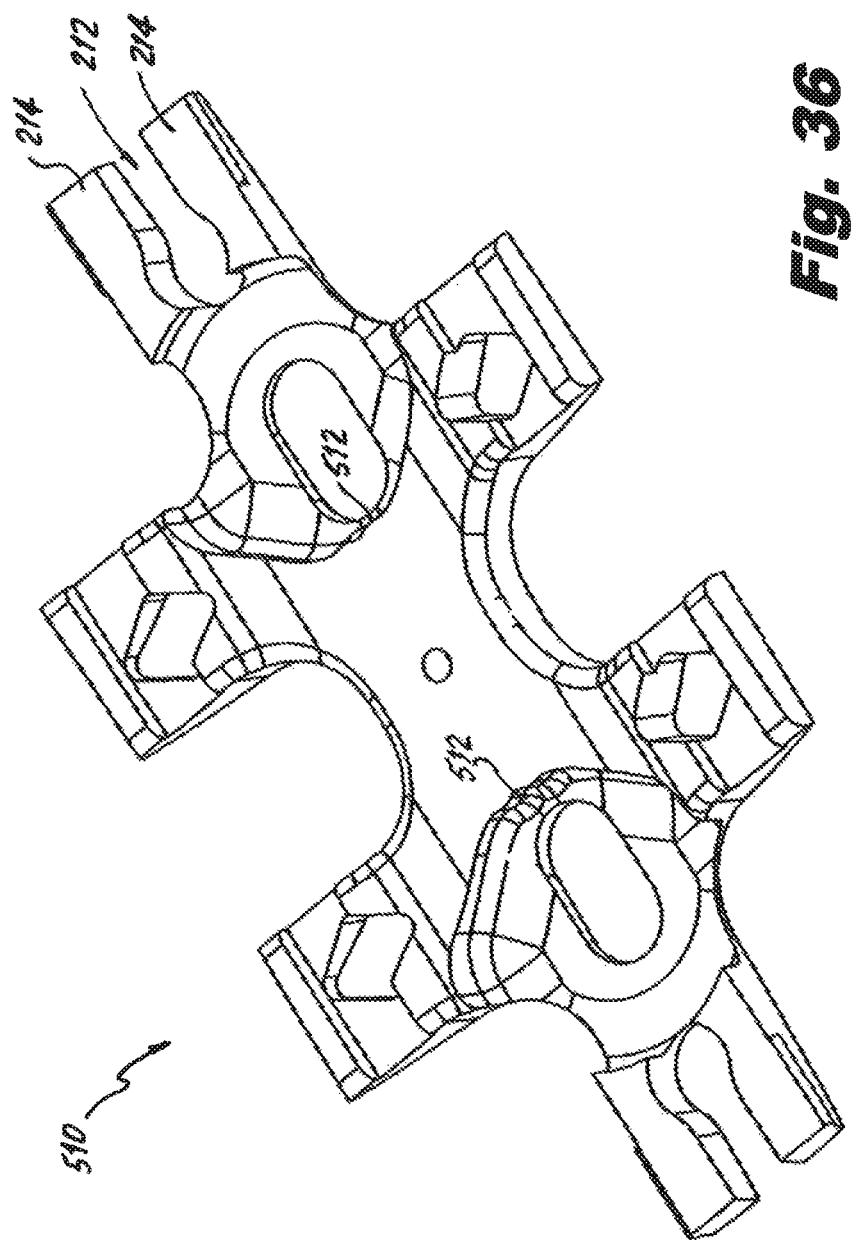
Figure 37:
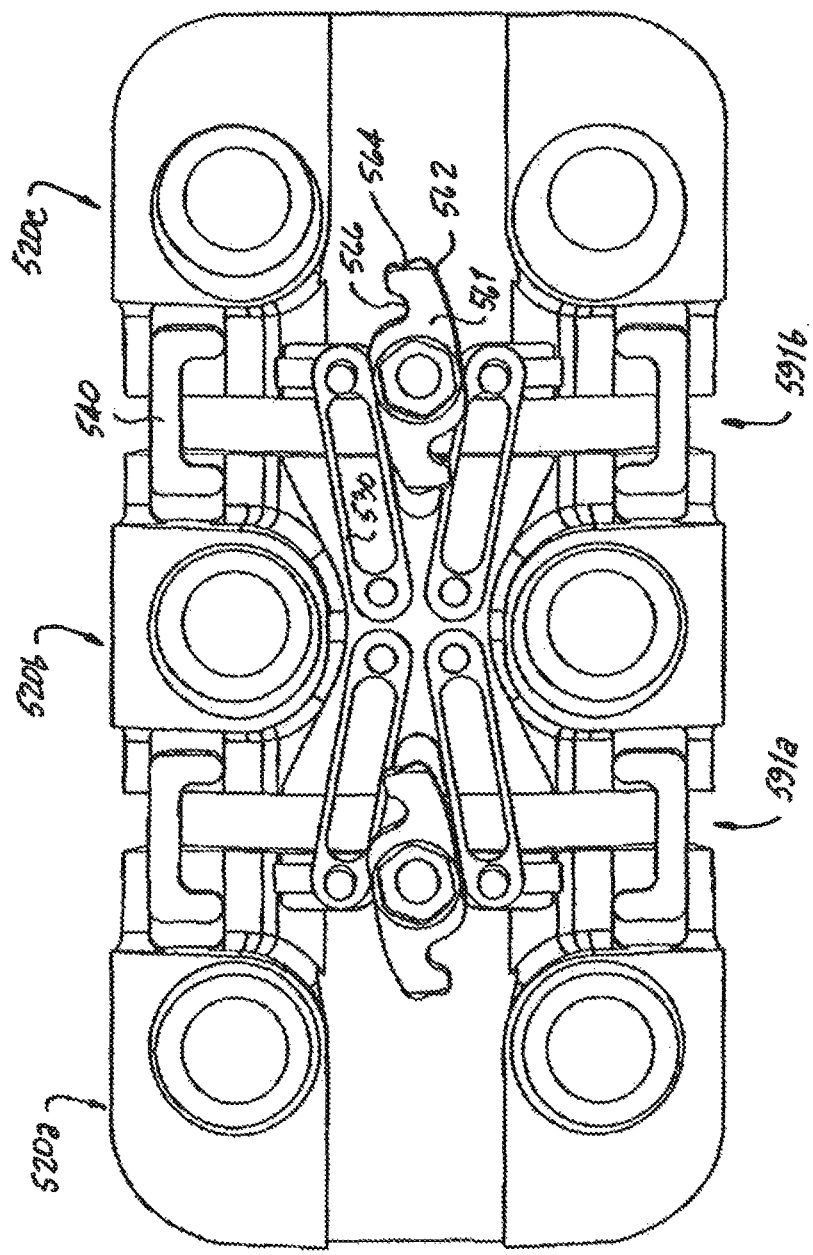

As with the construct 200 illustrated in FIGS. 16-29, a unitary upper plate 510 is provided. Different from that embodiment, however, the upper plate 510 of the construct 500 of FIGS. 33-39 includes a camming surface 512 on the underside thereof, as best seen in FIG. 36. When the cams 561 are rotated in line with the central axis of the construct 500, as illustrated in FIGS. 33, 35 and 37, they engage the camming surface 512, which then serves to push the outer plate segments 520a, 520c outward, away from the intermediate plate 520b, because the cams 561 are rotatably attached to the outer plate segments 520a, 520c, and the upper plate 510 is secured to the intermediate plate 520b. Accordingly, the construct 500 can in implanted with the cams 561 in such an orientation.

Following attachment of the construct 500 to a spinal segment, each of the cams 561 can be rotated either clockwise or counter-clockwise. The shape of the cams 561 is generally oblong, having opposed projections 562 extending therefrom, and a socket 569 to engage with a tool for actuating the cams 561. The projections 562 include on their outer ends, detents 564 for catching slideable pins 531 when the cams 561 are rotated clockwise, and inner hooks 566 for catching the slideable pins 531 when the cams 561 are rotated counter-clockwise. The two positions of each cam 561 permit selectable levels of tension of the springs 530, and thus selectable levels of preload applied to a spinal segment. Such a cam arrangement can be applied to the other embodiments of constructs described herein, including, but not limited to the construct 200 described in connection with FIGS. 16-29. As with the construct 200 described above, the slideable pins 531 are held in tracks 525, which are, as embodied, substantially parallel to the inner edges of the end plate segments 520a, 520c.

When implanting the construct 500 on a spinal segment, therefore, spacing between adjacent plates is maintained by the cams 561, engaging the camming surface 512 of the upper plate 510. Following attachment to respective vertebrae, one or more cams 561 can be left in the axial position, thus essentially providing a static plate at that level. If dynamic loading is desired at one or more levels, the respective cam 561 is then rotated either clockwise or counter-clockwise, as described above, securing the slideable pins 531 in either an intermediate position or at their most laterally outward extent.

Figure 38:
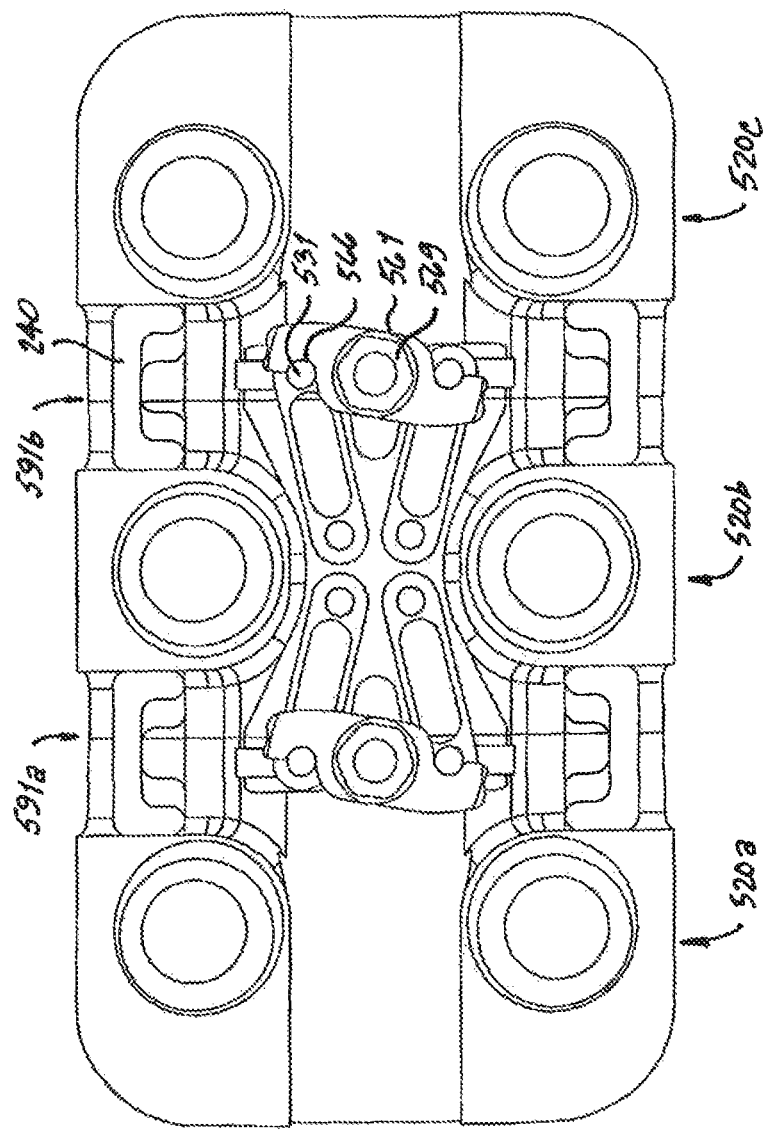

During implantation, a surgeon can apply the smaller of the two selectable preloads by rotating one or both of the cams 561 counter-clockwise, leaving the cam 561 in the position illustrated in FIG. 38. The surgeon can then evaluate whether the preload is sufficient to produce the desired effect, such as in reducing gaps between adjacent vertebrae and fusion materials. If an increased preload is desired, the cam 561 can then be rotated clockwise (by about one-half of a rotation), leaving the cam 561 in the position illustrated in FIG. 39, or vice versa.

Figure 39:
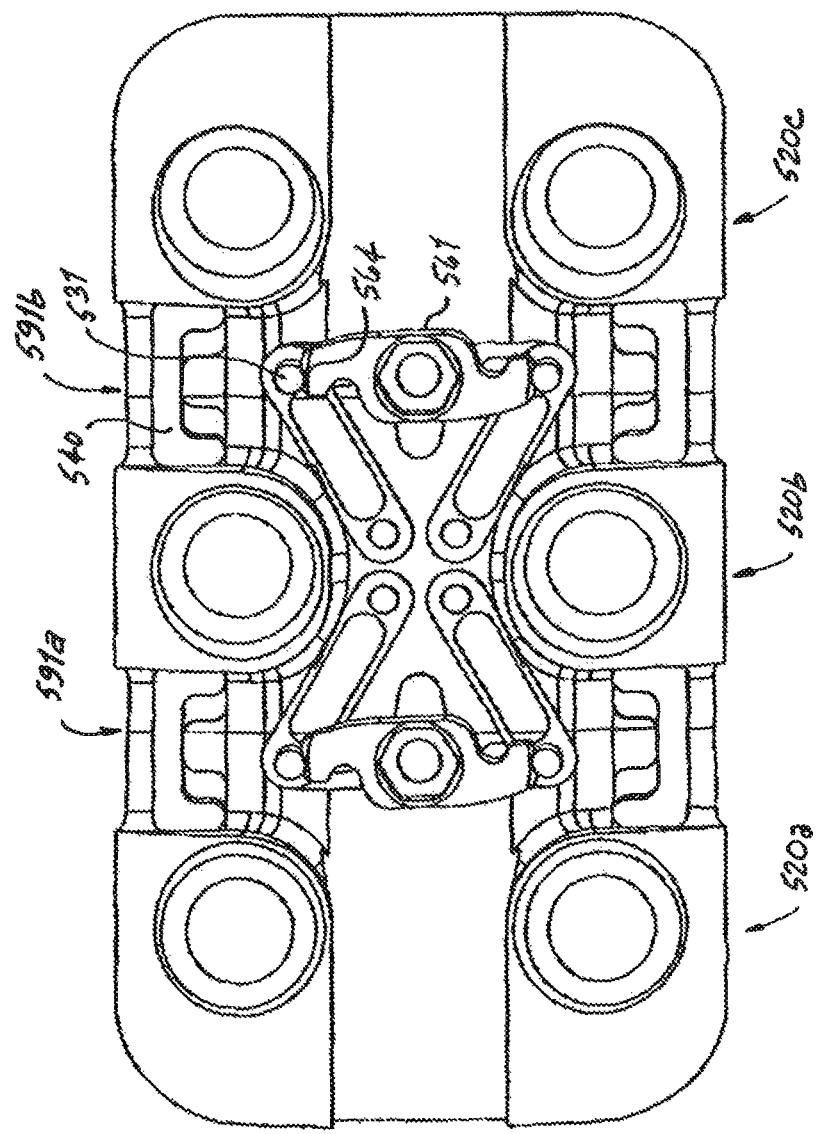

It should be noted that in the closed arrangement of the construct 500 illustrated in FIGS. 38 and 39, the gaps 591a and 591b are fully closed because the construct is not connected to a spinal segment. If the construct were connected to a spinal segment, gaps 591a, 591b would remain open indefinitely if the respective cam(s) 561 were left in the locked position (parallel to the longitudinal axis), and would likely remain open indefinitely to some extent, unless a fusion material settled to such an extent after implantation that the intervertebral space contracted by the entire amount of the respective gap 591a, 591b.

Materials for the components set forth above, including the plate segments 110, 120, can include stainless steels, titanium alloys, memory metals such as Nitinol, polymeric materials, ceramic materials such as silicon nitride or composite materials, for example.

Devices in accordance with the invention are applicable to any region of the vertebral column, such as from the first cervical vertebra (C1) to the first sacral vertebra (S1). When used in different locations along the spinal column, the plate segments 110, 120, engagement members 140, springs 130 and screws 150 are sized according to the size of the vertebral bodies in that region and to the loading conditions that will be experienced.

Figure 40:
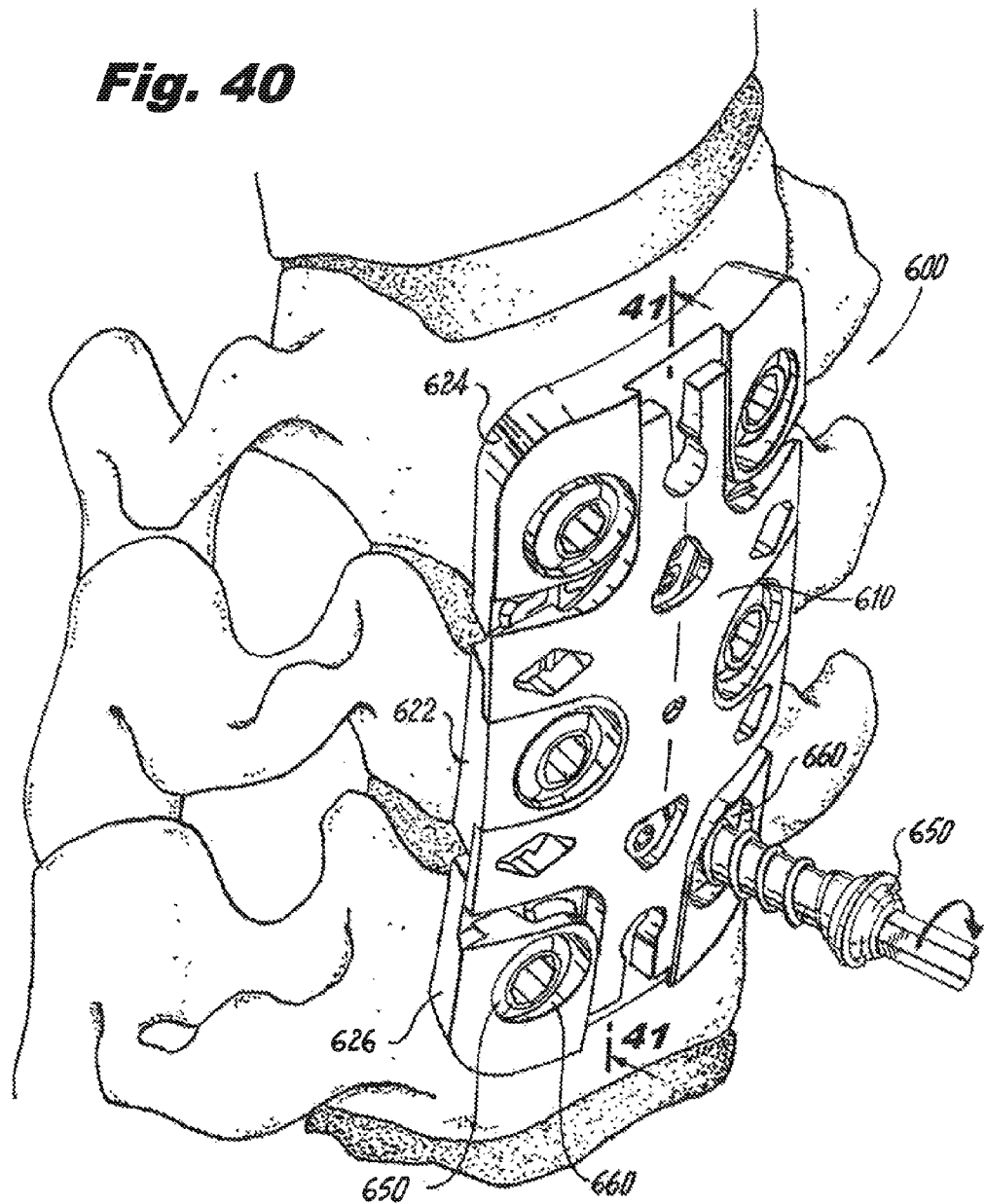
FIG. 40 is a perspective view of another dynamic spinal plate assembly constructed in accordance with a preferred embodiment of the subject invention, which includes structure for retaining bone screws.

Referring now to FIG. 40, there is shown a perspective view of another dynamic plate assembly constructed in accordance with a preferred embodiment of the subject invention, and designated generally by reference numeral 600. Plate assembly 600 includes an upper plate portion 610 covering a central plate segment 622, which is bounded by first and second outer plate segments 624 and 626. Each of the three plate segments includes a pair of spaced apart apertures 660. Each aperture 660 is configured to receive a bone screw 650 for securing the plate assembly 600 to bone structure with a patients body. As described in more detail below, plate assembly 600 includes structure for mechanically retaining the bone screws 650, to prevent them from backing out of the apertures 660 once they have been secured in bone.

Figures 41, 42, 43:
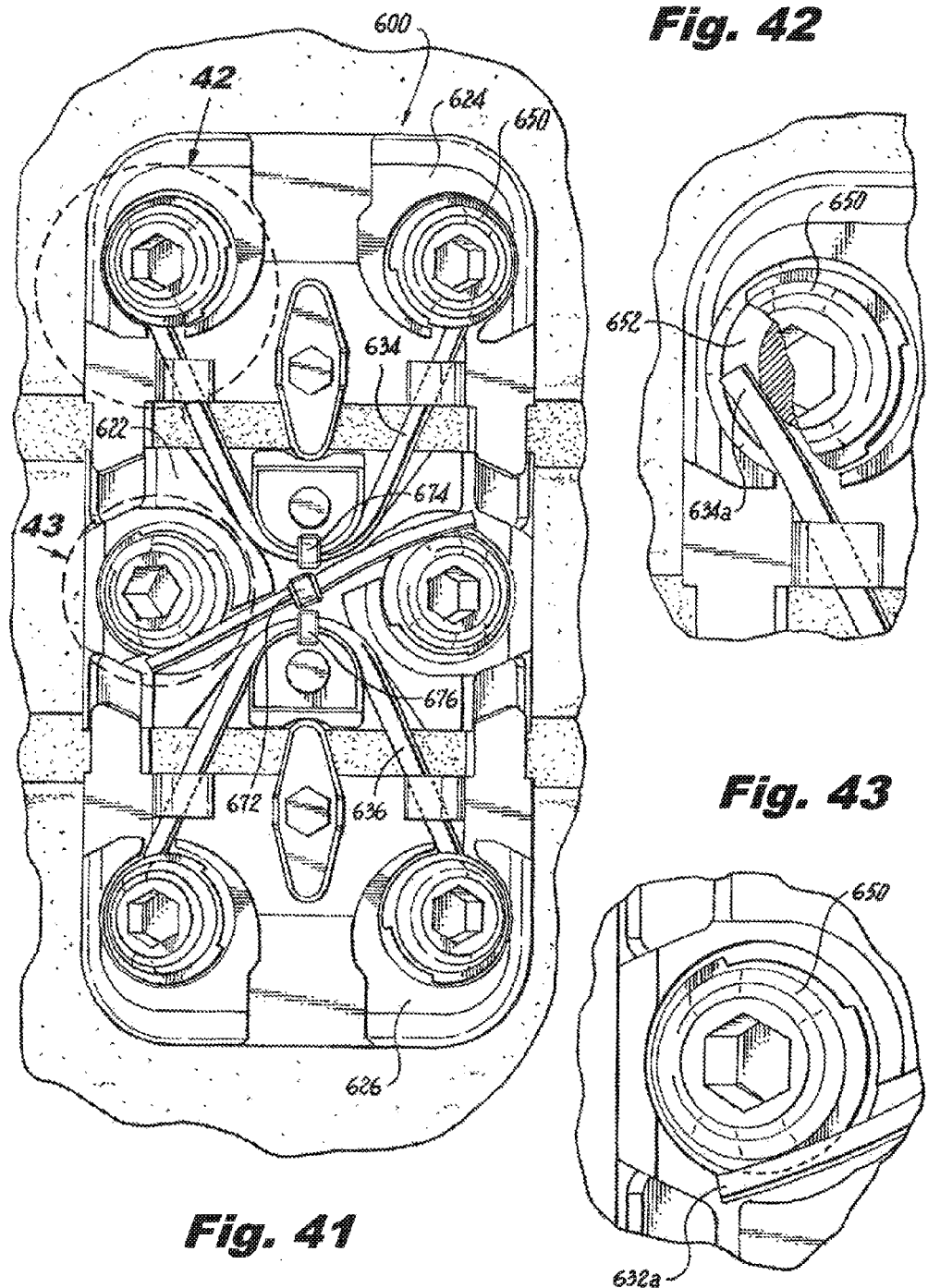
FIG. 41 is a top plan view of the spinal plate assembly shown in FIG. 40, with the upper plate portion removed to show the screw retention features of the plate assembly.
FIG. 42 is a localized view of the spinal plate assembly shown in FIG. 41, illustrating the screw retention feature, wherein the end portion of the generally U-shaped spring rod is engaged in a channel formed in the head of a bone screw to prevent the bone screw from backing out.
FIG. 43 is a localized view of the spinal plate assembly shown in FIG. 41, illustrating the screw retention feature, wherein the end portion of a central spring rod is engaged with an upper surface of the head of a bone screw to prevent the bone screw from backing out.

Referring to FIG. 41, the structure for retaining the head portion of the bone screws 650 associated with the first and second outer plate segments 624, 626 generally U-shaped spring rods 634 and 636. The spring rods 634, 636 are independently secured to central plate segment 622 by respective upstanding yokes 674 and 676. As best seen in FIG. 42, the free end 634a of U-shaped spring rod 634 engages an annular groove 652 formed in the head portion of screw 650.

Referring back to FIG. 41, the structure for retaining the head portions of the bone screws 650 associated with the central plate segment 622 is an elongated spring rod 632, which is disposed at an acute angle relative to a horizontal axis of the central plate segment 622 and secured to the central plate segment 622 by an upstanding yoke 672. The free ends of elongated spring rod 632 may engage an annular grove in the head of screw 650 as shown in FIG. 42 with respect to the free end 634a of rod 634, or, in the alternative, as best seen in FIG. 43, the free ends 632a of elongated spring rod 632 can engage an upper surface of the head portion of bone screw 650.

Figure 44:
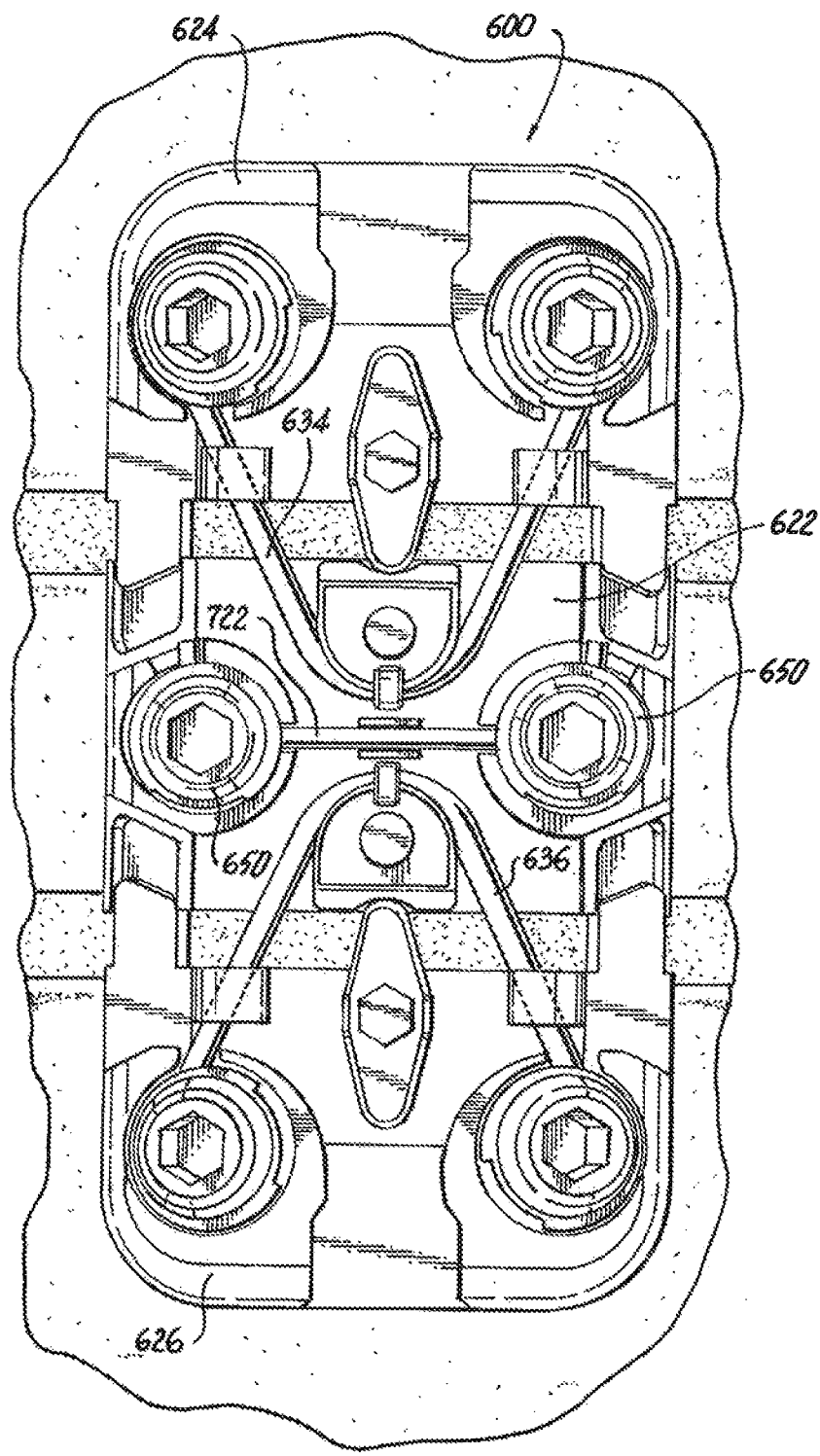
FIG. 44 is a plan view of another spinal plate assembly constructed in accordance with a preferred embodiment of the subject invention, which includes central screw retention structure in the form of a shaped spring rod.
Figure 45:
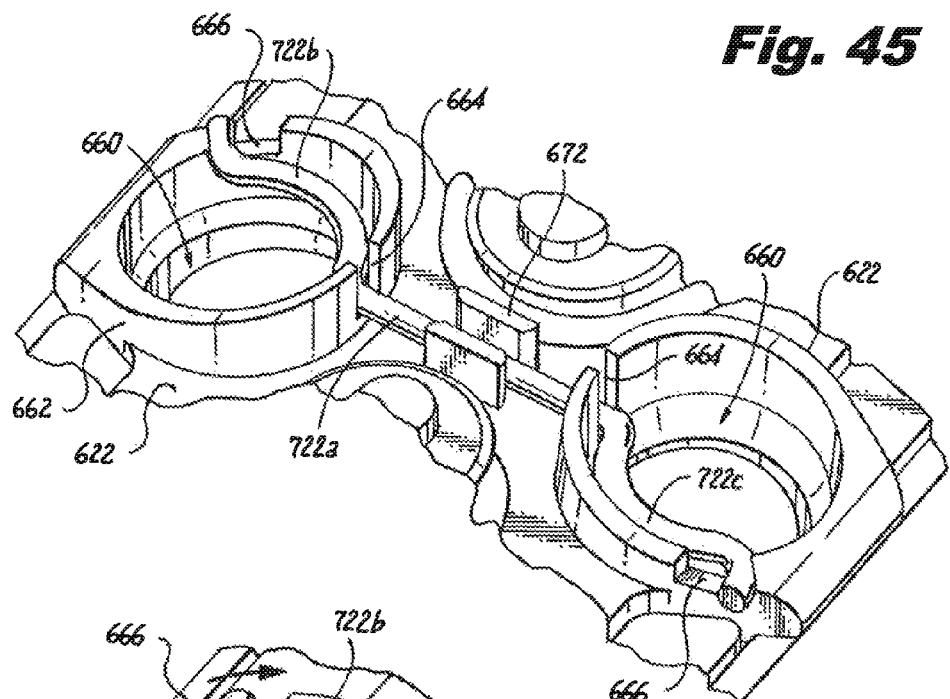
FIG. 45 is a localized perspective view of the central portion of the spinal plate assembly shown in FIG. 44, illustrating a shaped spring rod having a central mounting portion flanked on each side by a curved screw head retention portion.

Referring now to FIG. 44, there is shown another embodiment of dynamic plate assembly 600, which includes a shaped central spring rod 722 for retaining the bone screws 650 associated with the central plate segment 622. As best seen in FIG. 45, shaped spring rod 722 has an elongated central mounting portion 722a flanked by oppositely curved screw head retention portions 722b and 722c. Central plate segment 622 includes an upstanding yoke 672 for supporting the central mounting portion 722a of shaped spring rod 722.

The apertures 660 in central plate segment 622 are defined at least in part by an upstanding peripheral wall 662. A slot 664 is provided in the wall 662 of each aperture 660 in central plate segment 622 to accommodate the central mounting portion 722a of the spring rod 722, and a window 666 is formed in the wall 662 of each aperture 660 in plate segment 622 to accommodate passage of the free end of the curved retention portions of 722b and 722c of spring rod 722.

Figure 46:
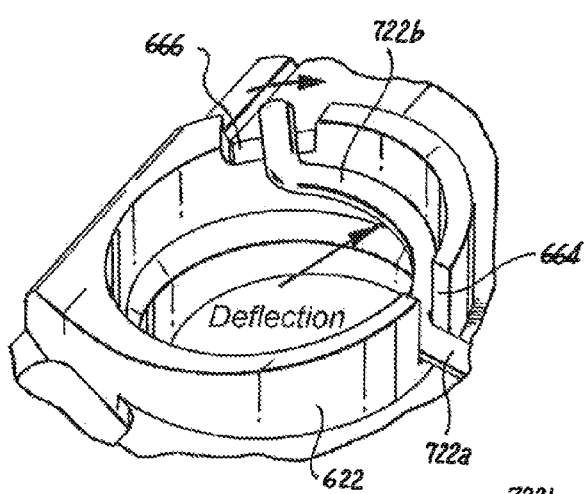
FIG. 46 illustrates the degree of flexure of the curved screw head retention portion of the shaped spring rod shown in FIG. 45.
Figure 47:
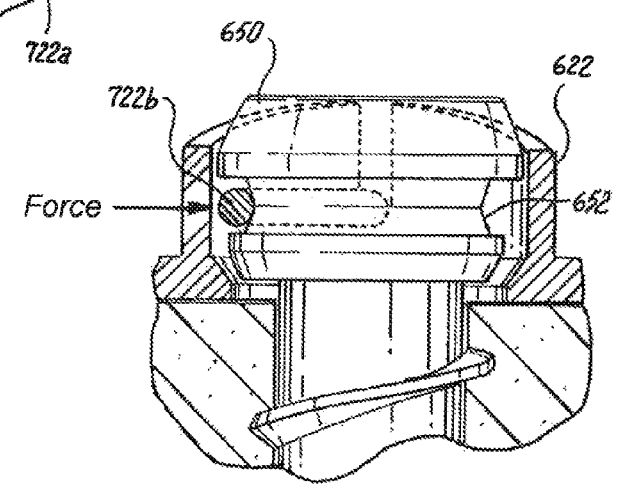
FIG. 47 illustrates the engagement of the curved screw head retention portion of the spring rod with a retention channel formed in the head of a bone screw.

As best seen in FIG. 46, the curved retention portions of 722b and 722c of spring rod 722 are resilient and deflectable to facilitate engagement with the head portion of a bone crew 650, as shown in FIG. 47, wherein, for example, the curved retaining portion 722b is actually engaged within a reception groove 652 formed in the head portion of the bone screw.

Referring now to FIG. 48, there is illustrated a dynamic bone plate assembly 800 that includes at least first and second plate segments 822 and 824, which are adapted and configured for movement relative to one another from a spaced apart position shown in FIG. 49 to an approximated position shown in FIG. 50. A ratcheting pawl member 882 is operatively associated with the first plate segment 822 and a rack of ratchet teeth 884 are provided on the second plate segment 824 for interacting with the pawl member 882. This ratchet mechanism allows the first and second plate segments 822, 824 to move from the spaced apart position of FIG. 49 to the approximated position of FIG. 50, while preventing the first and second plate segments 822, 824 from moving back toward a spaced apart position.

Figure 51:
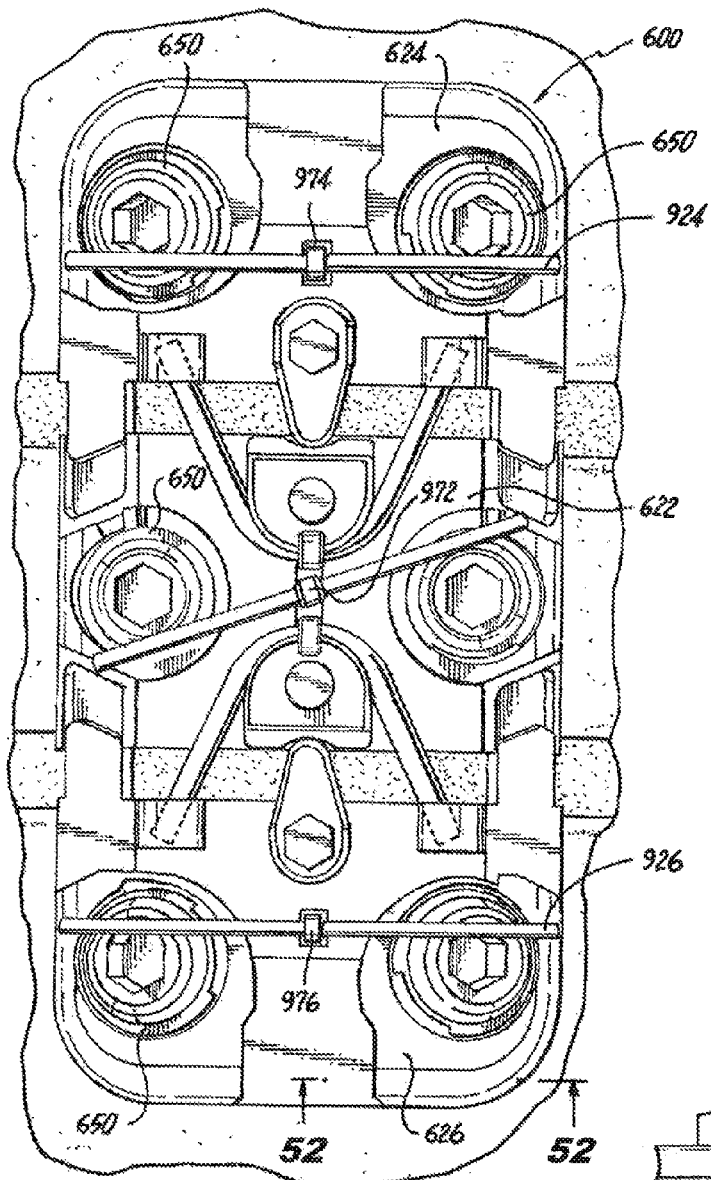
FIG. 51 is a plan view of yet another embodiment of a dynamic spinal plate assembly constructed in accordance with a preferred embodiment of the subject invention, which includes screw retention structure in the form of three transverse spring rods for retaining bone screws associated with each segment of the plate assembly by engaging upper surfaces of the heads of the bone screws.
Figure 52:
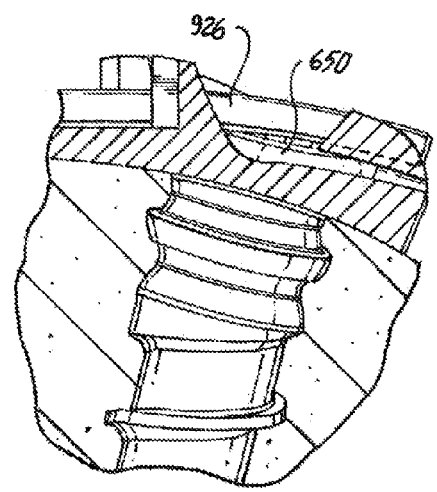
FIG. 52 is a cross-sectional view taken along line 52-52 of FIG. 51.

Referring now to FIG. 51, there is illustrated yet another embodiment of the dynamic bone plate assembly 600. In this instance, the structure for retaining the head portions of the bone screws 650 associated in each of the three plate segments 622, 624, 626 is an elongated spring rod. More particularly, the central plate segments 622 includes a central elongated spring rod 922 supported on an acute angle within an upstanding yoke 972, the first outer plate segment 624 includes a first transverse spring rod 924 supported within an upstanding yoke 974, and the second outer plate segment 626 includes a second transverse spring rod 926 supported within an upstanding yoke 976. In this embodiment of the plate assembly 600, the elongate spring rods 922, 924, 926 engage the upper surfaces of the heads of the bone screws 650 with which they are associated, as shown for example in FIG. 52 as to spring rod 926.

Figure 53:
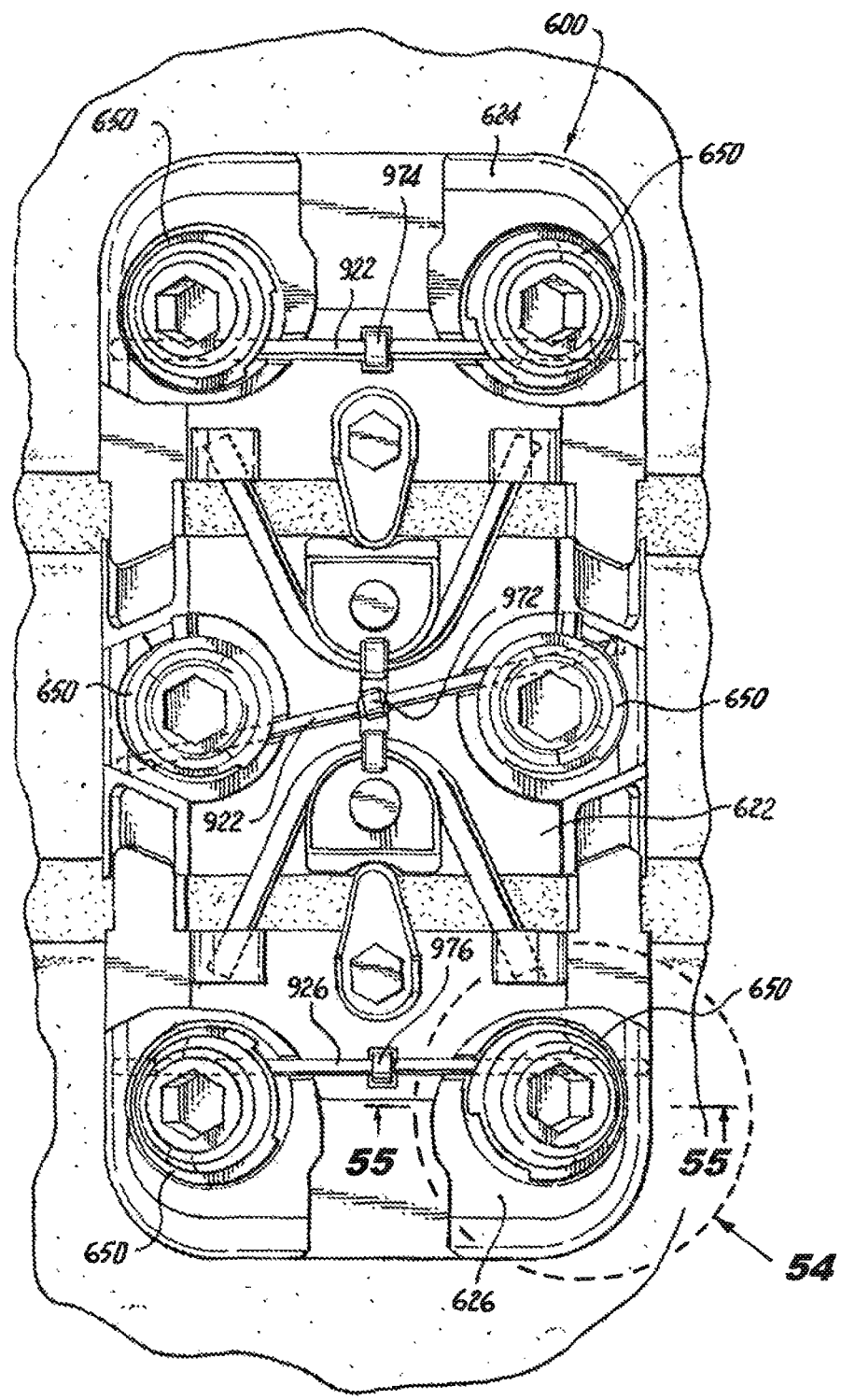
FIG. 53 is a plan view of yet another embodiment of a dynamic spinal plate assembly constructed in accordance with a preferred embodiment of the subject invention, which includes screw retention structure in the form of three transverse spring rods for retaining bone screws associated with each segment of the plate assembly by engaging retention channels formed in the heads of the bone screws.

Referring now to FIG. 53, there is illustrated still another embodiment of the dynamic bone plate assembly 600. In this embodiment, the structure for retaining the head portions of the bone screws associated in each of the three plate segments are also elongated spring rods 922, 924, 926. However, in this instance, the three elongate spring rods 922, 924, 926 extend into or otherwise intersect the screw apertures 660 as shown for example in FIG. 54, and engage retention channels 652 formed in the heads of the bone screws 650 as shown for example in FIG. 55. with which they are associated.

Figure 56:
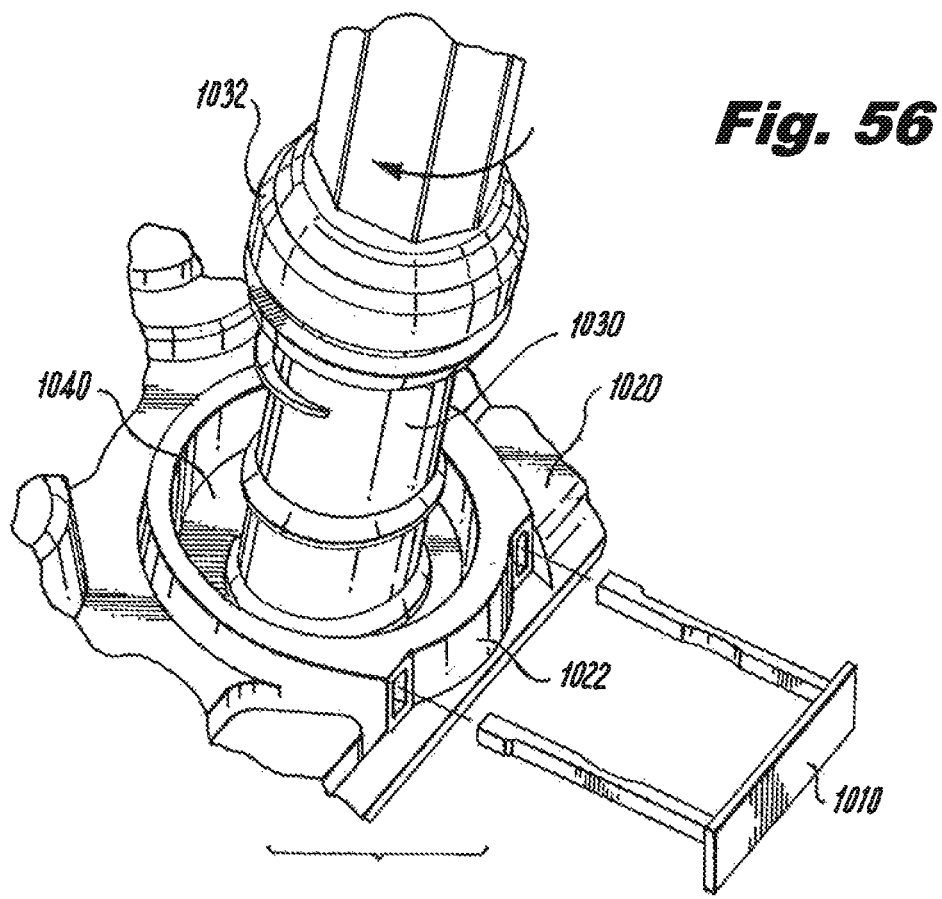
FIG. 56 is a perspective view of a section of a bone plate with an associated bone screw, together with a retention clip configured to engage the head of the bone screw through the side wall of the plate.
Figure 57:
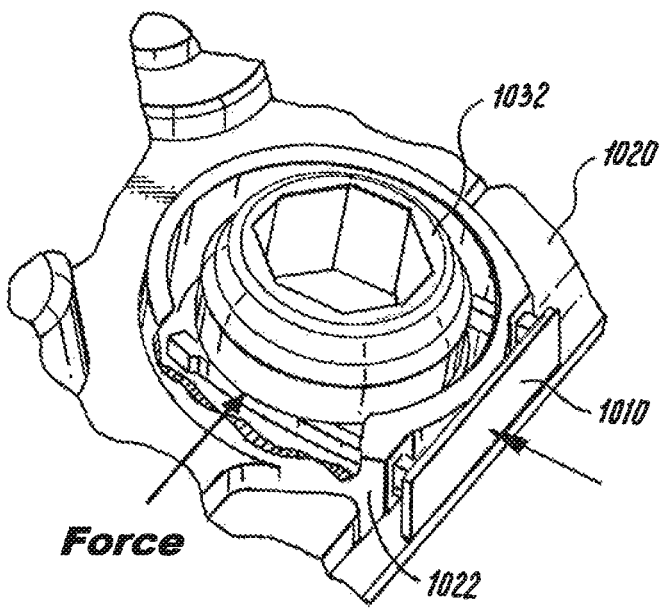
FIG. 57 is a perspective view showing the retention clip engaging the head of the bone screw through the side wall of the plate.

Turning now to FIGS. 56 and 57, there is illustrated a generally π-shaped screw retention clip 1010 that is associated with a segment of a bone plate 1020 for retaining a bone screw 1030 with respect to the bone plate 1020. The retention clip 1010 is adapted and configured to biasingly or resiliently engage the head 1032 of the bone screw 1030, or a retention channel formed within the head of the bone screw, through the side wall 1022 of the plate 1020, to prevent the bone screw 1030 from backing out of the aperture 1040 in which it is received. It should be readily appreciated by those skilled in the art that in a plate assembly having multiple plate segments, each having a plurality of bone screws, there will be provided a respective plurality of retention clips 1010, one for each of said bone screws.

Kits in accordance with the invention can be provided, and include a range of plate sizes, springs 130 with varying stiffnesses, engagement members with varying stiffnesses and/or shapes, bone screws of varying sizes, and can include fixed and/or variable angle (polyaxial) screws. Kits can include plates having sizes suitable for cervical and/or thoracic and/or lumbar and/or sacral application.

The devices, systems and methods of the present invention, as described above and shown in the appended drawings, provide for vertebral column plate system constructs and related systems, methods and kits with superior properties and versatility, and adaptably enhance fusion of a bone graft.

In short, constructs in accordance with the invention can be selectively dynamic, the dynamism can be passive or active, and if active, a level of preload can be easily selected. That is, constructs in accordance with the invention can be used as completely static (being dynamically active at no levels) constructs, can be used as static at one or more levels and dynamic at the remaining levels, or can be used as dynamic at all levels. Moreover, the selectable dynamism can be active, such as in which a preload is applied by the construct, or alternatively passive, in which forces are managed through load sharing between the attached spinal segment and the construct.

In applications of passive dynamism in accordance with the invention, constructs can be configured to provide a predetermined amount of resistance to compressive forces in translation and/or bending between adjacent plate segments, thereby allowing for a predetermined amount of load sharing between the construct and the vertebral column segment. The active dynamism can include a preload that is selectable, such as by varying tension in one or more members, such as in one or more springs. Moreover, it should be noted that although the term "spring" is used herein, it is to be understood that the appearance of such a spring can vary from and is not limited to conventional notions of springs.

It is to be understood that Applicant conceives that features described herein in connection with one embodiment can advantageously be applied any other embodiment described herein, even if such feature is not explicitly described in connection with such embodiment, except where such features are mutually exclusive. That is, it is specifically conceived that elements of one embodiment are interchangeable with those of another embodiment, without limitation, except if such features would be incompatible with other features or necessarily displace another feature, for example.

It will be apparent to those skilled in the art that further modifications and variations can be made in the devices, systems and methods of the present invention without departing from the spirit or scope of the invention. For example, while each of the screw retention structures disclosed herein are illustrated as shaped rods that are circular in cross-section, it is envisioned and well within the scope of the subject disclosure that the screw retention rods can have alternative cross-sectional geometries. For example, the rods could have a square cross-section as in the case of a slender bar or staff. It should also be understood that these screw retention structures can be manufactured through a variety of conventional cutting or stamping forming operations that are known in the art.

Furthermore, it should be readily appreciated by those having ordinary skill in the art that the dynamic plating systems described and illustrated herein are not limited in use or application to spinal stabilization. Rather, it should be appreciated by those skilled in the art that the constructs disclosed herein can be readily modified and used to stabilize other types of bone structure throughout a patient's body, including, but not limited to applications involving the dynamic stabilization of bone fractures presented in the limbs of a patient.

What is claimed is:

1. A bone plate assembly comprising: a bone screw; at least one plate segment having at least one aperture extending therethrough for receiving a head portion of the bone screw; means supported by the plate segment and intersecting the aperture for retaining the head portion of the bone screw with respect to the plate segment; wherein the means for retaining the head portion of the bone screw is defined by a spring rod, wherein the head portion of the bone screw includes a reception groove for engagement by a retention portion of the spring rod, wherein the spring rod has a central mounting portion flanked by at least one curved screw head retention portion, wherein the plate segment includes an upstanding yoke for supporting a central mounting portion of the spring rod.

2. A bone plate assembly as recited in claim 1, wherein the spring rod is generally U-shaped.

3. A bone plate assembly as recited in claim 1, wherein the spring rod is elongated.

4. A bone plate assembly as recited in claim 1, wherein the aperture is defined at least in part by an upstanding peripheral wall, and a window is formed in the wall for accommodating passage of a retention portion of the spring rod.

5. A bone plate assembly comprising: a plurality of interconnected plate segments each having a pair of apertures extending therethrough for receiving a head portion of a bone screw; and means supported by each plate segment and extending into the apertures associated therewith for retaining the head portion of the bone screws with respect to the plate segment, wherein the means for retaining the head portion of the bone screws is defined by a spring rod, wherein the bone plate assembly includes a pair of outer plate segments and a central plate segment, and wherein the means for retaining the head portion of the bone screws is of each outer plate segment is a generally U-shaped spring rod, wherein the means for retaining the head portion of the bone screws in the central plate segment is an elongated spring rod, wherein the means for retaining the head portion of the bone screws is the central plate segment is an elongated spring rod having a central mounting portion flanked by oppositely curved screw head retention portions.

6. A bone plate assembly as recited in claim 5, wherein: each U-shaped spring rod is independently secured to the central plate segment by a respective upstanding yoke for providing a compressive force between the respective segments; and each free end of the U-shaped spring rod engages a head portion of a screw.

7. A bone plate assembly comprising: at least one plate segment having at least one aperture extending therethrough; at least one bone screw for passing through the at least one aperture, the at least one bone screw having a head portion; and a spring rod supported by the at least one plate segment and having a central mounting portion flanked by at least one screw head retention portion, wherein the plate segment includes an upstanding yoke for supporting a central mounting portion of the spring rod, wherein the at least one screw head retention portion intersects the aperture for retaining the head portion of the bone screw and is deflectable to facilitate engagement with the head portion of the bone screw, wherein the at least one screw head retention portion is curved and the head portion of the bone screw includes a reception groove for engagement by the retention portion of the spring rod.

8. A bone plate assembly as recited in claim 7, wherein the head portion of the bone screw forms a flange, the flange having: a proximal surface for engaging the at least one screw head retention portion when the bone screw is deployed; and a distal surface contoured to deflect the at least one screw head retention portion outward as the head portion passes by the at least one screw head retention portion during deployment of the bone screw.

* * * * *